United States Patent
Marton et al.

(10) Patent No.: US 12,048,666 B2
(45) Date of Patent: Jul. 30, 2024

(54) SYSTEM AND PROCESS FOR DETERMINING PRESSURE SETTINGS FOR A PERCUSSIVE MASSAGE APPLICATOR

(71) Applicant: HYPERICE IP SUBCO, LLC, Irvine, CA (US)

(72) Inventors: Robert Marton, San Diego, CA (US); Anthony Katz, San Diego, CA (US); Bostjan Buc, Irvine, CA (US); James Huether, Irvine, CA (US)

(73) Assignee: HYPERICE IP SUBCO, LLC, Irvine, CA (US)

( * ) Notice: Subject to any disclaimer, the term of this patent is extended or adjusted under 35 U.S.C. 154(b) by 946 days.

(21) Appl. No.: 17/083,118

(22) Filed: Oct. 28, 2020

(65) Prior Publication Data

US 2021/0038472 A1   Feb. 11, 2021

Related U.S. Application Data

(63) Continuation-in-part of application No. 16/887,383, filed on May 29, 2020, now Pat. No. 11,701,294,
(Continued)

(51) Int. Cl.
*A61H 23/00* (2006.01)
*A61H 1/00* (2006.01)
*A61H 23/02* (2006.01)

(52) U.S. Cl.
CPC .......... *A61H 23/006* (2013.01); *A61H 1/008* (2013.01); *A61H 23/004* (2013.01);
(Continued)

(58) Field of Classification Search
CPC .............. A61H 23/00–06; A61H 1/008; A61H 2201/5071; A61H 2201/5074; A61H 7/00–008
See application file for complete search history.

(56) References Cited

U.S. PATENT DOCUMENTS

| | | |
|---|---|---|
| 1,594,636 A | 8/1926 | Smith |
| 1,784,301 A | 12/1930 | Mekler |

(Continued)

FOREIGN PATENT DOCUMENTS

| | | |
|---|---|---|
| CA | 188544 A | 2/1919 |
| CA | 188545 A | 2/1919 |

(Continued)

OTHER PUBLICATIONS

Amazon, "Theragun G3PRO Percussive Therapy Device", Feb. 13, 2019. <https://www.amazon.com/dp/> B07MJ2MCT3/ref=nav_timeline_asin?_encoding=UTF8&psc= 1. Shown on p. 1 (Year: 2019).

(Continued)

*Primary Examiner* — Valerie L Woodward
(74) *Attorney, Agent, or Firm* — Goodwin Procter LLP

(57) ABSTRACT

Systems and processes for determining pressure settings for a percussive massage applicator are described. According to one embodiment, a method comprises obtaining an operational current measurement of the motor when the motor has a load. difference value is determined between the current measurement and the operational current measurement. The difference value is compared to two or more predetermined ranges of values that correspond to a pressure level of the percussive applicator. The pressure level may be provided as feedback to the user.

20 Claims, 34 Drawing Sheets

Related U.S. Application Data which is a continuation of application No. PCT/US2019/013769, filed on Jan. 16, 2019, which is a continuation of application No. 16/201,542, filed on Nov. 27, 2018, now Pat. No. 10,314,762.

(60) Provisional application No. 62/767,260, filed on Nov. 14, 2018, provisional application No. 62/760,617, filed on Nov. 13, 2018, provisional application No. 62/759,968, filed on Nov. 12, 2018.

(52) U.S. Cl.
CPC .  *A61H 23/0254* (2013.01); *A61H 2201/0153* (2013.01); *A61H 2201/0157* (2013.01); *A61H 2201/1436* (2013.01); *A61H 2201/5002* (2013.01); *A61H 2201/5043* (2013.01); *A61H 2201/5058* (2013.01); *A61H 2201/5071* (2013.01); *A61H 2201/5097* (2013.01)

(56) References Cited

U.S. PATENT DOCUMENTS

| | | | |
|---|---|---|---|
| 3,968,789 A | 7/1976 | Simoncini | |
| 4,088,128 A * | 5/1978 | Mabuchi | A61H 23/0254 601/108 |
| 4,513,737 A | 4/1985 | Mabuchi | |
| 4,549,535 A | 10/1985 | Wing | |
| 4,566,442 A | 1/1986 | Mabuchi et al. | |
| 4,691,693 A | 9/1987 | Sato | |
| 4,698,869 A | 10/1987 | Mierau et al. | |
| 4,790,296 A | 12/1988 | Segal | |
| 4,841,955 A * | 6/1989 | Evans | A61H 23/0218 601/108 |
| 4,989,613 A | 2/1991 | Finkenberg | |
| D329,291 S | 9/1992 | Wollman | |
| D329,292 S | 9/1992 | Wollman | |
| D331,467 S | 12/1992 | Wollman | |
| 5,656,017 A | 8/1997 | Keller et al. | |
| D388,175 S | 12/1997 | Lie | |
| 5,733,029 A | 3/1998 | Monroe | |
| 5,769,657 A | 6/1998 | Kondo et al. | |
| 5,925,002 A | 7/1999 | Wollman | |
| 5,935,089 A | 8/1999 | Shimizu | |
| D430,938 S | 9/2000 | Lee | |
| D448,852 S | 10/2001 | Engelen | |
| 6,401,289 B1 | 6/2002 | Herbert | |
| D476,746 S | 7/2003 | Harris et al. | |
| 6,616,621 B1 * | 9/2003 | Kohr | A61H 23/0254 601/72 |
| 6,682,496 B1 | 1/2004 | Pivaroff | |
| D531,733 S | 11/2006 | Burout, III et al. | |
| D553,252 S | 10/2007 | Masuda | |
| D606,192 S | 12/2009 | Summerer et al. | |
| D649,657 S | 11/2011 | Petersen et al. | |
| D658,759 S | 5/2012 | Marescaux et al. | |
| 8,435,194 B2 | 5/2013 | Dverin et al. | |
| D703,337 S | 4/2014 | Fuhr et al. | |
| D706,433 S | 6/2014 | Fuhr et al. | |
| D708,742 S | 7/2014 | Dallemagne et al. | |
| D734,863 S | 7/2015 | Hennessey | |
| D735,348 S | 7/2015 | Hennessey | |
| D759,237 S | 6/2016 | Heath et al. | |
| D759,238 S | 6/2016 | Heath et al. | |
| D763,442 S | 8/2016 | Price et al. | |
| D778,439 S | 2/2017 | Hakansson et al. | |
| 9,889,066 B2 | 2/2018 | Danby et al. | |
| D819,221 S | 5/2018 | Lei | |
| D823,478 S | 7/2018 | Park | |
| D837,395 S | 1/2019 | Gan | |
| D838,378 S | 1/2019 | Cao | |
| D840,547 S | 2/2019 | Harle et al. | |
| 10,201,470 B2 | 2/2019 | Griner | |
| D842,491 S | 3/2019 | Fleming et al. | |
| D843,656 S | 3/2019 | Zhang et al. | |
| D844,896 S | 4/2019 | Levi et al. | |
| D847,362 S | 4/2019 | Tang | |
| D847,364 S | 4/2019 | Lee et al. | |
| D847,990 S | 5/2019 | Kimball | |
| 10,314,762 B1 | 6/2019 | Marton et al. | |
| 10,357,425 B2 | 7/2019 | Wersland et al. | |
| D855,822 S | 8/2019 | Marton et al. | |
| D890,942 S | 7/2020 | Wersland et al. | |
| D890,943 S | 7/2020 | Wersland et al. | |
| D896,393 S | 9/2020 | Wersland et al. | |
| 10,847,984 B2 | 11/2020 | Solana et al. | |
| 10,857,064 B2 | 12/2020 | Wersland et al. | |
| 2002/0177795 A1 | 11/2002 | Frye | |
| 2002/0188233 A1 | 12/2002 | Denyes | |
| 2003/0014079 A1 | 1/2003 | Tucek | |
| 2003/0195443 A1 | 10/2003 | Miller | |
| 2005/0131461 A1 | 6/2005 | Tucek et al. | |
| 2006/0116614 A1 | 6/2006 | Jones et al. | |
| 2006/0211961 A1 | 9/2006 | Meyer et al. | |
| 2008/0262399 A1 | 10/2008 | Kovelman et al. | |
| 2008/0275371 A1 | 11/2008 | Hoffmann | |
| 2009/0270915 A1 | 10/2009 | Tsai et al. | |
| 2010/0145242 A1 | 6/2010 | Tsai | |
| 2010/0160841 A1 | 6/2010 | Wu | |
| 2010/0274162 A1 | 10/2010 | Evans | |
| 2012/0197357 A1 | 8/2012 | Dewey et al. | |
| 2013/0030506 A1 | 1/2013 | Bartolone et al. | |
| 2013/0261516 A1 | 10/2013 | Cilea et al. | |
| 2013/0281897 A1 | 10/2013 | Hoffmann et al. | |
| 2014/0031866 A1 * | 1/2014 | Fuhr | A61H 1/008 606/239 |
| 2014/0221887 A1 | 8/2014 | Wu | |
| 2015/0005682 A1 | 1/2015 | Danby et al. | |
| 2015/0119771 A1 | 4/2015 | Roberts | |
| 2015/0366746 A1 | 12/2015 | Ashby | |
| 2016/0367425 A1 | 12/2016 | Wersland | |
| 2017/0027798 A1 | 2/2017 | Wersland | |
| 2017/0333280 A1 * | 11/2017 | Black | A61H 7/005 |
| 2018/0008512 A1 | 1/2018 | Goldstein | |
| 2018/0154141 A1 | 6/2018 | Ahn | |
| 2018/0168913 A1 | 6/2018 | Sedic | |
| 2018/0200141 A1 | 7/2018 | Wersland et al. | |
| 2019/0175434 A1 | 6/2019 | Zhang | |
| 2019/0209424 A1 | 7/2019 | Wersland et al. | |
| 2019/0254921 A1 | 8/2019 | Marton et al. | |
| 2019/0254922 A1 | 8/2019 | Marton et al. | |
| 2020/0069510 A1 | 3/2020 | Wersland et al. | |
| 2020/0222263 A1 | 7/2020 | Wersland et al. | |
| 2020/0261310 A1 | 8/2020 | Wersland et al. | |
| 2020/0274162 A1 | 8/2020 | Galceran Mestres et al. | |
| 2020/0289365 A1 | 9/2020 | Wersland et al. | |
| 2020/0352820 A1 | 11/2020 | Nazarian et al. | |
| 2020/0352821 A1 | 11/2020 | Wersland et al. | |
| 2021/0022955 A1 | 1/2021 | Wersland et al. | |

FOREIGN PATENT DOCUMENTS

| | | |
|---|---|---|
| CA | 188553 A | 2/1919 |
| CN | 111759711 A | 10/2020 |
| EP | 0158870 A1 | 10/1985 |
| EP | 1728494 A1 | 12/2006 |
| EP | 3235484 A1 | 10/2017 |
| EP | 3320888 A1 | 5/2018 |
| EP | 3435381 A1 | 1/2019 |
| JP | H0733329 B2 | 6/1995 |
| JP | 2781408 B2 | 7/1998 |
| JP | 2999872 B2 | 1/2000 |
| JP | 3813828 B2 | 8/2006 |
| WO | WO-2020/101725 A1 | 5/2020 |
| WO | WO-2020/227225 A1 | 11/2020 |
| WO | WO-2020/227230 A1 | 11/2020 |
| WO | WO-2020/227569 A1 | 11/2020 |

OTHER PUBLICATIONS

Extended European Search Report for European Application No. 19190396.2, Apr. 1, 2020, 8 pages.

(56) References Cited

OTHER PUBLICATIONS

Han, Inho, Authorized Officer of ISA_KR, International Search Report and Written Opinion of the International Searching Authority, Aug. 9, 2019, 13 pages.
Japanese Patent Office, Notification of Reasons for Refusal for Japanese Application No. 2019-114726, Sep. 3, 2019, 6 pages {including translation).
Rachel [family name unknown], "Jigsaw Massager," Aug. 28, 2007, 7 pages, Information available online from http://www.instructables.com/id/Jigsaw-Massager/.
International Preliminary Report on Patentability and Written Opinion of International Application No. PCT/US2021/057033 dated May 11, 2023, 9 pages.
International Search Report and Written Opinion of PCT/US2021/057033 dated Feb. 16, 2022, 14 pages.
International Preliminary Report on Patentability of International Application No. PCT/US2021/041073 dated Jan. 10, 2023, 10 pages.

* cited by examiner

SYSTEM AND PROCESS FOR DETERMINING PRESSURE SETTINGS FOR A PERCUSSIVE MASSAGE APPLICATOR

CROSS-REFERENCE TO RELATED APPLICATIONS

This application is a continuation-in-part of U.S. patent application Ser. No. 16/887,383 filed on May 29, 2020, which is a continuation of International Application No. PCT/US2019/013769 filed on Jan. 16, 2019, which claims the benefit of priority of U.S. patent application Ser. No. 16/201,542 filed on Nov. 27, 2018 (now U.S. Pat. No. 10,314,762). International Application No. PCT/US2019/013769 claims the benefit of priority of U.S. Provisional Application No. 62/759,968 filed on Nov. 12, 2018, U.S. Provisional Application No. 62/760,617 filed on Nov. 13, 2018, and U.S. Provisional Application No. 62/767,260 filed on Nov. 14, 2018. U.S. patent application Ser. No. 16/201,542 also claims the benefit of priority of U.S. Provisional Application No. 62/759,968 filed on Nov. 12, 2018, U.S. Provisional Application No. 62/760,617 filed on Nov. 13, 2018, and U.S. Provisional Application No. 62/767,260 filed on Nov. 14, 2018. All foregoing priority applications are incorporated herein by reference in their entireties.

FIELD

The present disclosure is related to the field of therapeutic devices, and, more particularly, is related the field of devices that apply percussive massage to selected portions of a body.

BACKGROUND

Percussive massage, which is also referred to as tapotement, is the rapid, percussive tapping, slapping and cupping of an area of the human body. Percussive massage is used to more aggressively work and strengthen deep-tissue muscles. Percussive massage increases local blood circulation and can even help tone muscle areas. Percussive massage may be applied by a skilled massage therapist using rapid hand movements; however, the manual force applied to the body varies, and the massage therapist may tire before completing a sufficient treatment regime.

Percussive massage may also be applied by electromechanical percussive massage devices (percussive applicators), which are commercially available. Such percussive applicators may include, for example, an electric motor coupled to drive a reciprocating piston within a cylinder. A variety of percussive heads may be attached to the piston to provide different percussive effects on selected areas of the body. Many of the known percussive applicators are expensive, large, relatively heavy, and tethered to an electrical power source. For example, some percussive applicators may require users to grip the applicators with both hands in order to control the applicators. Some percussive applicators are relatively noisy because of the conventional mechanisms used to convert the rotational energy of an electric motor to the reciprocating motion of the piston.

When a percussive massage device is applied to a body of a human, the efficacy of the therapy provided by the percussive massage device depends in part on the pressure applied to the body. For certain persons, a lower pressure provides a relaxing massage and a higher pressure may be uncomfortable. For other persons, a higher pressure is required to provide relief from sore muscles and other tissues. For many persons, the pressure needs to be varied from location to location on their bodies. Presently available percussive massage devices do not provide a way to determine the pressure applied to a body. Thus, achievement of a correct pressure for a particular location on the body of a specific person relies on the skill and the memory of the massage therapist applying a percussive massager. Even with the same percussive massage equipment, the same therapist is not likely to provide the appropriate pressures during two successive treatment.

The foregoing examples of the related art and limitations therewith are intended to be illustrative and not exclusive, and are not admitted to be "prior art." Other limitations of the related art will become apparent to those of skill in the art upon a reading of the specification and a study of the drawings.

SUMMARY

System and process for determining pressure settings for a percussive massage applicator are described. According to one embodiment, A method includes obtaining a first value for a parameter of a motor of the applicator when the applicator has no load; and obtaining a second value for the parameter of the motor when the applicator has a load. The method can include determining a difference value between the first value and the second value; comparing the difference value to two or more predetermined ranges of values that correspond to a pressure level of the applicator; and selecting the predetermined range that comprises the difference value, thereby determining the pressure level of the applicator.

The above and other preferred features, including various novel details of implementation and combination of events, will now be more particularly described with reference to the accompanying figures and pointed out in the claims. It will be understood that the particular systems and methods described herein are shown by way of illustration only and not as limitations. As will be understood by those skilled in the art, the principles and features described herein may be employed in various and numerous embodiments without departing from the scope of any of the present inventions. As can be appreciated from foregoing and following description, each and every feature described herein, and each and every combination of two or more such features, is included within the scope of the present disclosure provided that the features included in such a combination are not mutually inconsistent. In addition, any feature or combination of features may be specifically excluded from any embodiment of any of the present inventions.

The foregoing Summary, including the description of some embodiments, motivations therefor, and/or advantages thereof, is intended to assist the reader in understanding the present disclosure, and does not in any way limit the scope of any of the claims.

BRIEF DESCRIPTION OF THE DRAWINGS

The accompanying figures, which are included as part of the present specification, illustrate the presently preferred embodiments and together with the generally description given above and the detailed description of the preferred embodiments given below serve to explain and teach the principles described herein.

1 showing the bottom, the left side and the distal end (the end facing away from a user (not shown)) of the applicator.

Figure 1:
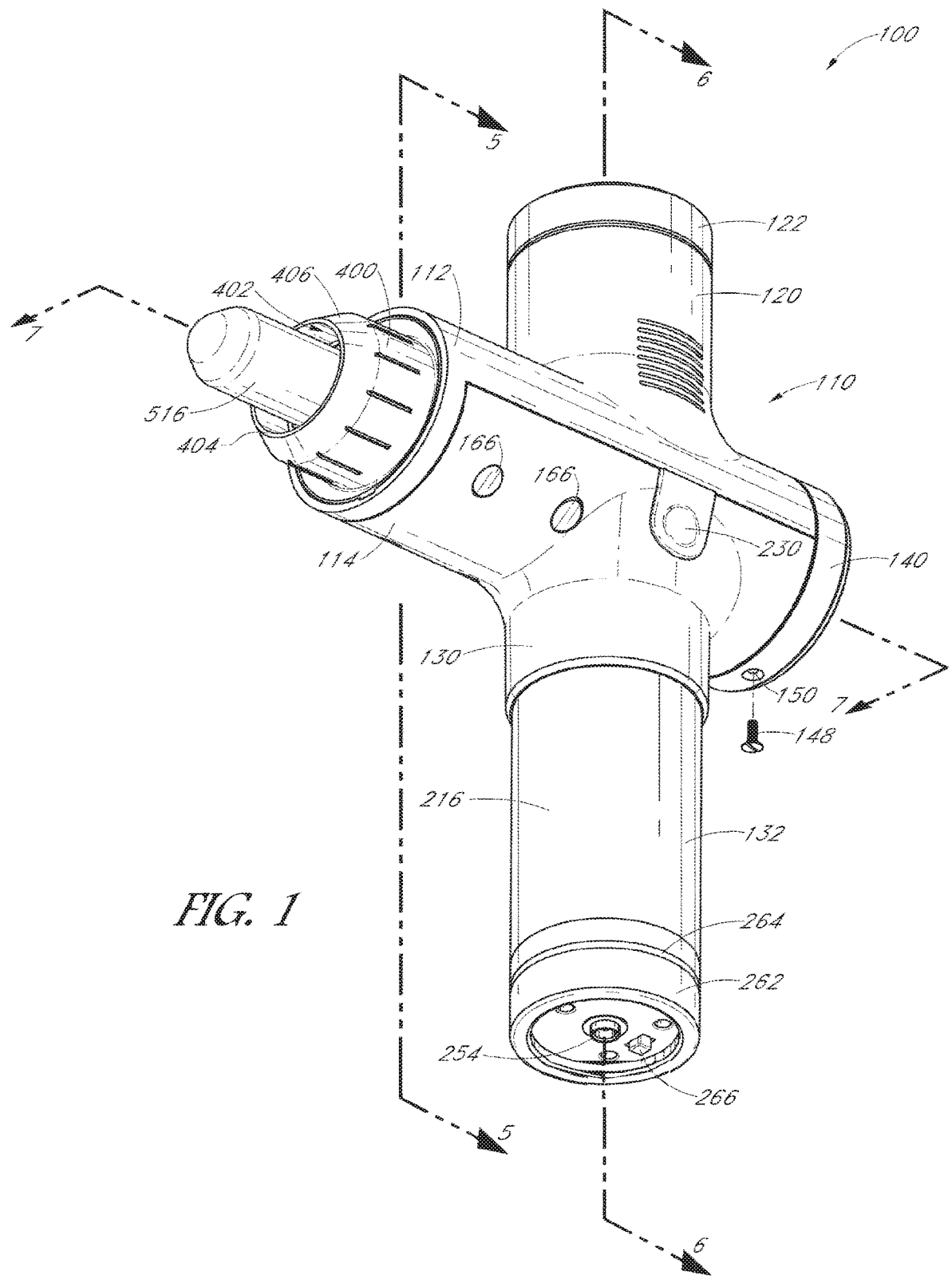
FIG. 1 illustrates a bottom perspective view of a portable electromechanical percussive massage applicator that is battery powered and has a single hand grip, the view in FIG.
Figure 2:
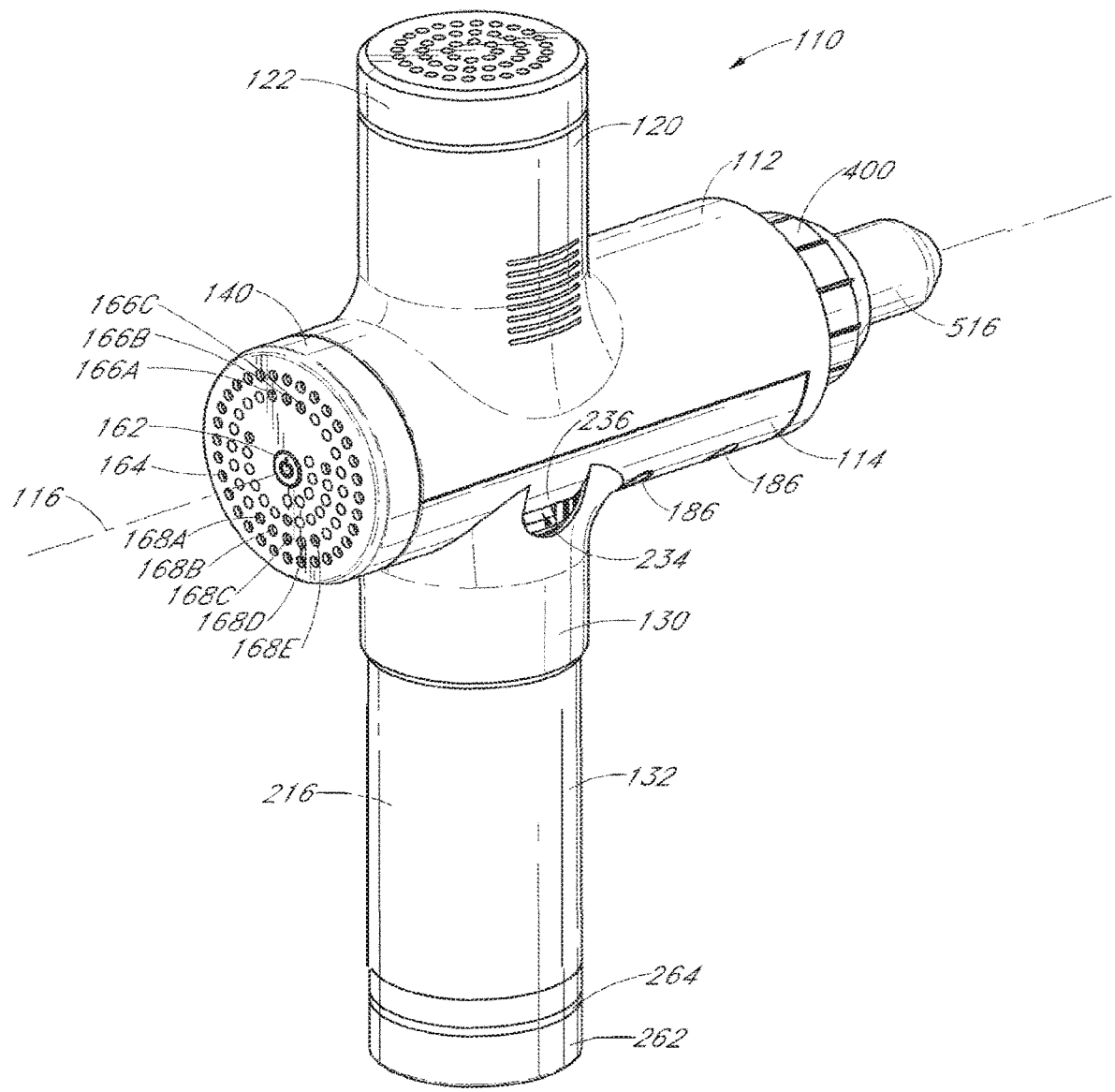

FIG. 2 illustrates a top perspective view of the portable electromechanical percussive massage applicator of FIG. 1 showing the top, the right side and the proximal end (the end closest to a user (not shown)) of the applicator.

Figure 3:
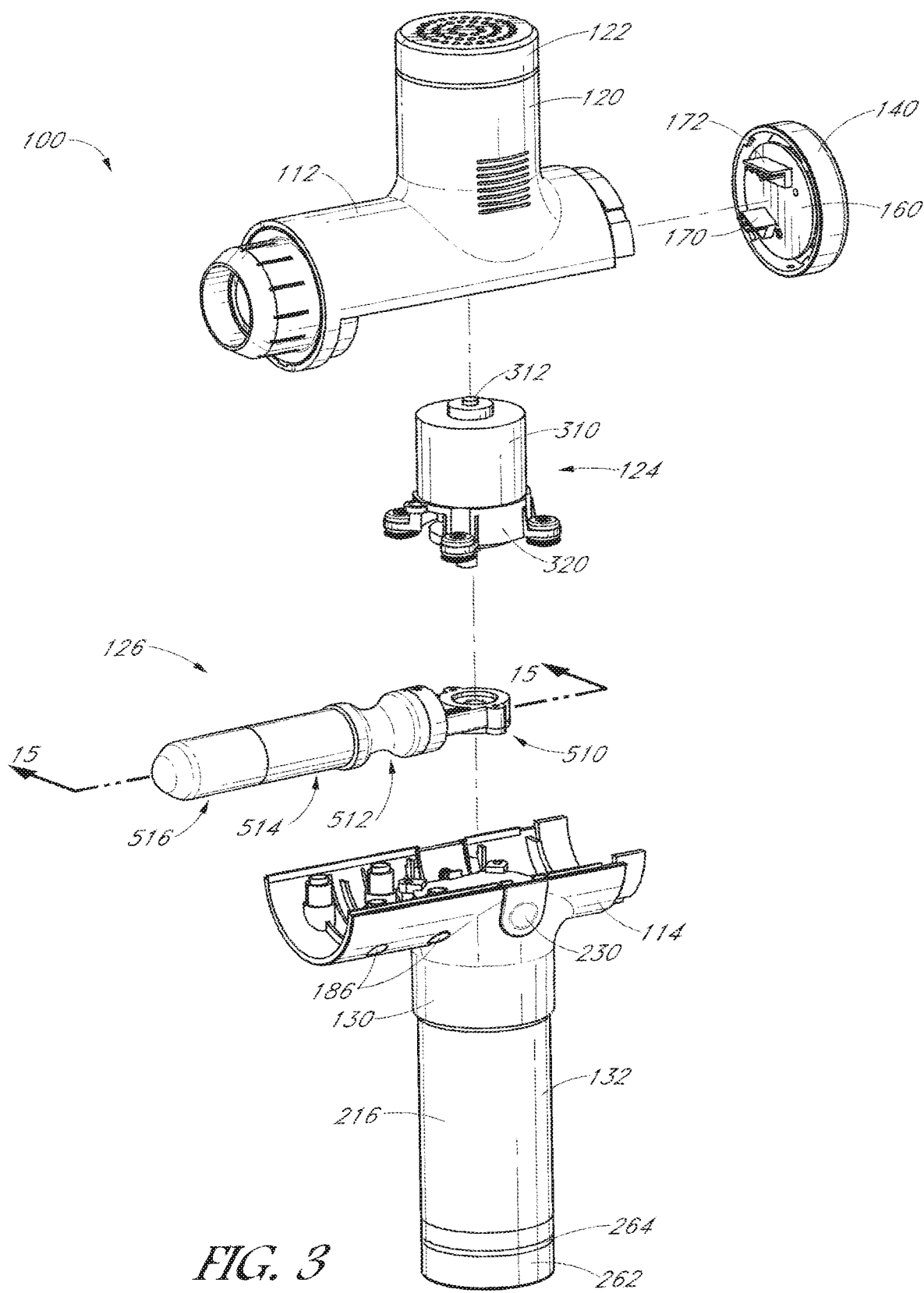

FIG. 3 illustrates an exploded perspective view of the portable electromechanical percussive massage applicator of FIG. 1, the view showing the upper housing, a motor assembly, a reciprocation assembly, and a lower housing with an attached battery assembly.

Figure 4A:
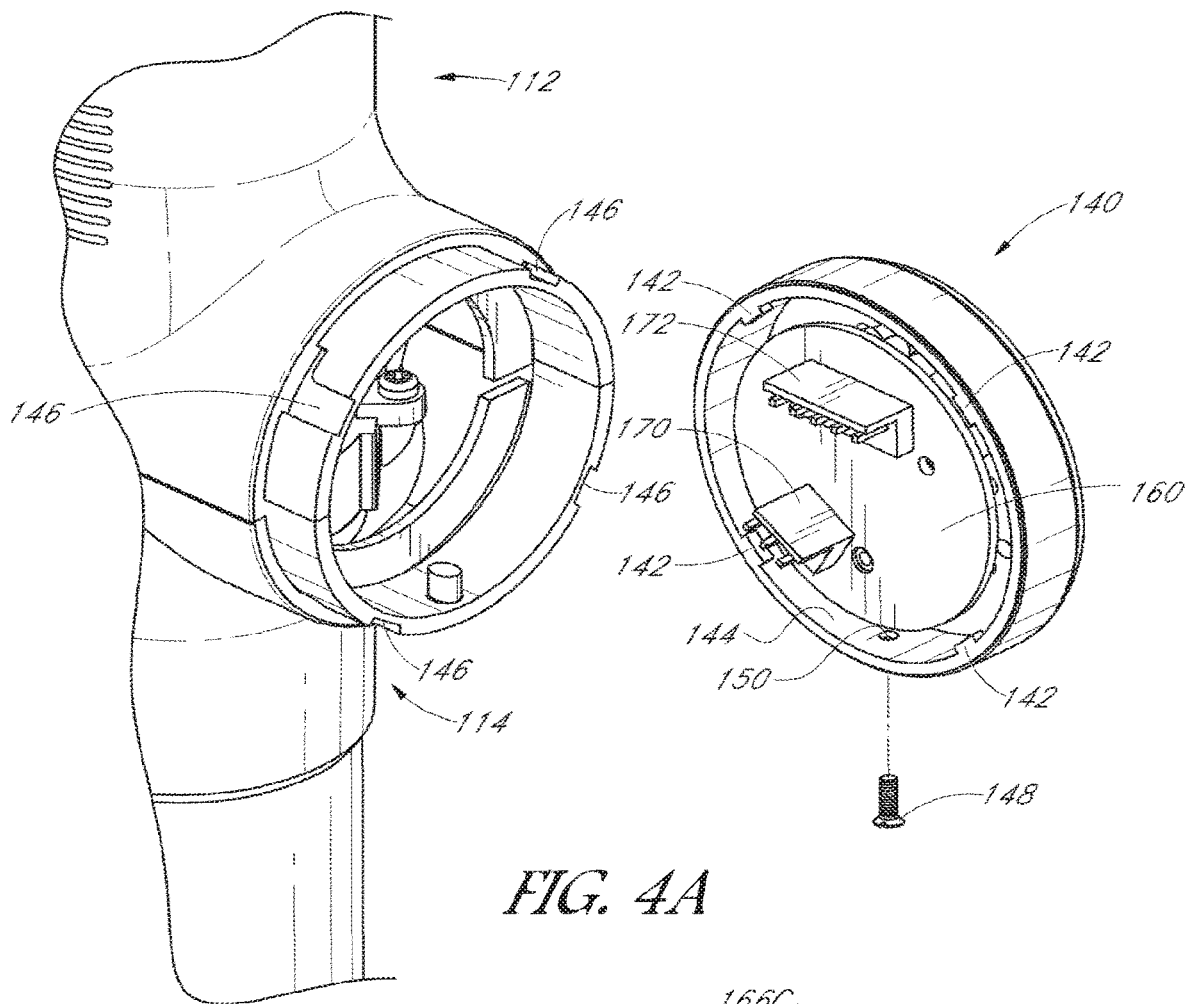

FIG. 4A illustrates an enlarged proximal end view of the combined upper and lower housing with the endcap of the housing detached and rotated to show the interlocking features, the view further showing a distal view of the main printed circuit board (PCB) positioned within the endcap of the housing.

Figure 4B:
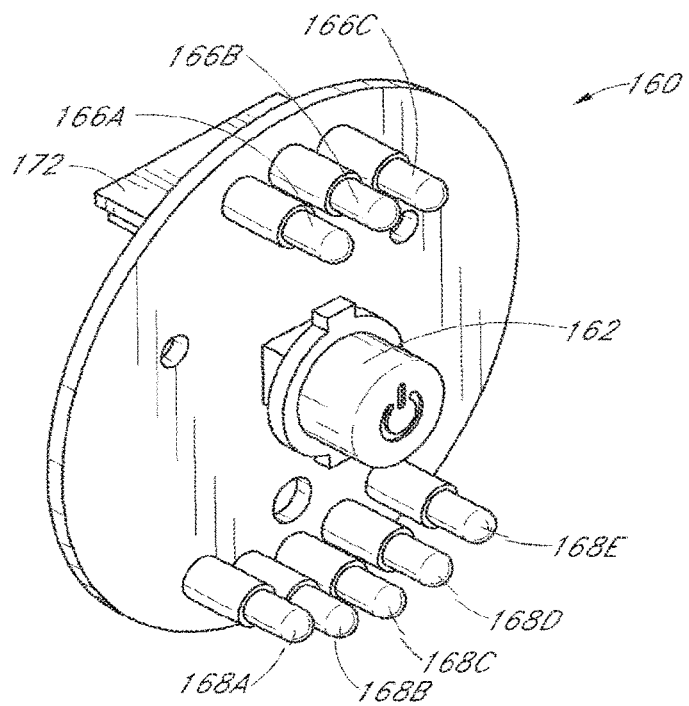

FIG. 4B illustrates a proximal view of the main PCB isolated from the endcap of the housing.

Figure 5:
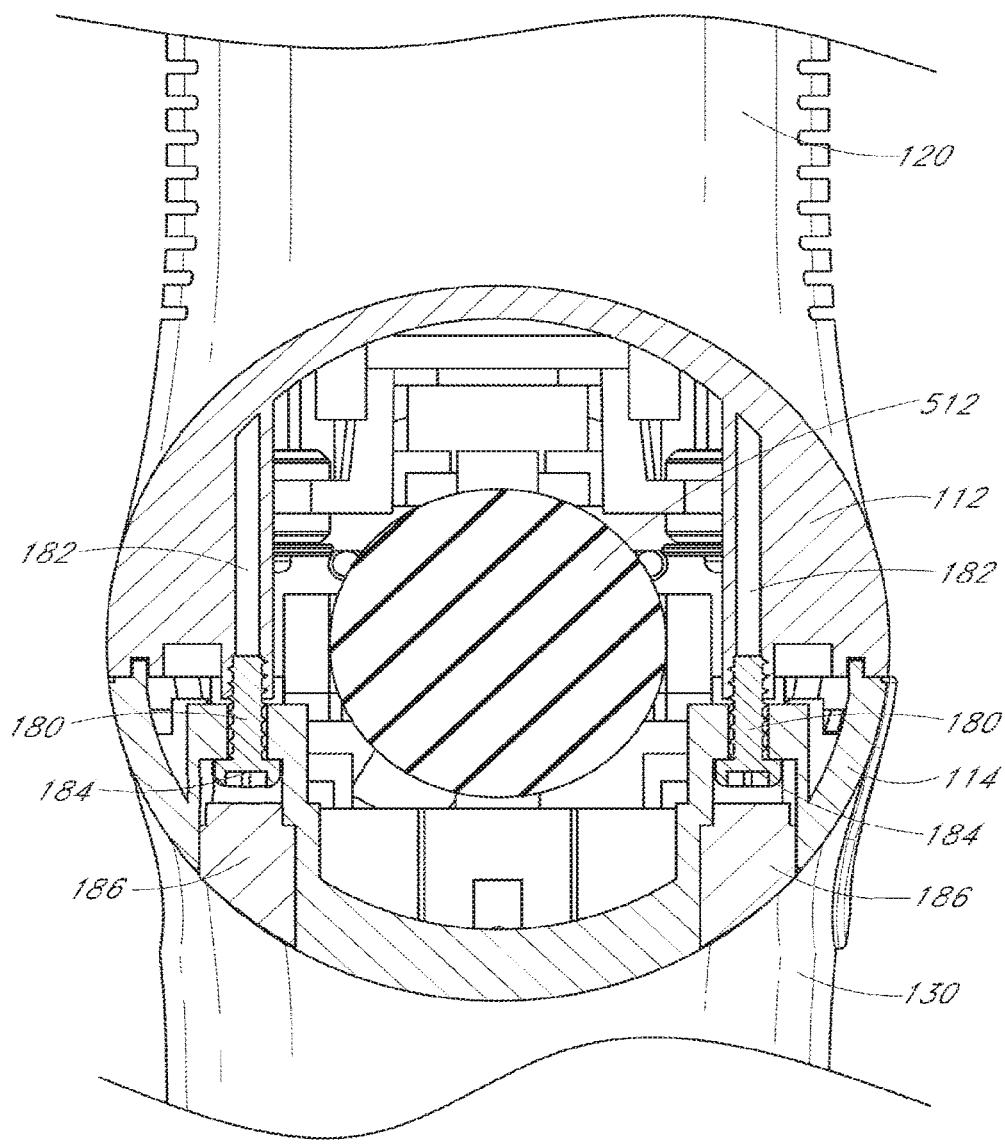

FIG. 5 illustrates an elevational cross-sectional view of the portable electromechanical percussive massage applicator of FIGS. 1 and 2 taken along the line 5-5 in FIG. 1, the view taken through a set of the mated interconnecting features of the upper and lower housings.

Figure 6:
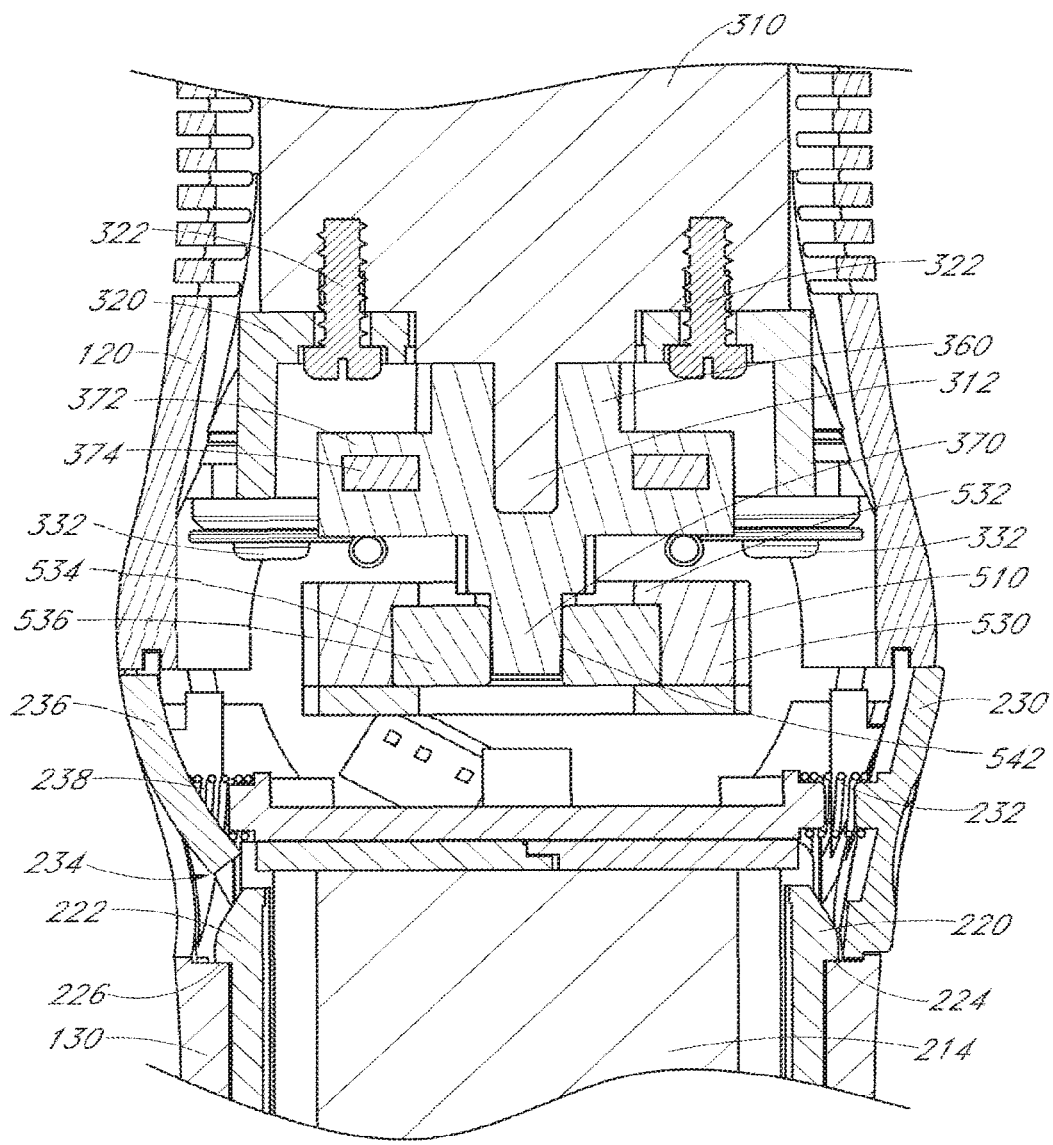

FIG. 6 illustrates an elevational cross-sectional view of the portable electromechanical percussive massage applicator of FIGS. 1 and 2 taken along the line 6-6 in FIG. 1, the view taken through the centerline of the shaft of the motor in the motor assembly of FIG. 3.

Figure 7:
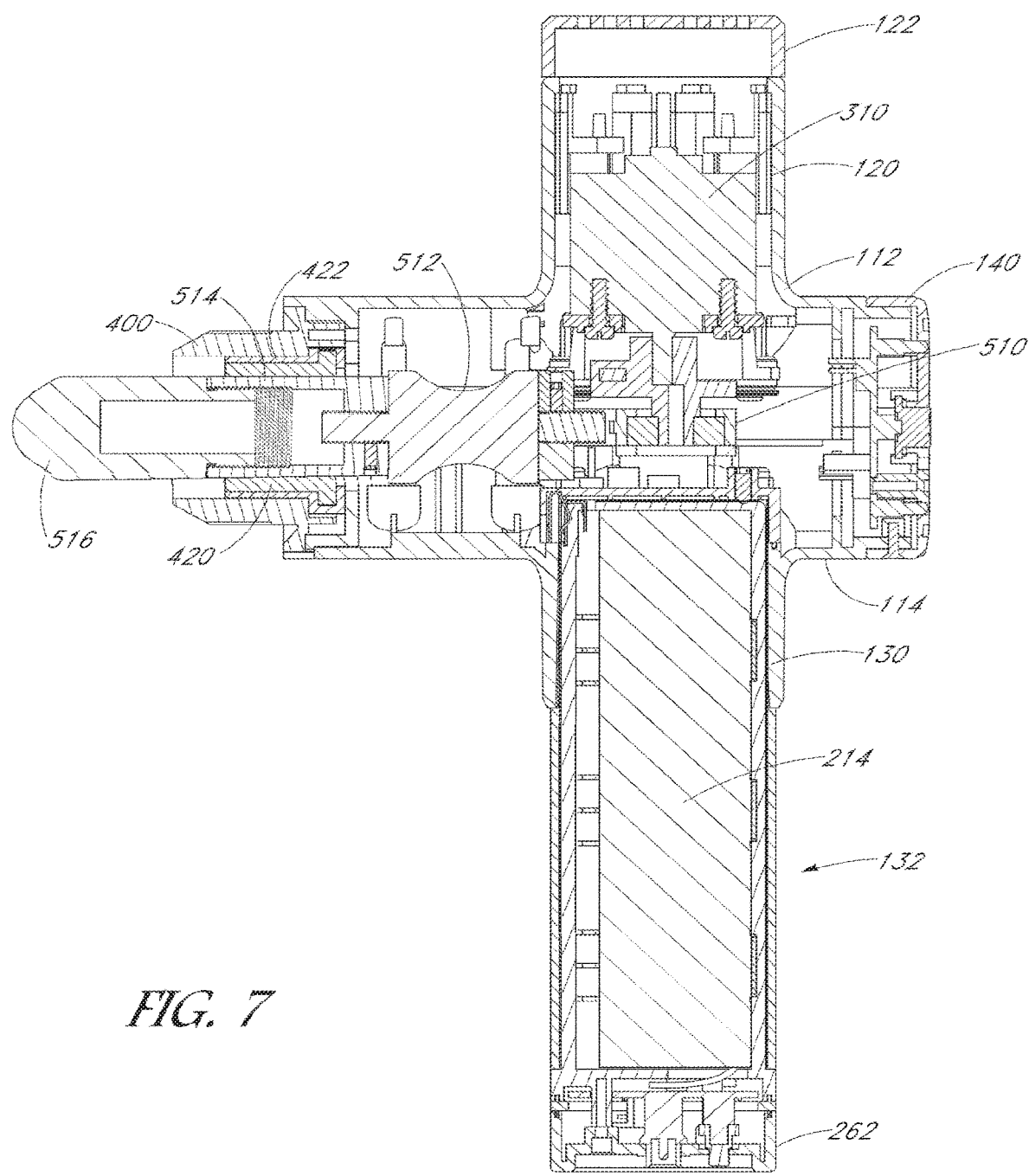

FIG. 7 illustrates an elevational cross-sectional view of the portable electromechanical percussive massage applicator of FIGS. 1 and 2 taken along the line 7-7 in FIG. 1, the view taken through the longitudinal centerline of the apparatus.

Figure 8:
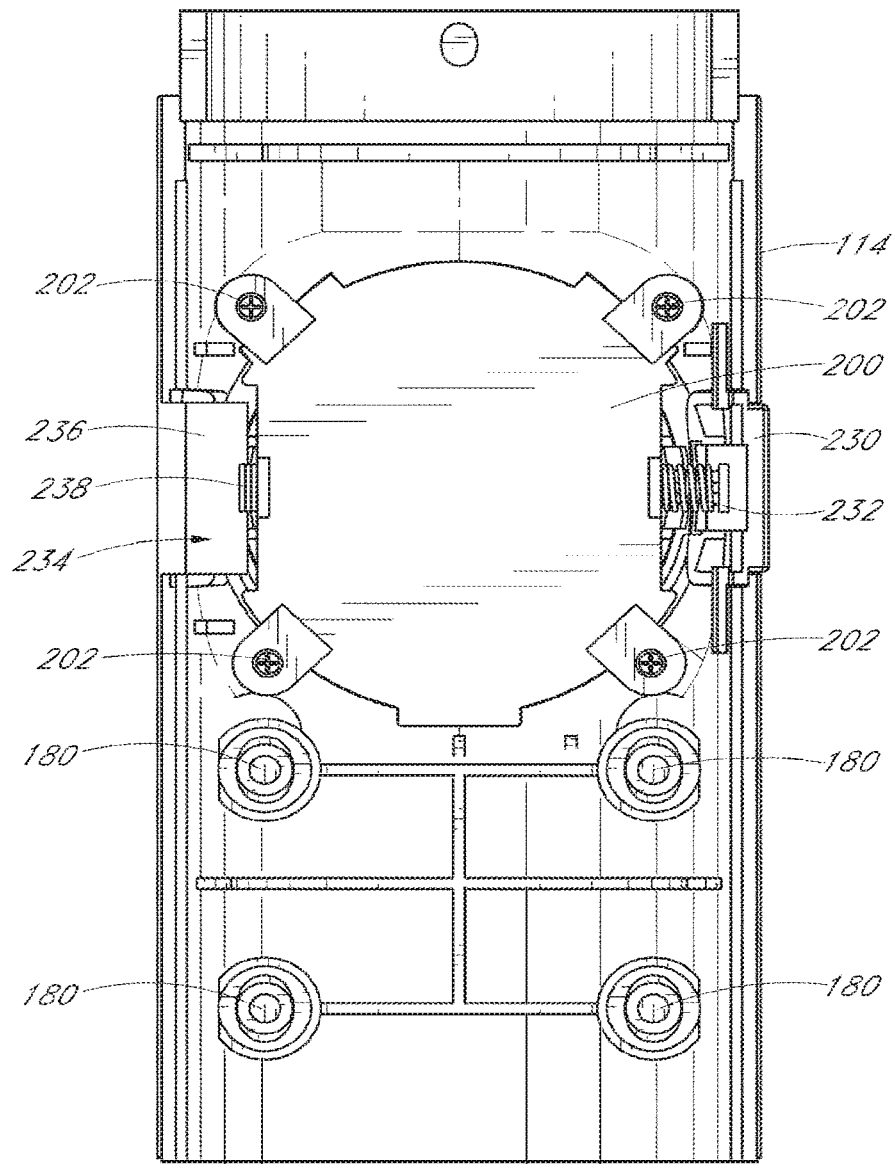

FIG. 8 illustrates a top plan view of the lower housing of FIG. 3.

Figure 9:
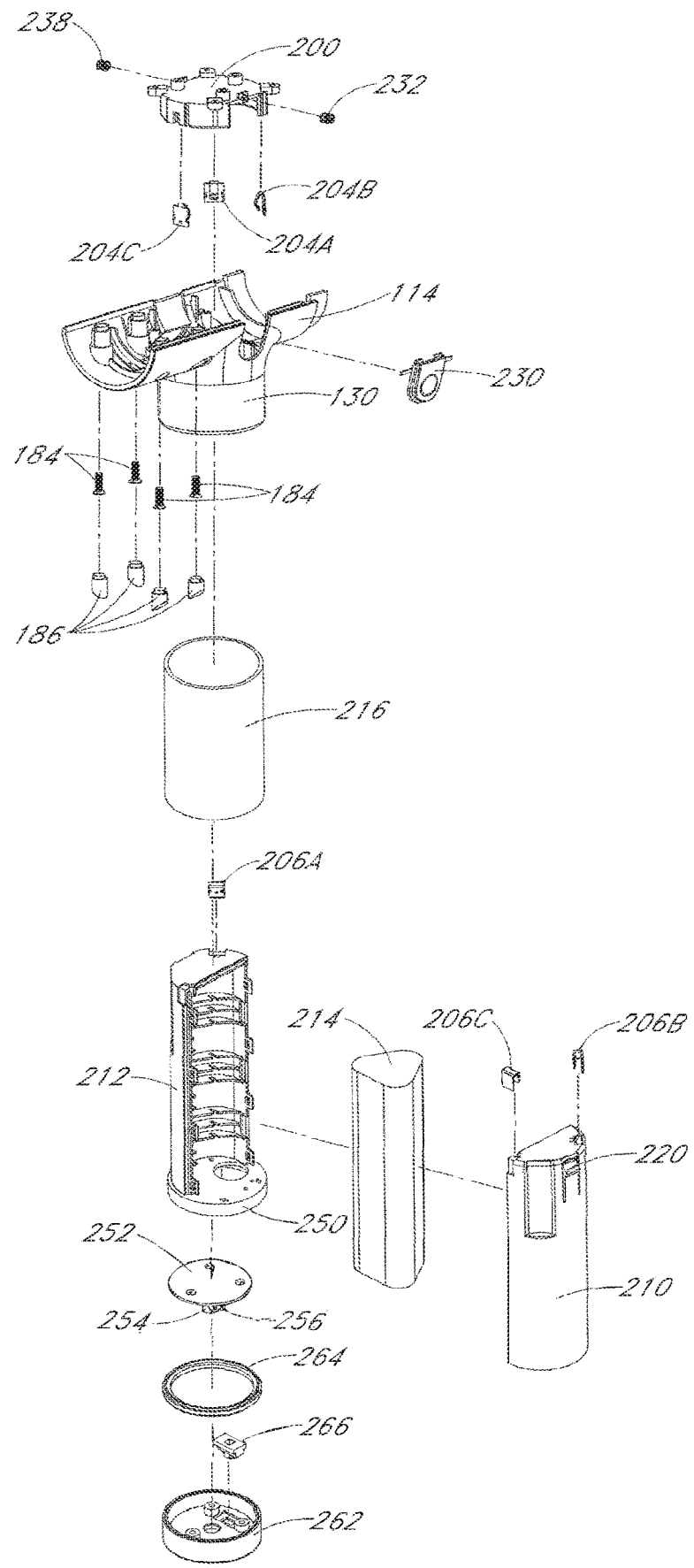

FIG. 9 illustrates an exploded perspective view of the lower housing and the battery assembly of FIG. 3.

Figure 10:
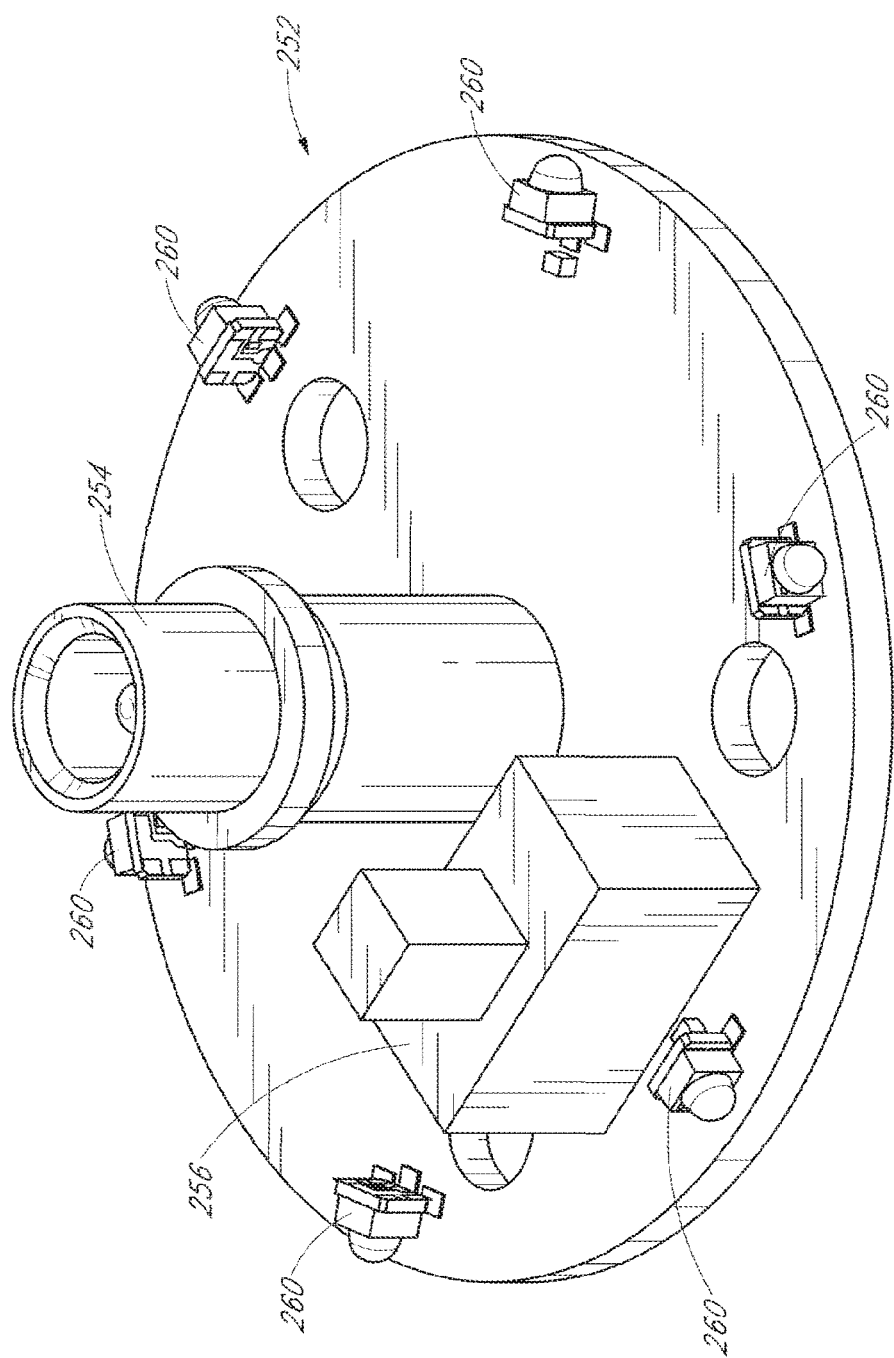

FIG. 10 illustrates an enlarged perspective view of the lower surface of the battery assembly printed circuit board.

Figure 11A:
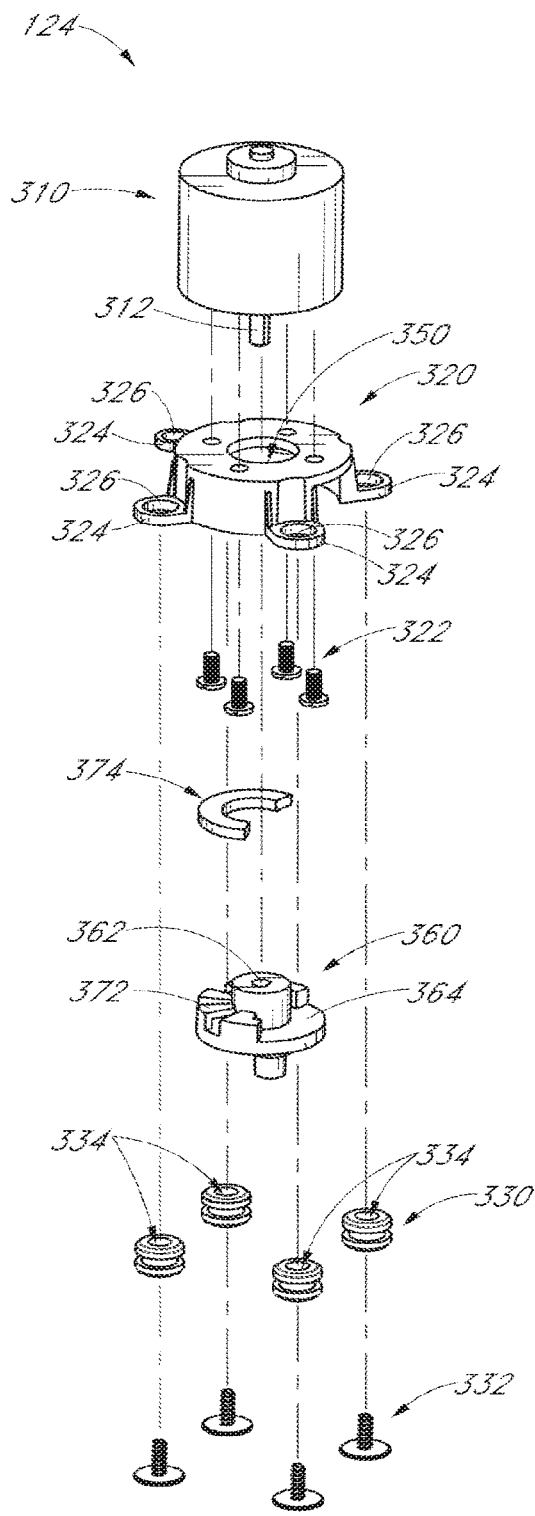

FIG. 11A illustrates an exploded top perspective view of the motor assembly of FIG. 3, the view showing the upper surfaces of the elements of the motor assembly.

Figure 11B:
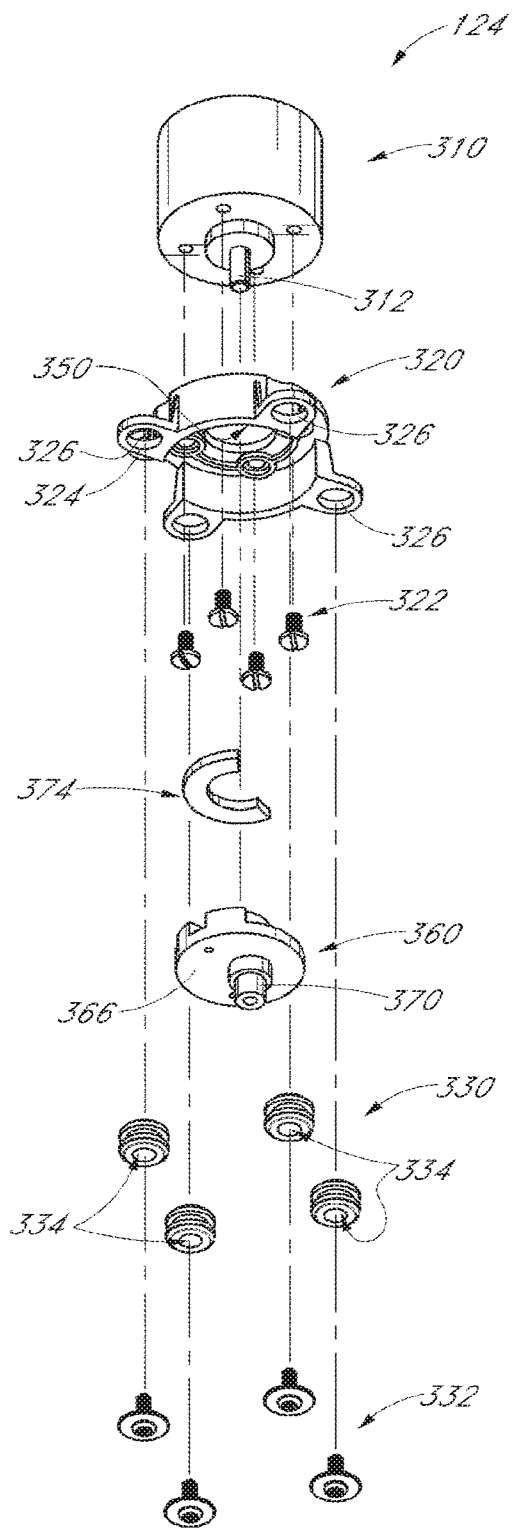

FIG. 11B illustrates an exploded bottom perspective view of the motor assembly of FIG. 3, the view of FIG. 11B similar to the view of FIG. 11A with the elements of the motor assembly rotated to show the lower surfaces of the elements.

Figure 12:
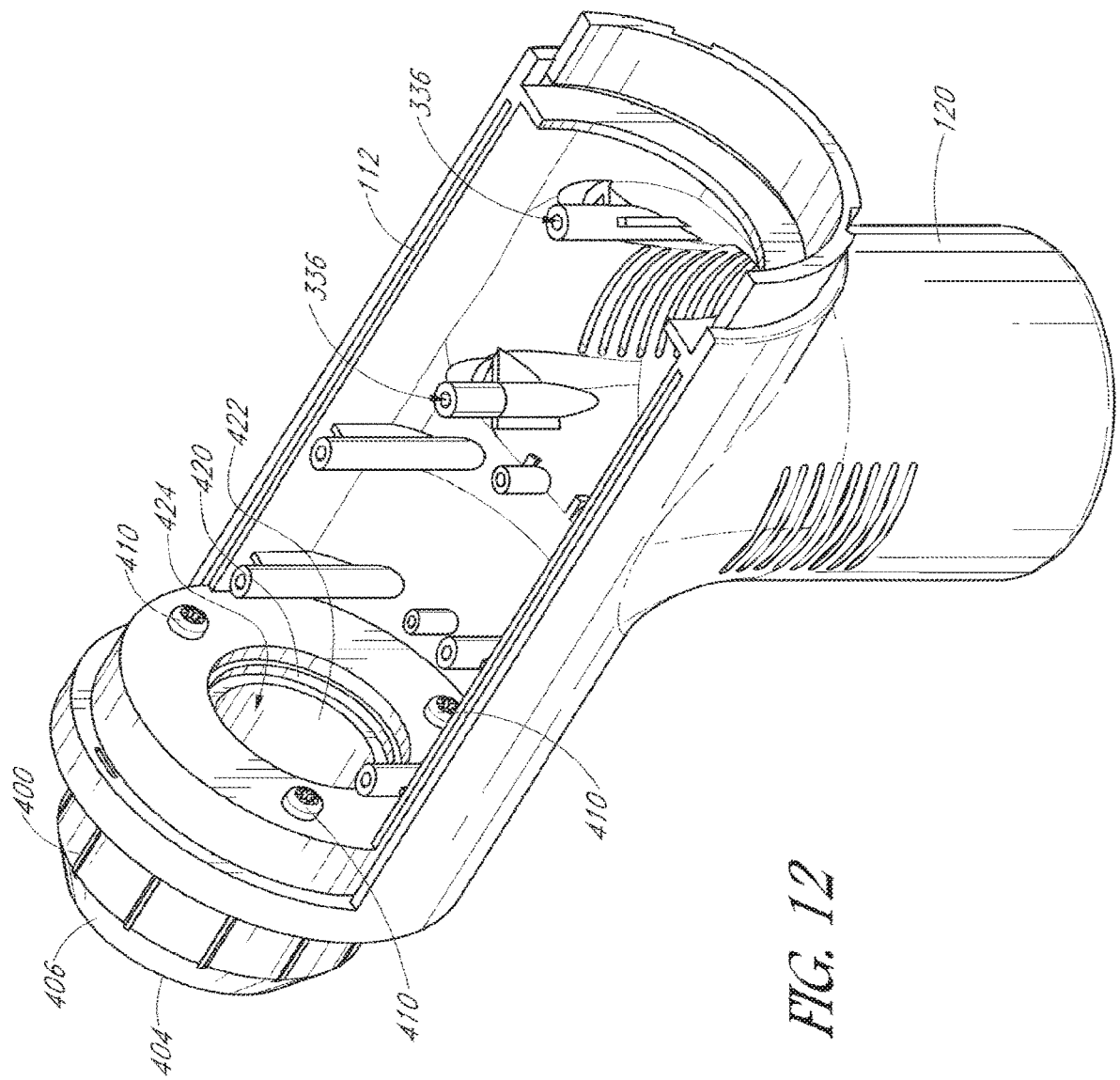

FIG. 12 illustrates a bottom perspective view of the upper housing of the percussive massage applicator viewed from the proximal end.

Figure 13:
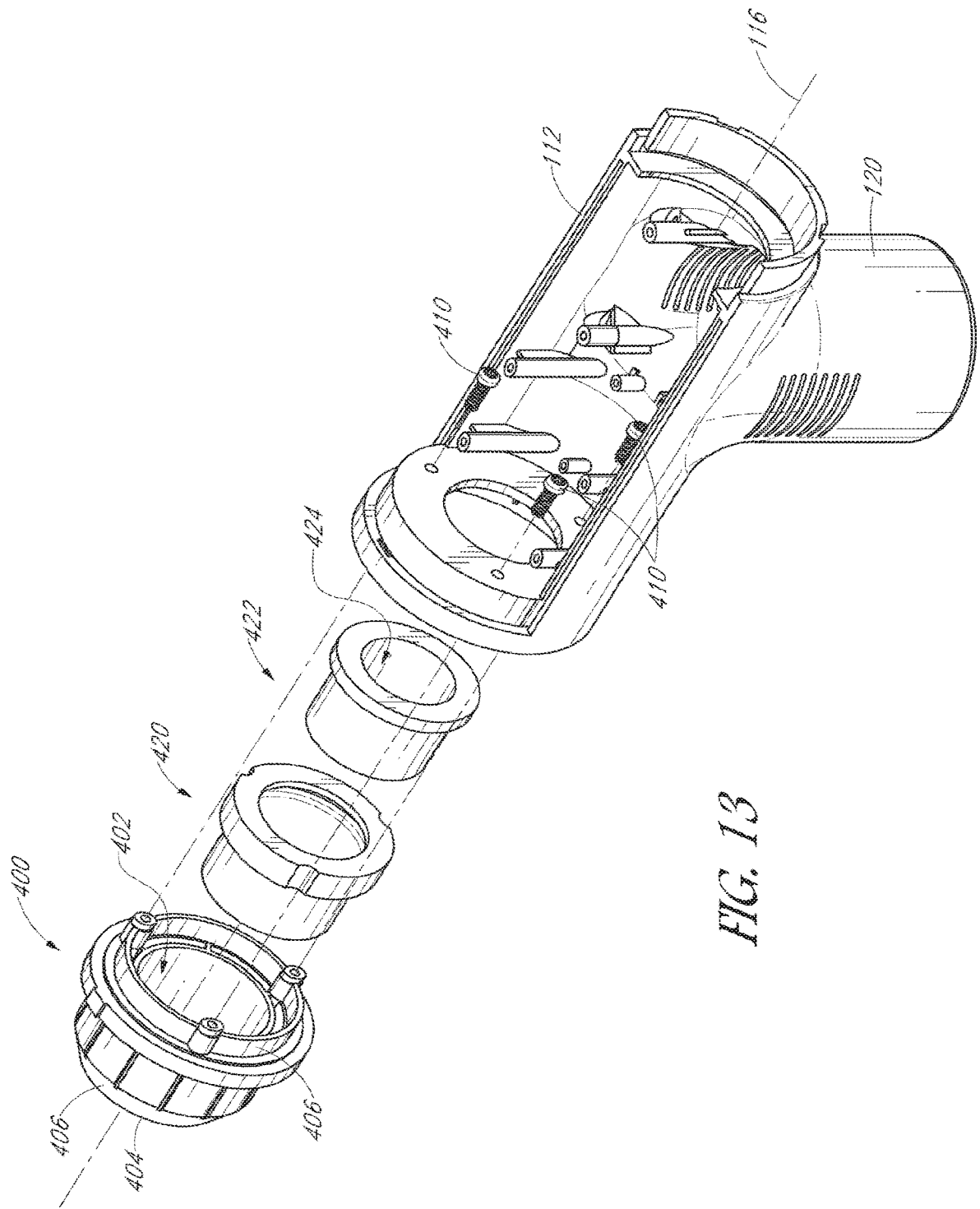

FIG. 13 illustrates an exploded perspective view of the upper housing of the percussive massage applicator corresponding to the view of FIG. 12 showing the outer sleeve, the cylindrical mounting sleeve and the cylinder body.

Figure 14:
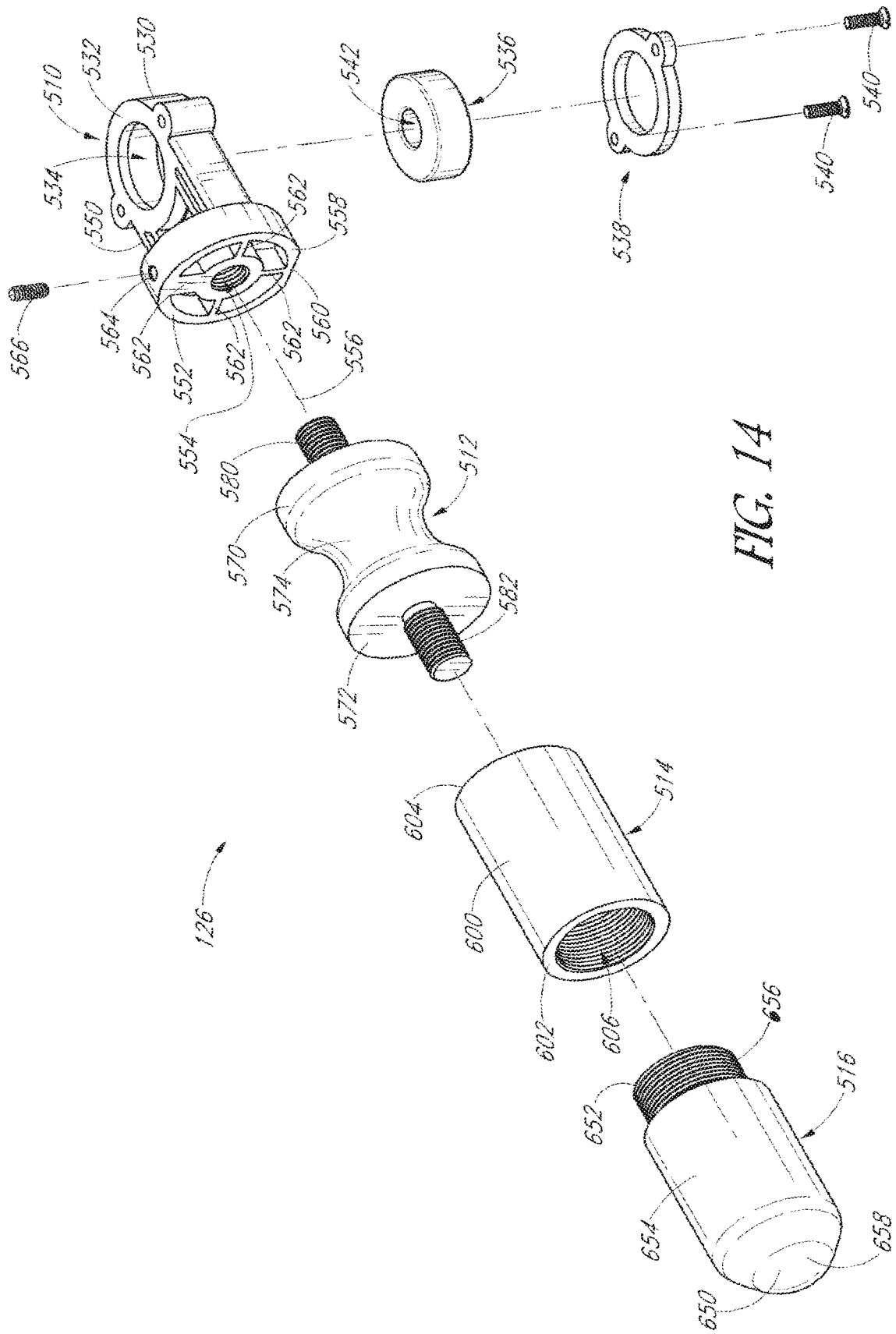

FIG. 14 illustrates an exploded perspective view of the reciprocation assembly of FIG. 3, the reciprocation assembly including a crank bracket, a flexible interconnection linkage, a piston and a removably attachable application head.

Figure 15:
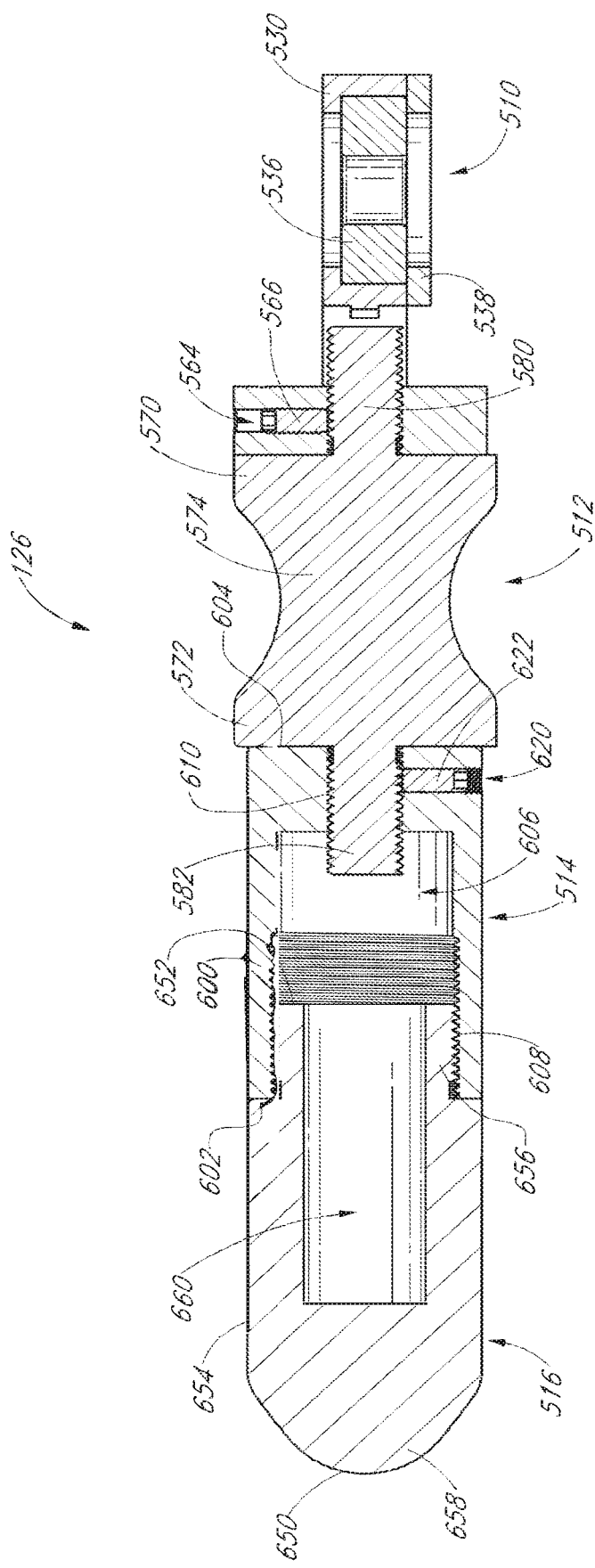

FIG. 15 illustrates a cross-sectional view of the assembled reciprocation assembly taken along the line 15-15 in FIG. 3.

Figure 16:
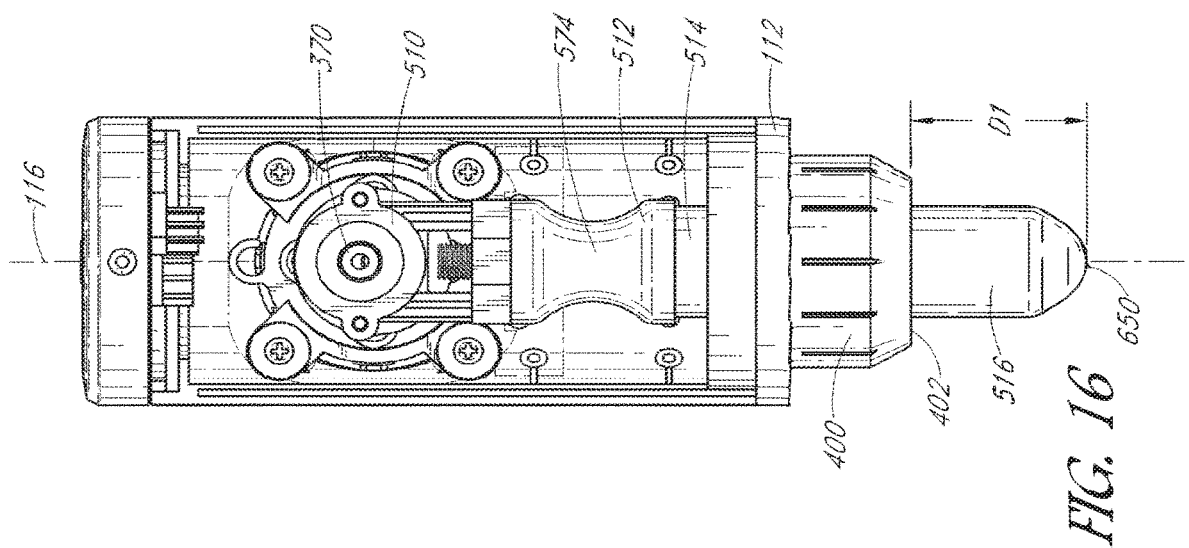

FIG. 16 illustrates a plan view of the percussive massage applicator of FIGS. 1 and 2 with the lower cover removed, the view looking upward toward the electrical motor of the applicator, the view in FIG. 16 showing the crank in the 12 o'clock position (as viewed in FIG. 16) such the end of the applicator head is extended a first distance from the housing of the applicator.

Figure 17:
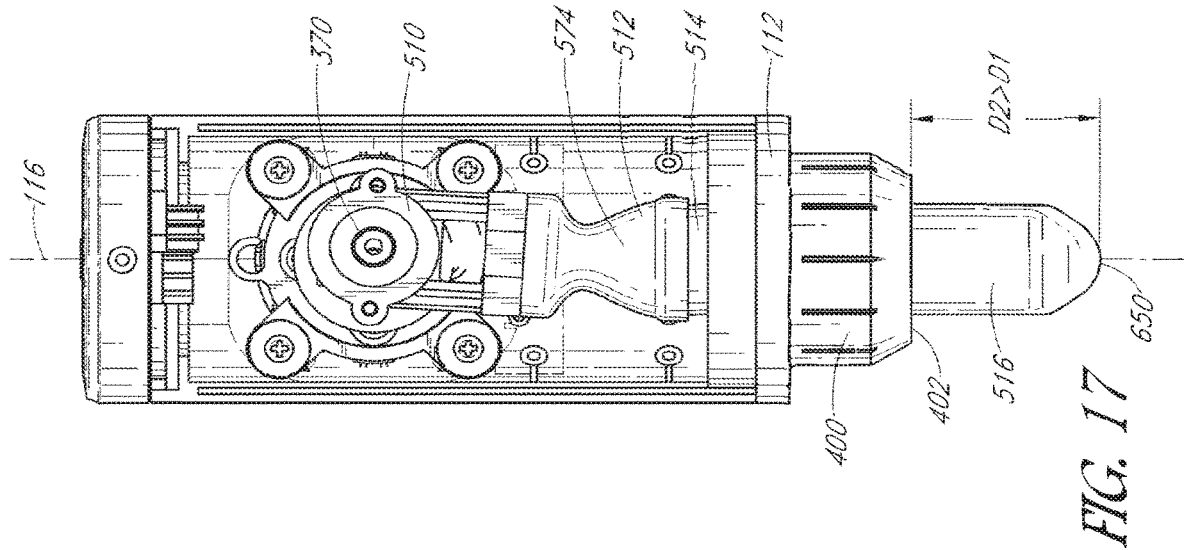

FIG. 17 illustrates a plan view of the portable electromechanical percussive massage applicator similar to the view of FIG. 16, the view in FIG. 17 showing the crank in the 3 o'clock position (as viewed in FIG. 17) such the applicator head is extended a second distance from the housing of the applicator, wherein the second distance is greater than the first distance of FIG. 16.

Figure 18:
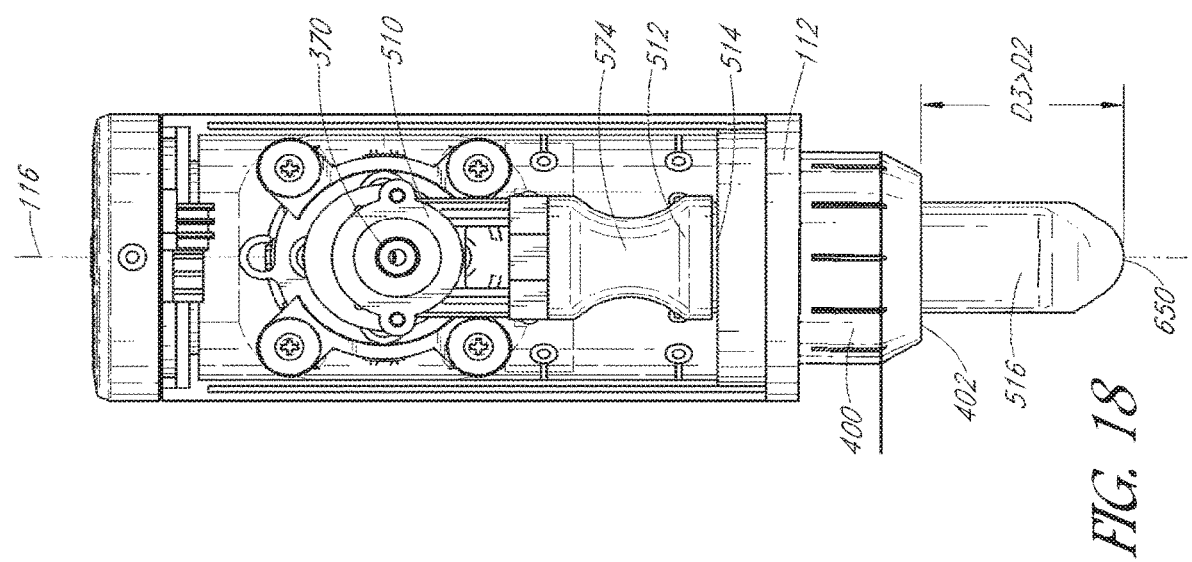

FIG. 18 illustrates a plan view of the portable electromechanical percussive massage applicator similar to the views of FIGS. 16 and 17, the view in FIG. 18 showing the crank in the 6 o'clock position (as viewed in FIG. 18) such the applicator head is extended a third distance from the housing of the applicator, wherein the third distance is greater than the second distance of FIG. 17.

Figure 19:
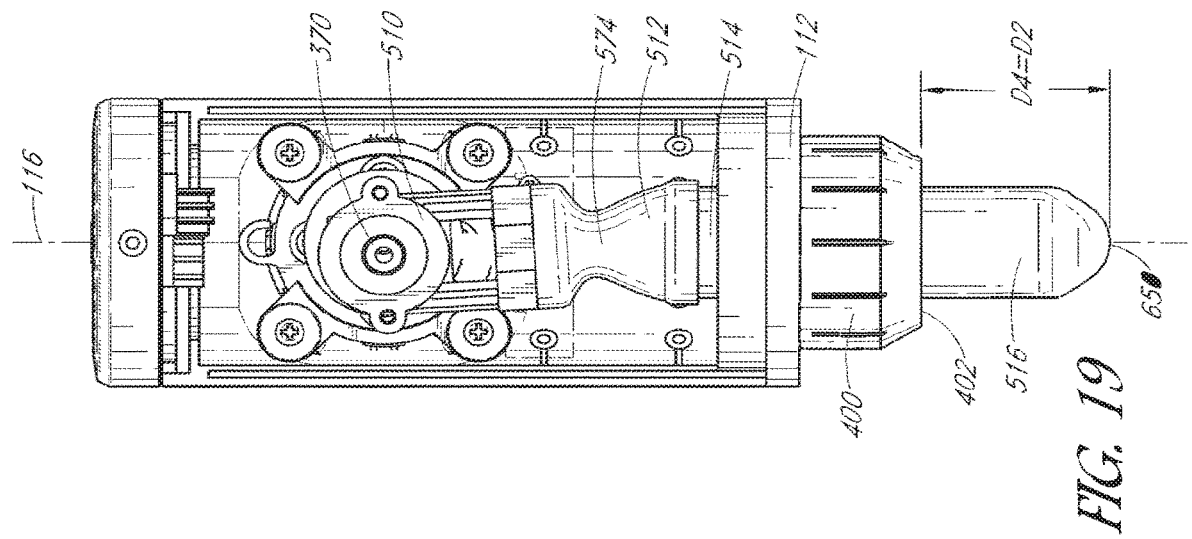

FIG. 19 illustrates a plan view of the portable electromechanical percussive massage applicator similar to the views of FIGS. 16, 17 and 18, the view in FIG. 19 showing the crank in the 9 o'clock position (as viewed in FIG. 19) such the applicator head is extended a fourth distance from the housing of the applicator, wherein the fourth distance is substantially equal to the second distance of FIG. 17.

Figure 20:
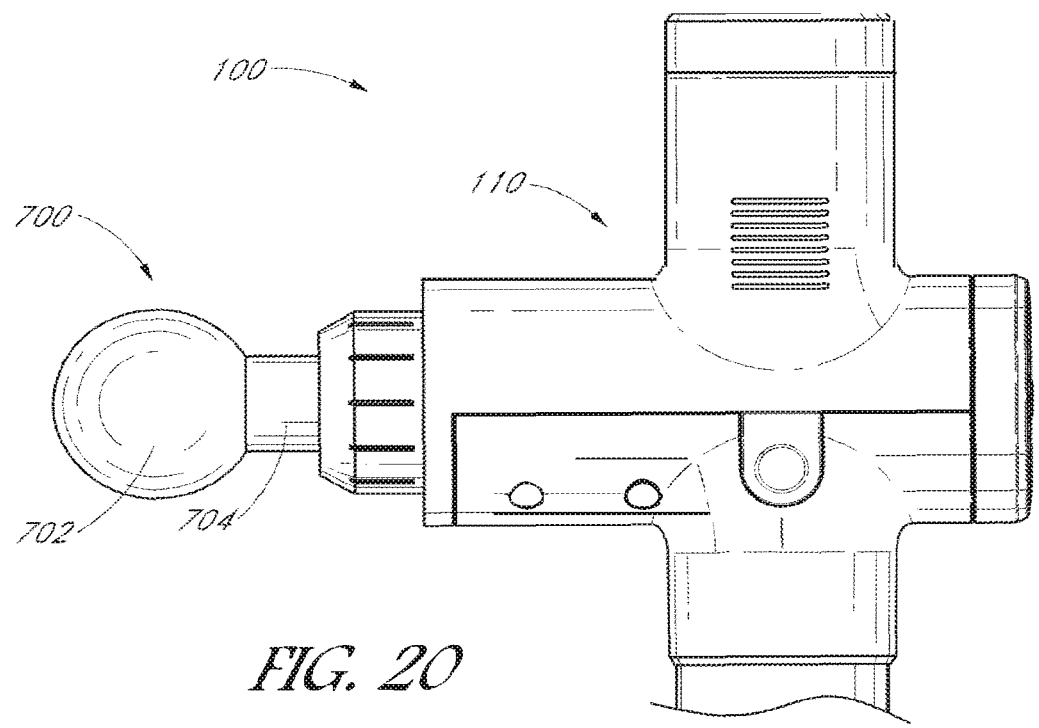

FIG. 20 illustrates a left elevational view of the percussive massage applicator of FIGS. 1 and 2 with the bullet-shaped applicator removed and replaced with a spherical applicator.

Figure 21:
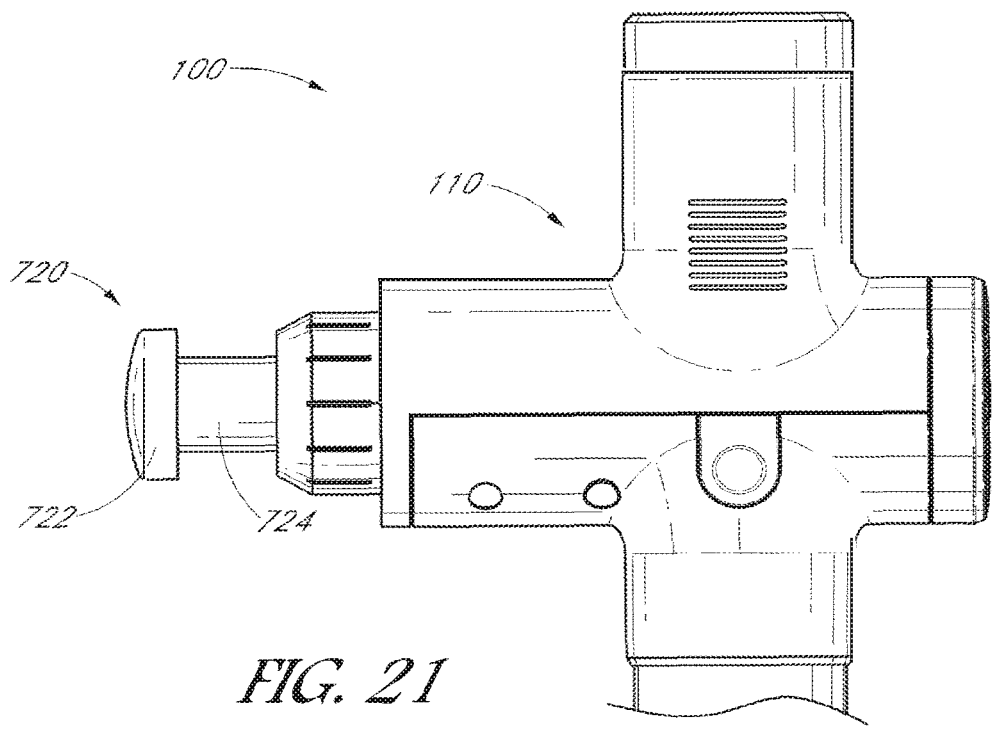

FIG. 21 illustrates a left elevational view of the percussive massage applicator of FIGS. 1 and 2 with the bullet-shaped applicator removed and replaced with a convex applicator having a larger surface area than the bullet-shaped applicator.

Figure 22:
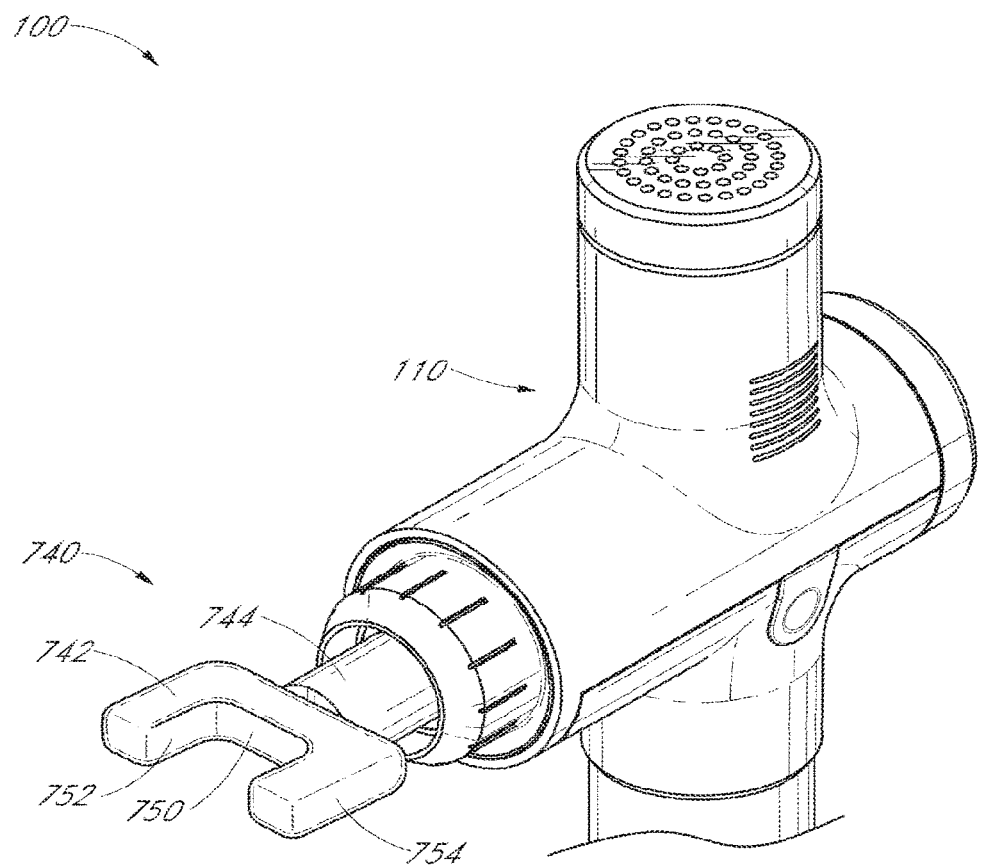

FIG. 22 illustrates a left elevational view of the percussive massage applicator of FIGS. 1 and 2 with the bullet-shape applicator removed and replaced with a two-pronged applicator having two smaller distal surface areas.

Figure 23:
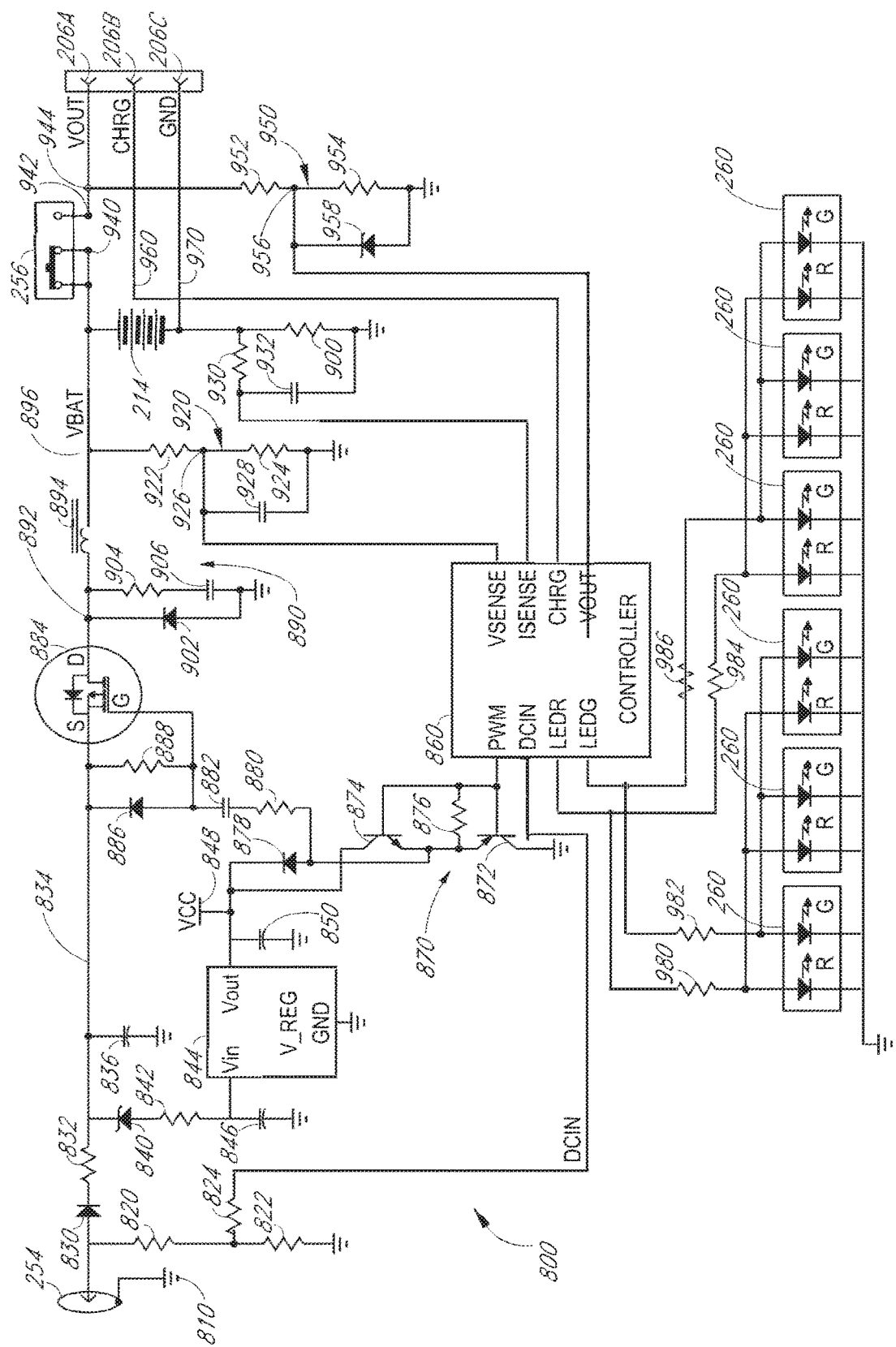

FIG. 23 illustrates a schematic diagram of the battery controller circuit.

Figure 24:
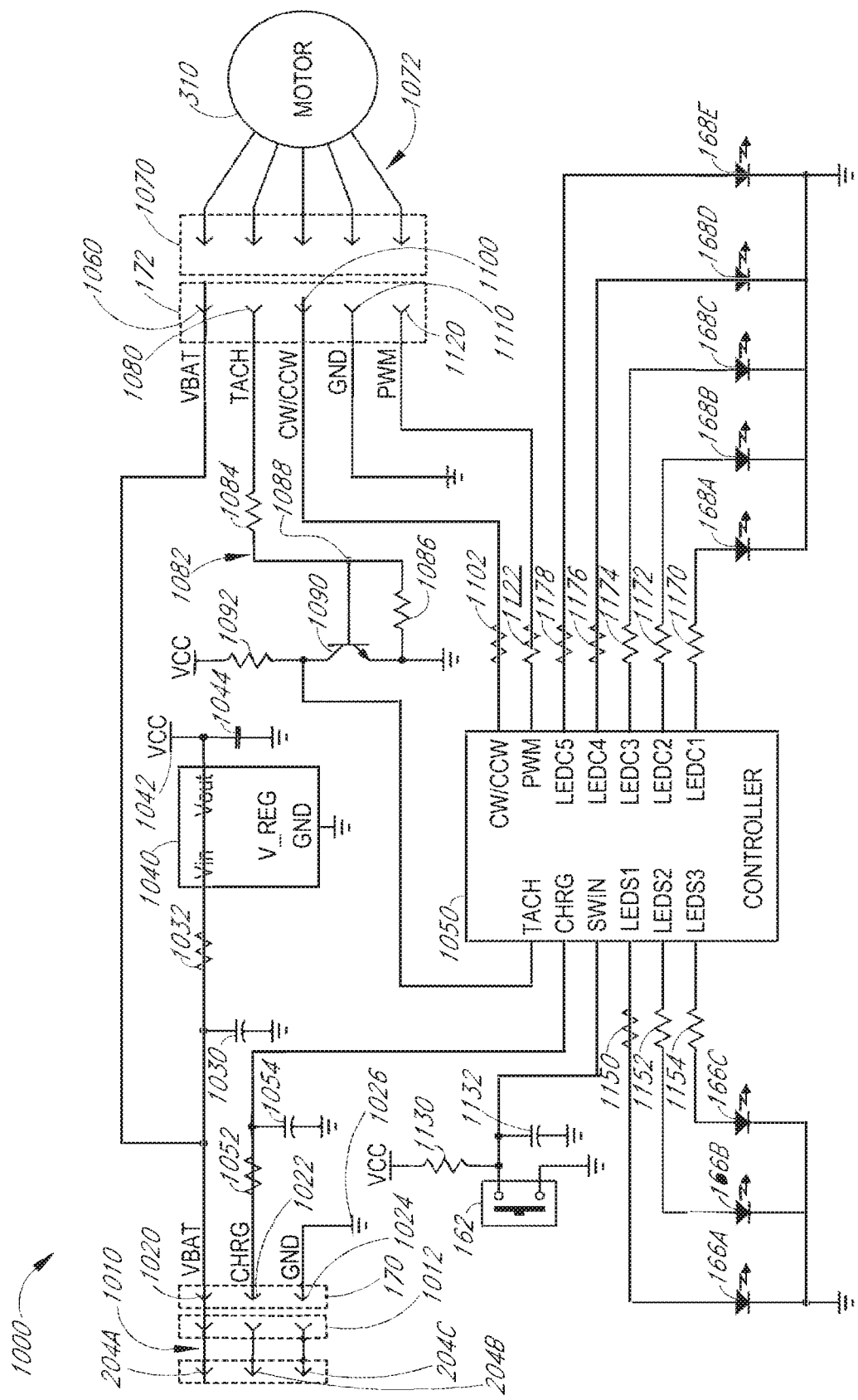

FIG. 24 illustrates a schematic diagram of the motor controller circuit.

Figure 25:
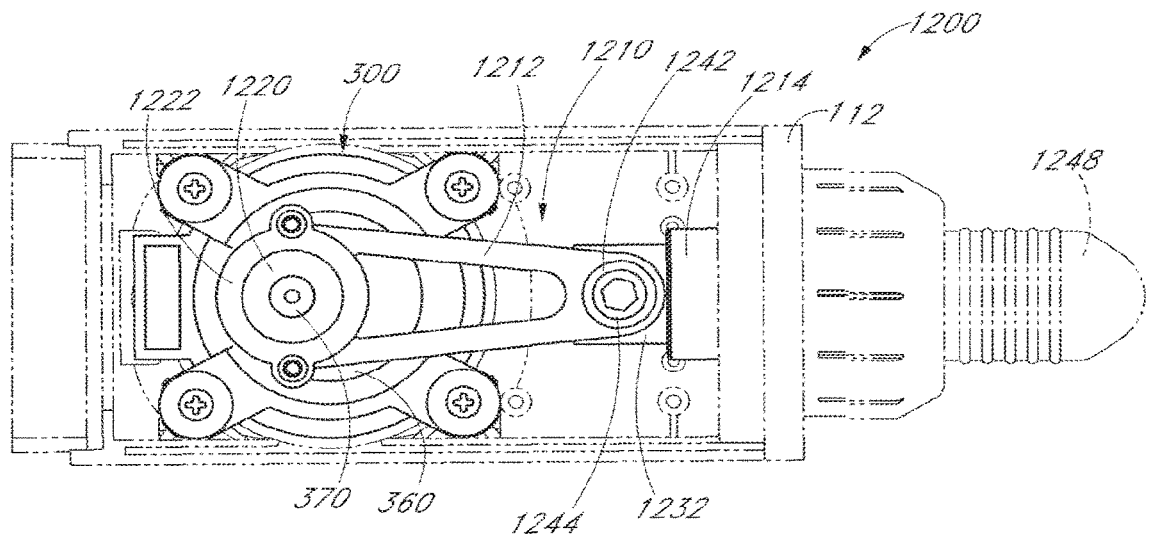

FIG. 25 illustrates a plan view of a modified percussive massage applicator having a solid reciprocation linkage, the view shown with the lower cover removed, the view looking upward toward the electrical motor of the applicator, the components other than the motor assembly and the reciprocation assembly shown in phantom.

Figure 26:
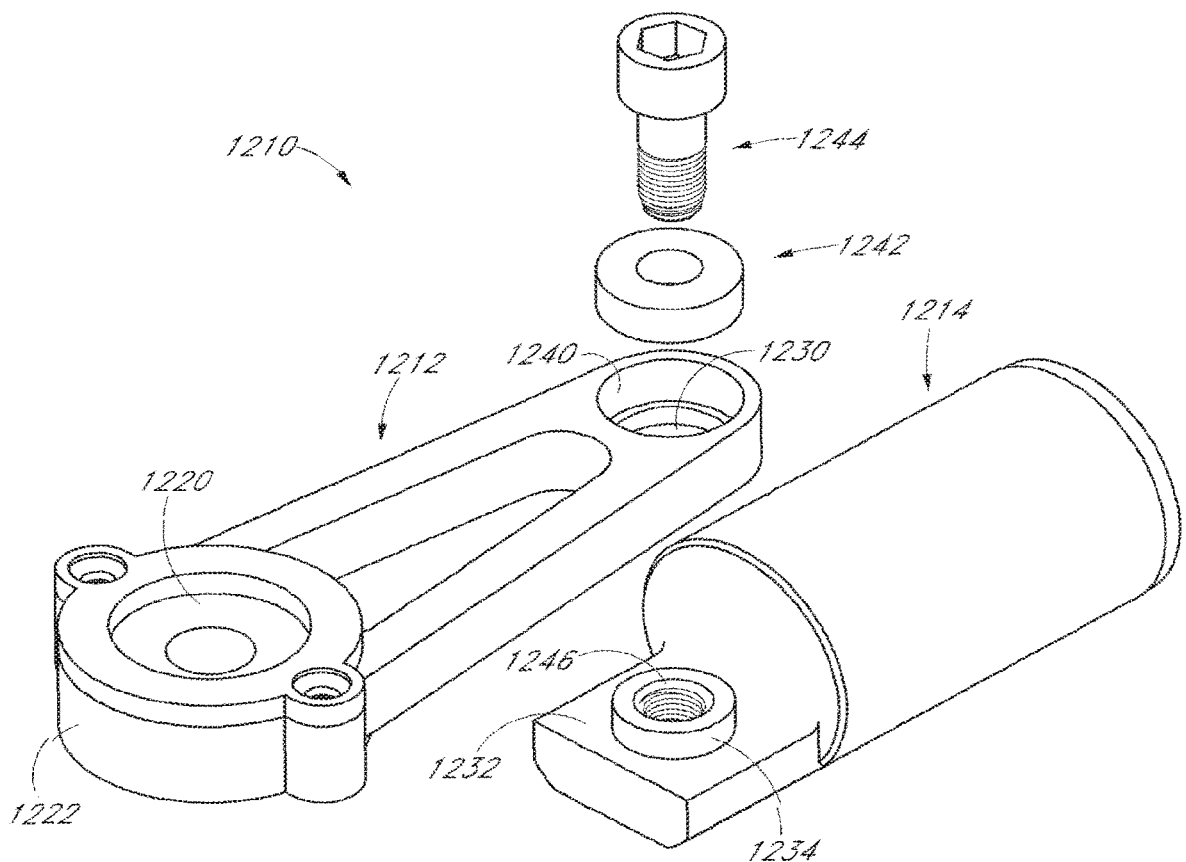

FIG. 26 illustrates an exploded perspective view of the solid reciprocation linkage of FIG. 25.

Figure 27:
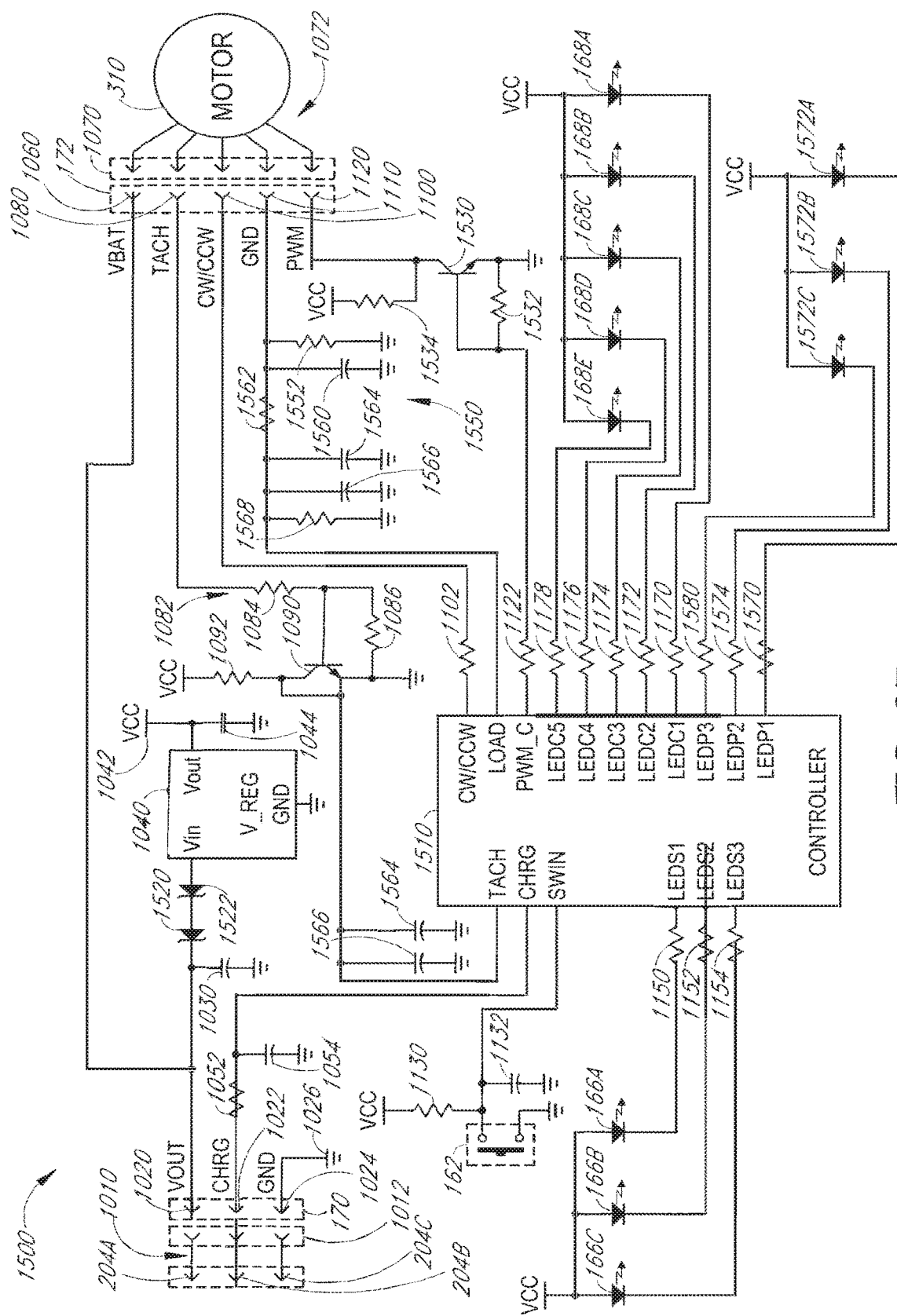

FIG. 27 illustrates a schematic diagram of a modified motor controller circuit similar to the motor controller circuit of FIG. 24, the modified motor controller circuit including a circuit to sense motor current corresponding to applied pressure and three additional light-emitting diodes (LEDs) to display ranges of pressure.

Figure 28:
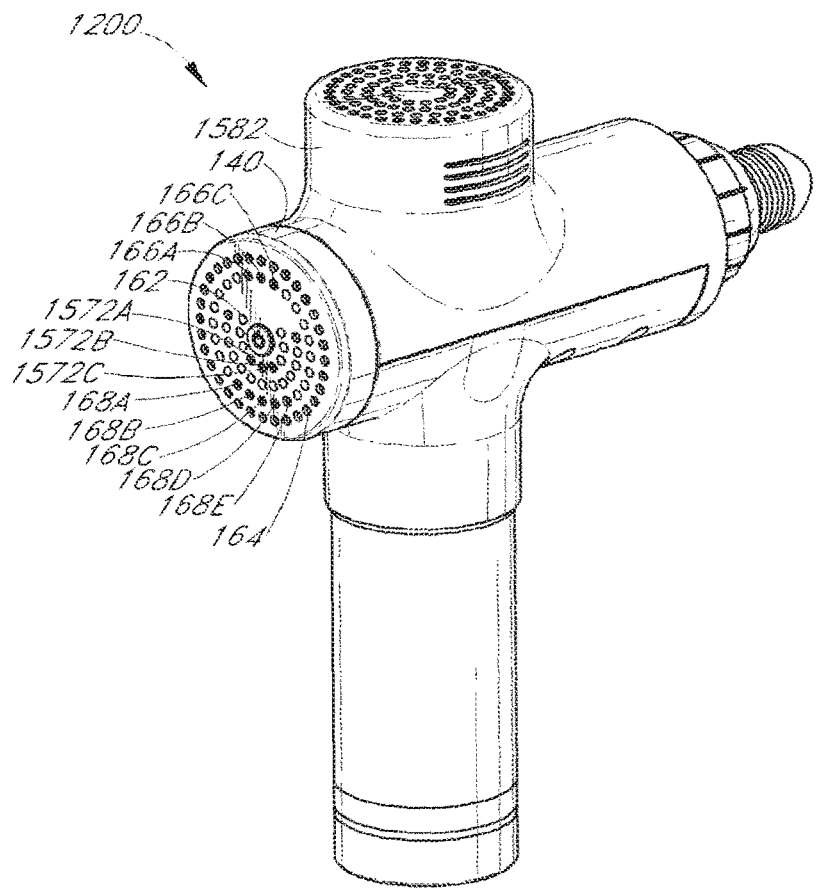

FIG. 28 illustrates a top perspective view of a modified portable electromechanical percussive massage applicator showing the top, the right side and the proximal end of the applicator, the proximal end including openings for the three additional LEDs.

Figure 29:
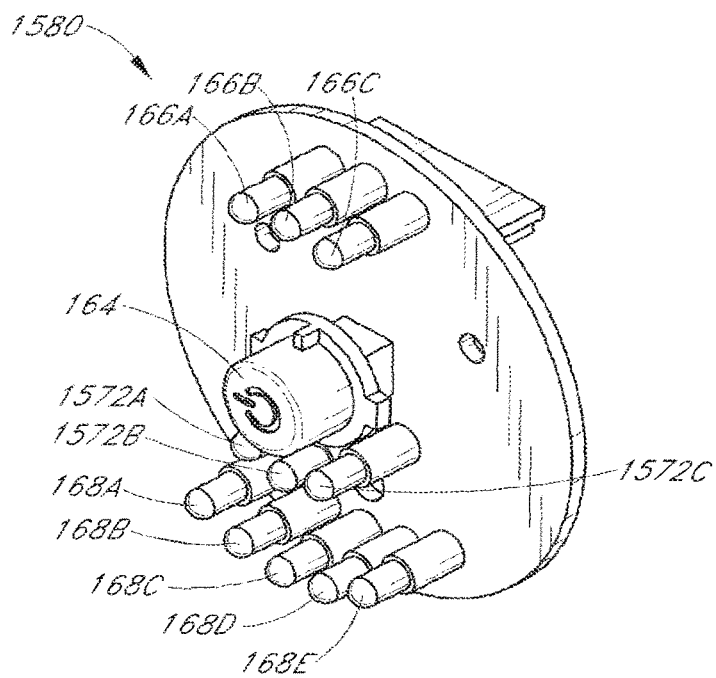

FIG. 29 illustrates a proximal end view of a motor controller printed circuit board supporting the three additional LEDs.

Figure 30:
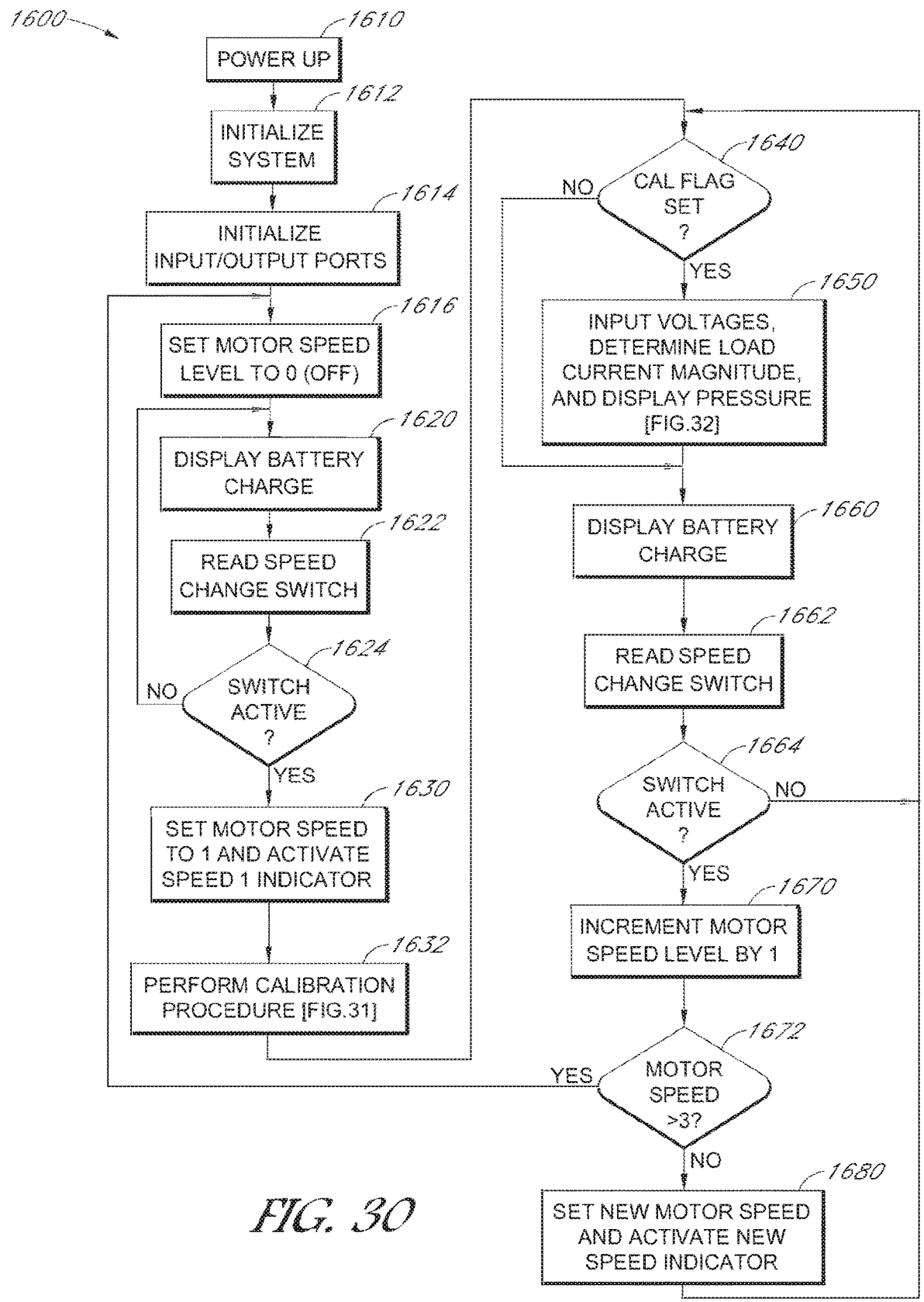

FIG. 30 illustrates a flowchart of the operation of the motor controller of FIG. 27.

Figure 31:
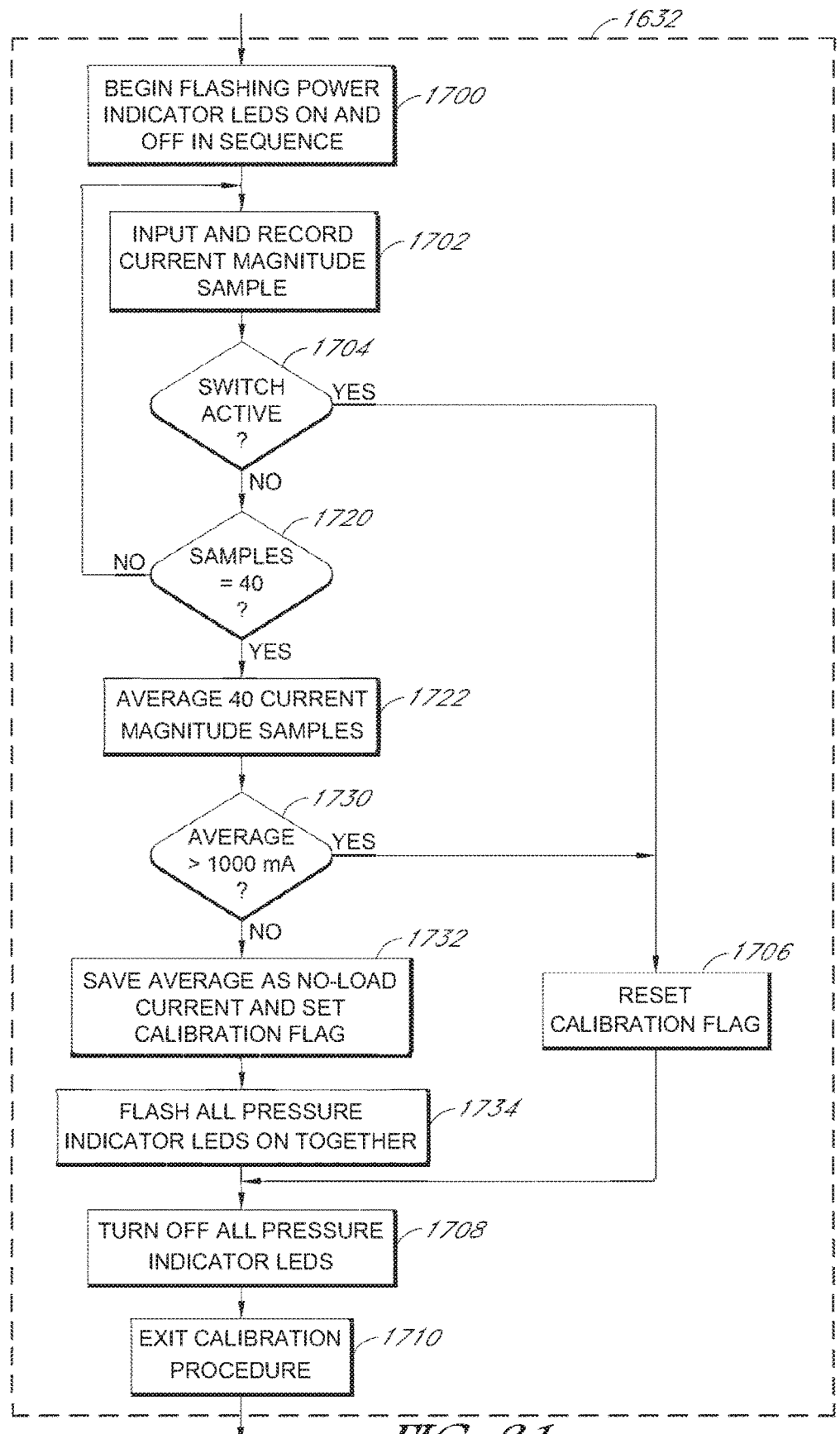

FIG. 31 illustrates a flowchart showing steps of the perform calibration procedure step of FIG. 30.

Figure 32:
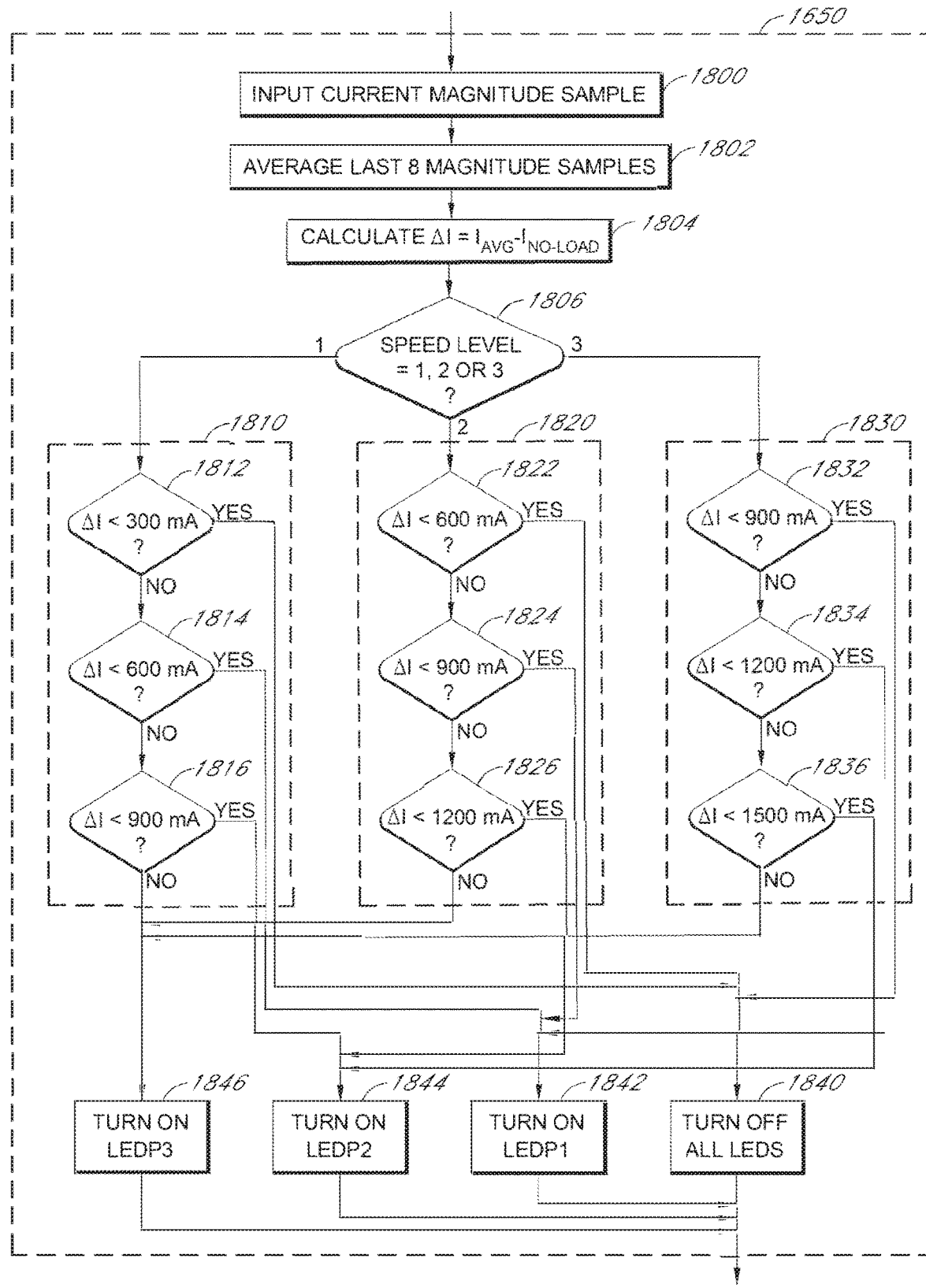

FIG. 32 illustrates a flowchart showing steps within the step of inputting voltages, determining current magnitudes and displaying pressure of FIG. 30.

Figure 33:
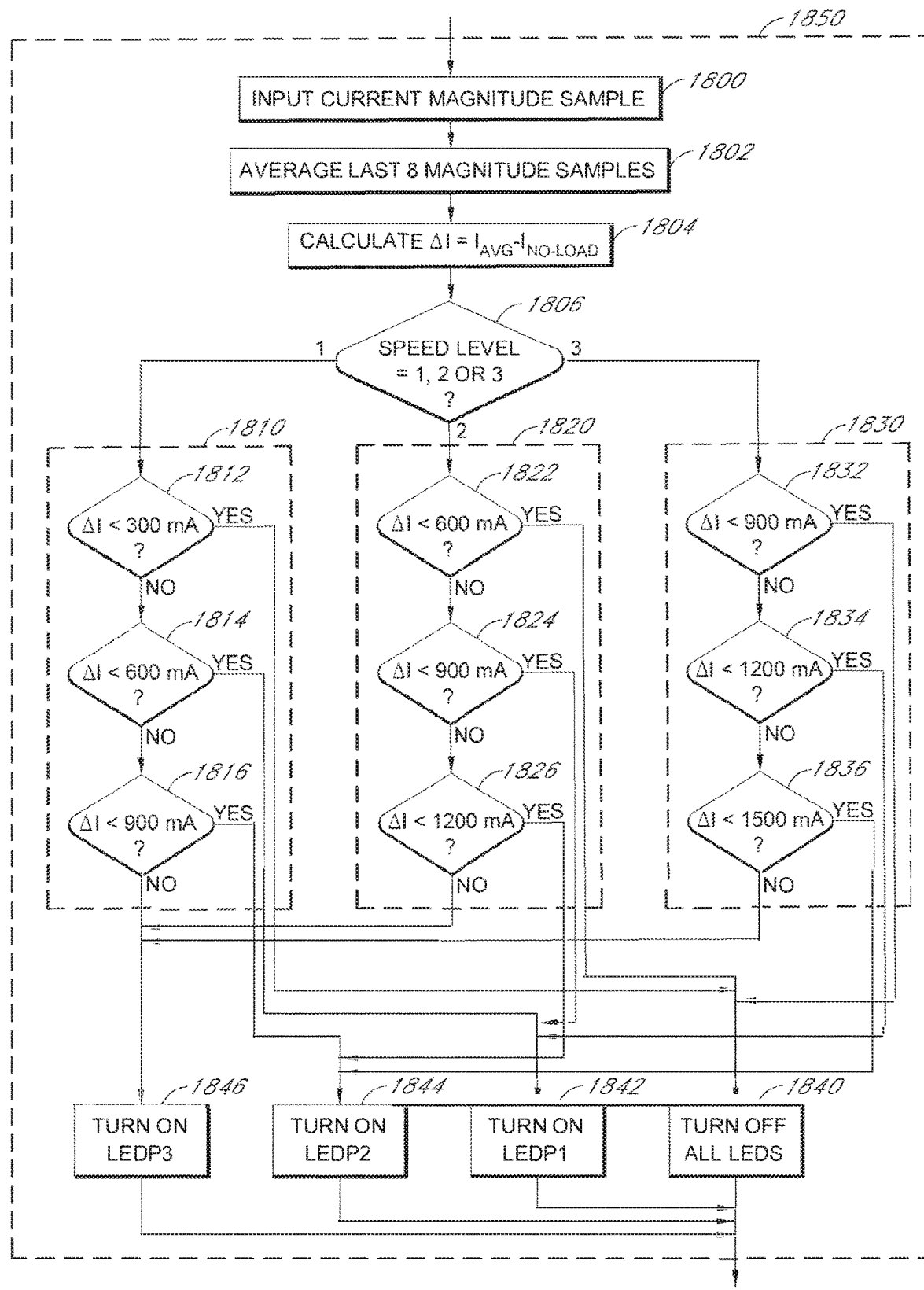

FIG. 33 illustrates a flowchart similar to the flowchart of FIG. 32, which is modified to provide a cascading pressure display instead of the discrete pressure display provided by the flowchart of FIG. 32.

Figure 34:
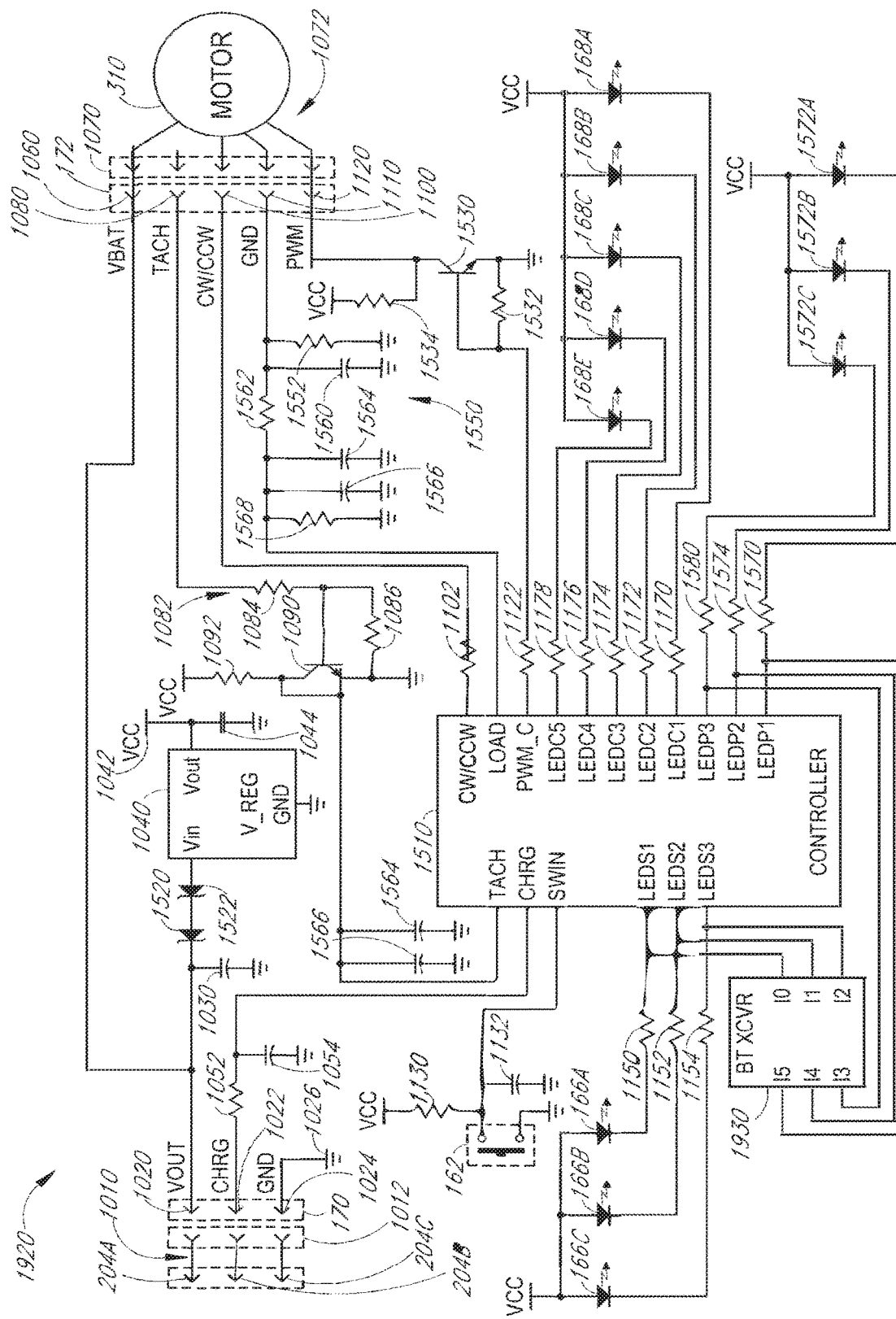

FIG. 34 illustrates a schematic diagram of a further modified motor controller circuit similar to the modified motor controller circuit of FIG. 27, the further modified motor controller circuit including a Bluetooth interface to communicate the status of the motor speed LEDs and the pressure range LEDs to a remote device.

Figure 35:
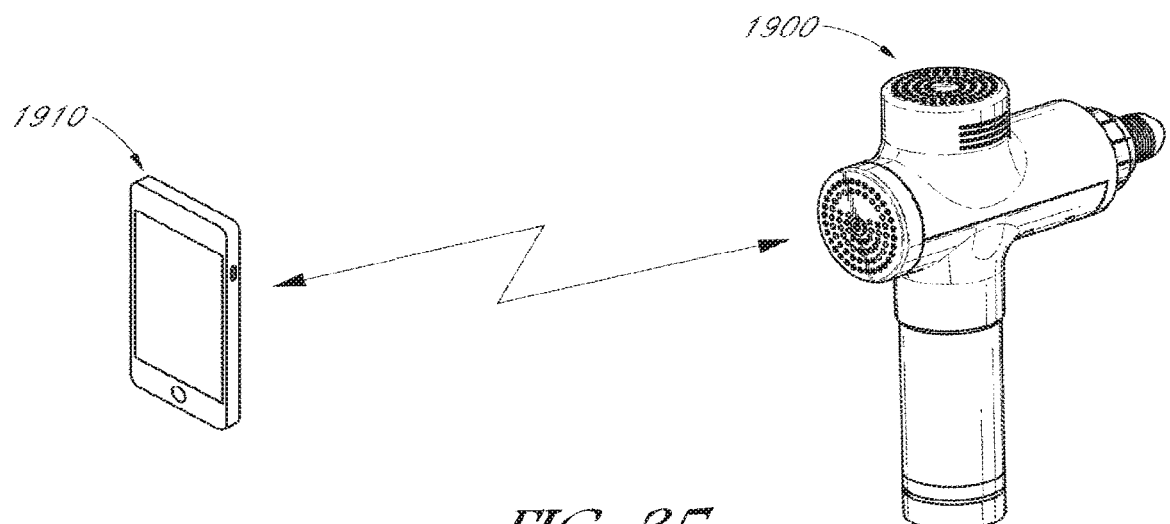

FIG. 35 illustrates a pictorial representation of the percussive massage device in communication with a remote device (e.g., a smartphone).

Figure 36:
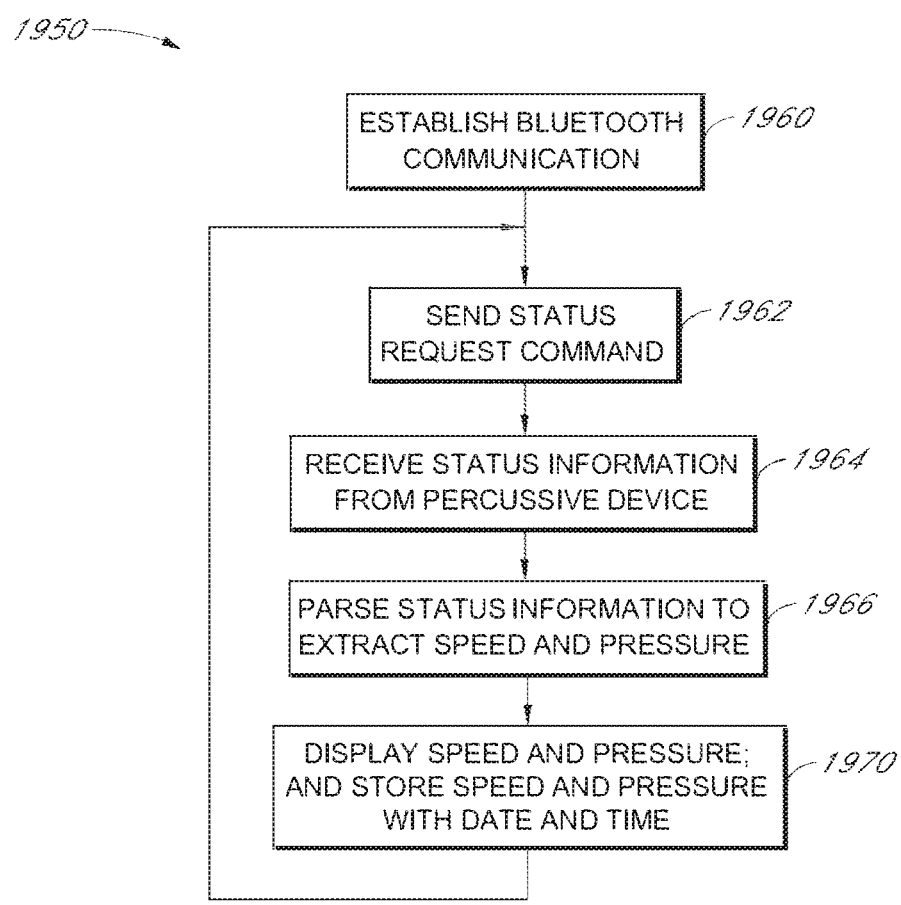

FIG. 36 illustrates a flowchart of the communication between the remote device and the percussive massage device of FIG. 35 to display and store the motor speed and the pressure range on the remote device.

Figure 37:
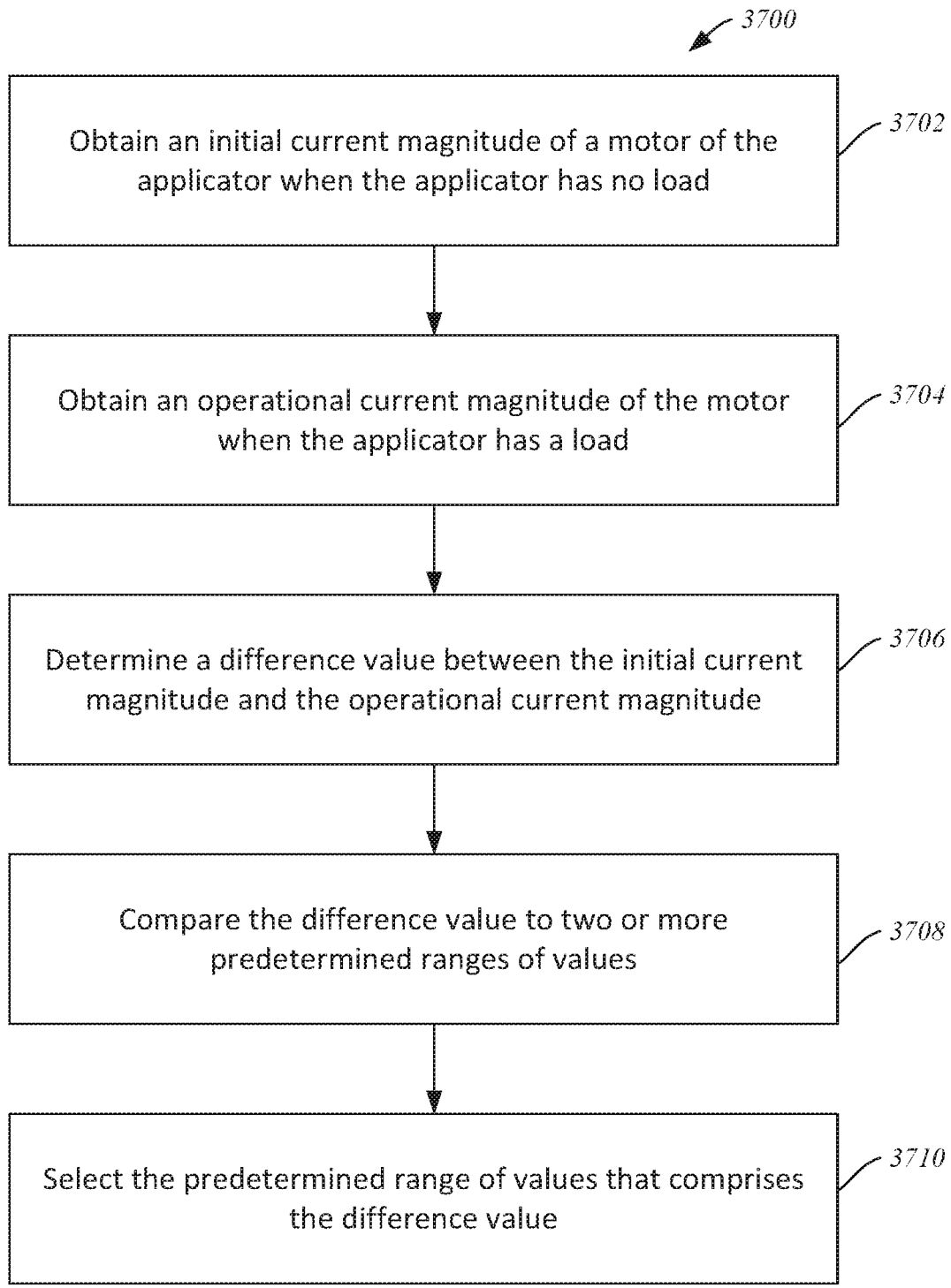

FIG. 37 illustrates a flowchart of a method for determining the pressure level of an exemplary massage applicator based on motor current consumption.

Figure 38:
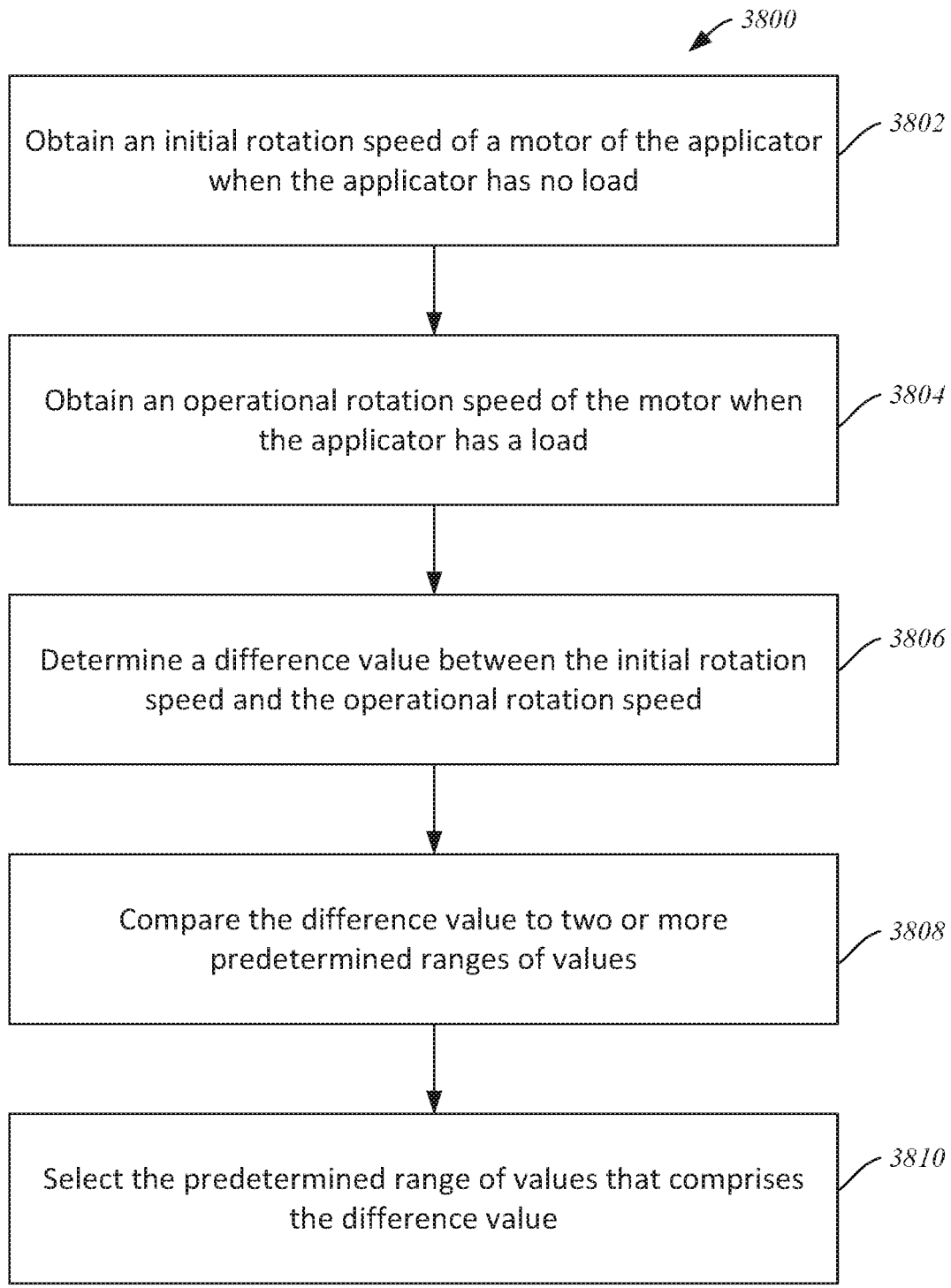

FIG. 38 illustrates a flowchart of a method for determining the pressure level of an exemplary massage applicator based on motor rotation speed.

Figure 39:
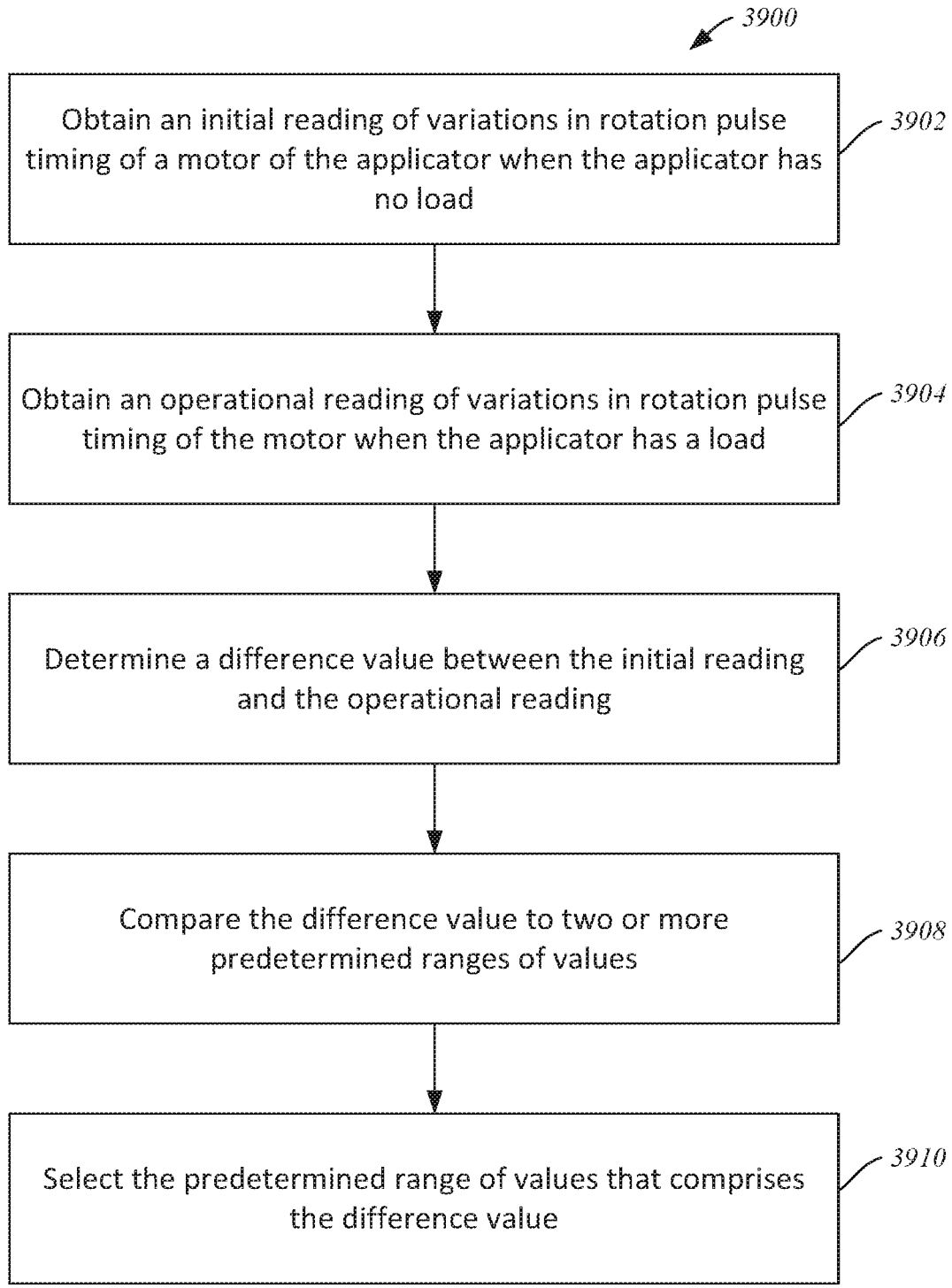

FIG. 39 illustrates a flowchart of a method for determining the pressure level of an exemplary massage applicator based on motor rotation pulse timing variation.

Figure 40:
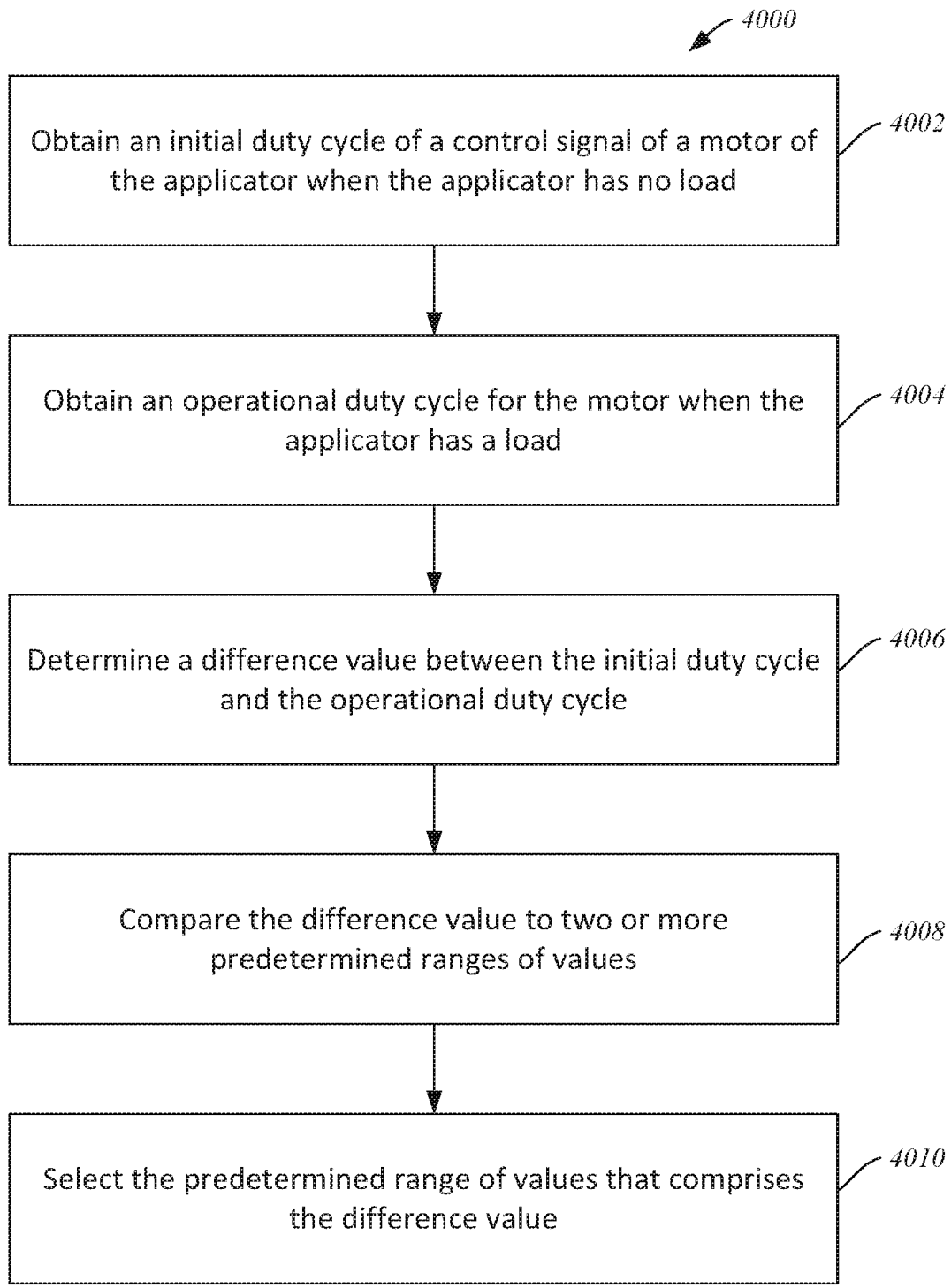

FIG. 40 illustrates a flowchart of a method for determining the pressure level of an exemplary massage applicator based on duty cycle of the control signals for the applicator motor.

While the present disclosure is subject to various modifications and alternative forms, specific embodiments thereof have been shown by way of example in the drawings and will herein be described in detail. The present disclosure should be understood to not be limited to the particular forms disclosed, but on the contrary, the intention is to cover all modifications, equivalents, and alternatives falling within the spirit and scope of the present disclosure.

DETAILED DESCRIPTION

As used throughout this specification, the words "upper," "lower," "longitudinal," "upward," "downward," "proximal," "distal," and other similar directional words are used with respect to the views being described. It should be understood that the percussive massage applicator described herein can be used in various orientations and is not limited to use in the orientations illustrated in the drawing figures.

Percussive Massage Applicator

A portable electromechanical percussive massage applicator ("percussive massage applicator") 100 is illustrated in FIGS. 1-22. As described below, the percussive massage applicator can be applied to different locations of body to apply percussion to the body to effect percussive treatment. The percussive massage applicator is operable with removably attachable applicator heads to vary the effect of the percussive strokes. The percussive massage applicator operates at a plurality of speeds (e.g., three speeds).

The portable electromechanical percussive massage applicator 100 includes a main body 110. The main body includes an upper body portion 112 and a lower body portion 114. The two body portions engage to form a generally cylindrical enclosure about a longitudinal axis 116 (FIG. 2).

A generally cylindrical motor enclosure 120 extends upward from the upper body portion 112. The motor enclosure is substantially perpendicular to the upper body portion. The motor enclosure is capped with a motor enclosure endcap 122. The motor enclosure and the upper body portion house a motor assembly 124 (FIG. 3). The upper body portion also supports a reciprocation assembly 126 (FIG. 3), which is coupled to the motor assembly as described below.

A generally cylindrical battery assembly receiving enclosure 130 extends downward from the lower body portion 114 and is substantially perpendicular to the lower body portion. A battery assembly 132 extends from the battery assembly receiving enclosure.

A main body endcap 140 is positioned on a proximal end of the main body 110. In addition to other functions described below, the main body endcap also serves as a clamping mechanism to hold the respective proximal ends of the upper body portion 112 and the lower body portion 114 together. As illustrated in FIG. 4A, the endcap includes a plurality of protrusions 142 on an inner perimeter surface 144. The protrusions are positioned to engage a corresponding plurality of L-shaped notches 146 on the outer perimeters of the proximal ends of the upper body portion and the lower body portion. In the illustrated embodiment, two notches are formed on the upper body portion and two notches are formed on the lower body portion. The protrusions on the endcap are inserted into the proximal ends of the notches until seated against the distal ends of the notches. The endcap is then twisted by a few degrees (e.g., approximately 10 degrees) to lock the endcap to the two body portions. A screw 148 is then inserted through a bore 150 in the endcap to engage the lower body portion to prevent the endcap from rotating to unlock during normal use.

As shown in FIG. 4A, the main body endcap 140 houses a motor controller (main) printed circuit board (PCB) 160. As shown in FIG. 4B, the proximal side of the main PCB supports a central pushbutton switch 162. The operation of the switch is described below in connection with the electronic circuitry. As shown in FIG. 2, the switch is surrounded on the endcap by a plurality of bores 164, which extend perpendicularly from the outer (proximal) surface of the endcap to form a plurality of concentric rows of bores. Selected ones of the bores are through bores, which allow airflow through the endcap. Three of the bores above the switch have respective speed indication light-emitting diodes (LEDs) 166A, 166B, 166C positioned therein. The three LEDs extend from the proximal side of the PCB as shown in FIG. 4B. The three LEDs provide an indication of the operational state of the percussive massage applicator 100 as described in more detail below. Five of the bores located below the switch have respective battery charge state LEDs 168A, 168B, 168C, 168D, 168E positioned therein. The five LEDs also extend from the proximal side of the PCB as shown in FIG. 4B. The five LEDs provide an indication of the charge state of the battery when the battery assembly 132 is attached and is providing power to the percussive massage applicator. As shown in FIG. 4A, the distal side of the PCB supports a first plug 170, which includes three contact pins that are connectable to the battery assembly 132 as described below. The distal side of the PCB also supports a second plug 172, which includes five contact pins that are connectable to the motor assembly 124 as described below.

As shown in FIGS. 5 and 8, a distal portion of the lower body portion 114 includes a plurality of through bores 180

(e.g., four through bores) that are aligned with a corresponding plurality of through bores 182 in the upper body portion 112. When lower body portion is attached to the upper body portion, a plurality of interconnection screws 184 pass through the through bores in the lower body portion and engage the through bores of the upper body portion to further secure the two body portions together. A plurality of plugs 186 are inserted into outer portions of the through bores of the lower body portion to hide the ends of the interconnection screws.

As shown in FIGS. 8 and 9, the lower body portion 114 includes a battery assembly receiving tray 200, which is secured to the inside of the lower body portion in alignment with the battery assembly receiving enclosure 130. The receiving tray is secured to the lower body portion with a plurality of screws 202 (e.g., four screws). The receiving tray includes a plurality of leaf spring contacts 204A, 204B, 204C (e.g., three contacts), which are positioned in a triangular pattern. The three contacts are positioned to engage a corresponding plurality of contacts 206A, 206B, 206C, which are positioned around the top edge of the battery assembly 132 when the battery assembly is positioned in the battery assembly receiving enclosure.

The battery assembly 132 includes a first battery cover half 210 and a second battery cover half 212, which enclose a battery unit 214. In the illustrated embodiment, the battery unit comprises six 4.2-volt lithium-ion battery cells connected in series to produce an overall battery voltage of approximately 25.2 volts when fully charged. The battery cells are commercially available from many suppliers, such as, for example, Samsung SDI Co., Ltd., of South Korea. The first battery cover half and the second battery cover half snap together. The two halves are further held together by an outer cylindrical cover 216, which also serves as a gripping surface when the percussive massage applicator 100 is being used. In the illustrated embodiment, the outer cover extends only over the portion of the battery assembly that does not enter the battery receiving enclosure 132. In the illustrated embodiment, the outer cover comprises neoprene or another suitable material that combines a cushioning layer with an effective gripping surface.

The upper end of the battery assembly 132 includes a first mechanical engagement tab 220 and a second mechanical engagement tab 222 (FIG. 6). As shown in FIG. 6, for example, when the battery assembly is fully inserted into the battery assembly receiving enclosure 130, the first engagement tab engages a first ledge 224 and the second engagement tab engages a second ledge 226 within the battery assembly receiving enclosure to secure the battery assembly within the battery assembly receiving enclosure.

The lower body portion 114 includes a mechanical button 230 in alignment with the first engagement tab 220. When sufficient pressure is applied to the button, the first engagement tab is pushed away from the first ledge 224 to allow the first engagement tab to move downward with respect to the first ledge and thereby disengage from the ledge. In the illustrated embodiment, the mechanical button is biased by a compression spring 232. The lower body portion further includes an opening 234 (FIG. 6) opposite the mechanical button. The opening allows a user to insert a fingertip into the opening to apply pressure to disengage the second engagement tab 222 from the second ledge 226 and at the same time to apply downward pressure to move the second engagement tab downward away from the second ledge and thereby move the battery assembly 132 downward. Once disengaged in this manner, the battery assembly is easily removed from the battery assembly receiving enclosure 130.

In the illustrated embodiment, the opening is covered in part by a flap 236. The flap may be biased by a compression spring 238. In alternative embodiments (not shown), a second mechanical button may be included in place of the opening.

The second battery cover half 212 includes an integral printed circuit board support structure 250, which supports a battery controller printed circuit board (PCB) 252. The battery controller PCB is shown in more detail in FIG. 10. In addition to other components, the battery controller PCB includes a charging power adapter input jack 254 and an on/off switch 256. In the illustrated embodiment, the on/off switch is a slide switch. The battery controller PCB further supports a plurality of light-emitting diodes (LEDs) 260 (e.g., six LEDs), which are mounted around the periphery of the battery controller PCB. In the illustrated embodiment, each LED is a dual-color LED (e.g., red and green), which may be illuminated to display either color. The battery controller PCB is mounted to a battery assembly endcap 262. A translucent plastic ring 264 is secured between the battery controller PCB and the battery assembly endcap such that the ring generally aligned with the LEDs. Accordingly, light emitted by the LEDs is emitted through the ring. As discussed below, the color of the LEDs may be used to indicate the charged state of the battery assembly 132. A switch actuator extender 266 is positioned on the actuator of the slide switch and extends through the endcap to enable the slide switch to be manipulated from the outside of the endcap.

As illustrated in FIG. 3, the motor enclosure 120 houses the electric motor assembly 124, which is shown in more detail in FIGS. 11A and 11B. The electric motor assembly includes a brushless DC electric motor 310 having a central shaft 312 that rotates in response to applied electrical energy. In the illustrated embodiment, the electric motor is a 24-volt brushless DC motor. The electric motor may be a commercially available motor. The diameter and height of the motor enclosure and the mounting structures (described below) are adaptable to receive and secure the electric motor within the motor enclosure.

The electric motor 310 is secured to a motor mounting bracket 320 via a plurality of motor mounting screws 322. The motor mounting bracket includes a plurality of mounting tabs 324 (e.g., four tabs). Each mounting tab includes a central bore 326, which receives a respective rubber grommet 330, wherein first and second enlarged portions of the grommet are positioned on opposite surfaces of the tab. A respective bracket mounting screw 332 having an integral washer is passed through a respective central hole 334 in each grommet to engage a respective mounting bore 336 in the upper body portion 112. Two of the four mounting bores are shown in FIG. 12. The grommets serve as vibration dampers between the motor mounting bracket and the upper body portion.

The central shaft 312 of the electric motor 310 extends through a central opening 350 in the motor mounting bracket 320. The central shaft engages a central bore 362 of an eccentric crank 360. The central bore is press-fit onto the central shaft of the electric motor or is secured to the shaft by another suitable technique (e.g., using a setscrew).

The eccentric crank 360 has a circular disk shape. The crank has an inner surface 364 oriented toward the electric motor and an outer surface 366 oriented away from the electric motor. A cylindrical crank pivot 370 is secured to or formed on the outer surface and is offset from the central bore of the crank in a first direction by a selected distance (e.g., 2.8 millimeters in the illustrated embodiment). An arcuate cage 372 extends from the inner surface of the crank and is generally positioned diametrically opposite the crank pivot with reference to the central bore 362 of the crank. A semi-annular weight ring 374 is inserted into the arcuate cage and is secured therein by screws, crimping or by using another suitable technique. The masses of the arcuate cage and the semi-annular weight ring operate to at least partially counterbalance the mass of the crank and the forces applied to the crank, as described below.

As shown in FIGS. 12 and 13, the distal end of the upper body portion 112 supports a generally cylindrical outer sleeve 400 having a central bore 402. In the illustrated embodiment, a distal portion 406 proximate to a distal end 404 of the outer sleeve is tapered inward toward the central bore. The outer sleeve has an annular base 408 that is secured to the distal end of the upper body portion by a plurality of screws 410 (e.g., three screws).

The outer sleeve 400 surrounds a generally cylindrical mounting sleeve 420 that is secured within the outer sleeve when the outer sleeve is secured to the upper body portion 112. The mounting sleeve surrounds a cylinder body 422 that is clamped by the mounting sleeve and is secured in a concentric position with respect to the longitudinal axis 116 of the percussive massage applicator 100. In addition to securing the cylinder body, the mounting sleeve serves as a vibration damper to reduce vibrations propagating from the cylinder body to the main body 110 of the percussive massage applicator. In the illustrated embodiment, the cylinder body has a length of approximately 25 millimeters and has an inner bore 424, which has an inner diameter of approximately 25 millimeters. In particular, the inner diameter of the cylinder body is at least 25 millimeters plus a selected clearance fit (e.g., approximately 25 millimeters plus approximately 0.2 millimeters).

As shown in FIG. 3, the percussive massage applicator 100 includes the reciprocating assembly 126, which comprises a crank engagement bearing holder 510, which may also be referred to as a transfer bracket; a flexible interconnection linkage 512, which may also be referred to as a flexible transfer linkage; a piston 514; and an applicator head 516. The reciprocating assembly is shown in more detail in FIGS. 14 and 15.

The crank engagement bearing holder 510 comprises a bearing housing 530 having an upper end wall 532 that defines the end of a cylindrical cavity 534. An annular bearing 536 fits within the cylindrical cavity. A removably attachable lower end wall 538 is secured to the bearing housing by a plurality of screws 540 (e.g., two screws) to constrain the annual bearing within the cylindrical cavity. The annular bearing includes a central bore 542 that is sized to engage the cylindrical crank pivot 370 of the eccentric crank 360.

The crank engagement bearing holder 510 further includes an interconnect portion 550 that extends radially from the bearing housing 530. The interconnect portion includes a disk-shaped interface portion 552 having a threaded longitudinal central bore 554. The central bore is aligned with a radial line 556 directed toward the center of bearing housing. In the illustrated embodiment, the central bore is threaded with an 8×1.0 metric external thread. The interface portion has an outer surface 558, which is orthogonal to the radial line. The center of the outer surface of the interface portion is approximately 31 millimeters from the center of the bearing housing. The interface portion has an overall diameter of approximately 28 millimeters and has a thickness of approximately 8 millimeters. A lower portion 560 of the interface portion may be flattened to provide clearance with other components. Selected portions of the interface portion may be removed to form ribs 562 to reduce the overall mass of the interface portion.

A threaded radial bore 564 is formed in the interface portion 552. The threaded radial bore extends from the outer perimeter of the interface portion to the threaded longitudinal central bore 554. The threaded radial bore has an internal thread selected to engage a bearing holder setscrew 566 that is inserted into the third threaded bore. The bearing holder setscrew is rotated to a selected depth as described below.

As used herein, "flexible" in connection with the flexible interconnection linkage 512 means that the linkage is capable of bending without breaking. The linkage comprises a resilient rubber material. The linkage may have a Shore A durometer hardness of around 50; however, softer or harder materials in a medium soft Shore hardness range of 35 A to 55 A may be used. The linkage is molded or otherwise formed to have a shape similar to an hour glass. That is, the shape of the linkage is relatively larger at each end and relatively narrower in the middle. In the illustrated embodiment, the linkage has a first disk-shaped end portion 570 and a second disk-shaped end portion 572. In the illustrated embodiment, the two end portions have similar thicknesses of approximately 4.7 millimeters and have similar outer diameters of approximately 28 millimeters. The material between the two end portions tapers to middle portion 574, which has a diameter of approximately 18 millimeters. In general, the middle portion has a diameter that is between 50 percent and 75 percent of the diameter of the end portions; however, the middle portion may be relatively smaller or relatively larger to accommodate materials having a greater hardness or a lesser hardness. The linkage has an overall length between the outer surfaces of the two end portions of approximately 34 millimeters. As discussed in more detail below, the smaller diameter middle portion of the linkage allows the linkage to flex easily between the two end portions.

A first threaded interconnect rod 580 extends from the first end portion 570 of the flexible interconnection linkage 512. A second threaded interconnect rod 582 extends from the second end portion 572 of the linkage. In the illustrated embodiment, the interconnect rods are metallic and are embedded into the respective end portions. For example, in one embodiment, the linkage is molded around the two interconnect rods. In other embodiment, the two interconnect rods are adhesively fixed within respective cavities formed in the respective end portions. In a still further embodiment, the two interconnect rods are formed as integral threaded rubber portions of the linkage.

The first interconnect rod 580 of the flexible interconnection linkage 512 has an external thread selected to engage with the internal thread of the threaded longitudinal central bore 554 of the crank engagement bearing holder 510 (e.g., an 8×1.0 metric external thread). When the thread of the first interconnect rod is fully engaged with the thread of the longitudinal central bore, the bearing holder setscrew 566 is rotated to cause the inner end of the setscrew to engage the thread of the first interconnect rod within the longitudinal central bore to inhibit the first interconnect rod from rotating out of the longitudinal central bore.

In the illustrated embodiment, the second interconnect rod 582 of the flexible interconnection linkage 512 has an external thread similar to the thread of the first interconnect rod 580 (e.g., an 8×1.0 metric external thread). In other embodiments, the threads of the two interconnect rods may be different.

In the illustrated embodiment, the piston 514 comprises stainless steel or another suitable material. The piston has an outer diameter that is selected to fit snugly within the inner bore 424 of the cylinder body 422 described above. For example, the outer diameter of the illustrated piston is no greater than approximately 25 millimeters. As discussed above, the inner diameter of the inner bore of the cylinder body is at least 25 millimeters plus a selected minimum clearance allowance (e.g., approximately 0.2 millimeter). Thus, with the outer diameter of the piston being no more than 25 millimeters, the piston has sufficient clearance with respect to the cylinder body that the piston is able to move smoothly within the cylinder body without interference. The maximum clearance is selected such that no significant play exists between the two parts.

In the illustrated embodiment, the piston 514 comprises a cylinder having an outer wall 600 that extends for a length of approximately 41.2 millimeters between a first end 602 and a second end 604. A first bore 606 is formed in the piston for a selected distance from the first end toward the second end. For example, in the illustrated embodiment, the first bore has a depth (e.g., length toward the second end) of approximately 31.2 millimeters and has a base diameter of approximately 18.773 millimeters. A first portion 608 (FIG. 15) of the first bore is threaded to form a 20×1.0 metric internal thread to a depth of approximately 20 millimeters in the first bore.

A second bore 610 (FIG. 15) is formed from the second end 604 of the piston 514 toward the first end. The second bore has a base diameter of approximately 6.917 millimeters and has a length sufficient to extend the second bore to the cavity formed by the first bore (e.g., a length of approximately 10 millimeters in the illustrated embodiment). The second bore is threaded for its entire length to form an internal thread in the second bore. The internal thread of the second bore engages the external thread of the second interconnect rod 582 of the interconnection linkage 512. Accordingly, in the illustrated embodiment, the second bore has an 8×1.0 metric internal thread.

A third bore 620 is formed in the piston 514 near the second end 604 of the piston. The third threaded bore extends radially inward from the outer wall 600 of the piston to the second threaded bore. In the illustrated embodiment, the third bore is threaded for the entire length of the bore. The third bore has an internal thread selected to engage a piston setscrew 622, which is inserted into the third threaded bore. When the external thread of the second interconnect rod 582 of the flexible interconnection linkage 512 is fully engaged with the internal thread of the second bore 610 of the piston, the piston setscrew is rotated to cause the inner end of the setscrew to engage the external thread of the second interconnect rod within the second bore to inhibit the second interconnect rod from rotating out of engagement with the thread of the second bore.

The applicator head 516 of the reciprocating assembly 500 can be configured in a variety of shapes to enable a user to apply different types of percussive massage. The illustrated applicator head is "bullet-shaped" and is useful for apply percussive massage to selected relatively small surface areas of a body such as, for example, trigger points. In the illustrated embodiment, the applicator head comprises a medium hard to hard rubber material. The applicator head has an overall length from a first distal (application) end 650 to a second proximal (mounting) end 652 of approximately 55 millimeters. The applicator head has an outer diameter of approximately 25 millimeters for a length of approximately 32 millimeters along a main body portion 654. An engagement portion 656 at the proximal (mounting) end of the applicator head has a length of approximately 11 millimeters and is threaded for a distance of approximately 9 millimeters to form an external 20×1.0 metric thread that is configured to engage the internal thread of the first bore 606 of the piston 514. The thread of the applicator head is removably engageable with the thread of the piston to allow the applicator head to be removed and replaced with a different applicator head as described below. The distal (applicator) end of the applicator has a length of approximately 12 millimeters and tapers from the diameter of the main body portion (e.g., approximately 25 millimeters to a blunt rounded portion 658 having the shape of a truncated spherical cap. The spherical cap extends distally for approximately 3.9 millimeters. The spherical cap has a longitudinal of approximately 10 millimeters and a lateral radius of approximately 7.9 millimeters. In the illustrated embodiment, the applicator head has a hollow cavity 660 for a portion of the length from the proximal mounting end 652. The cavity reduces the overall mass of the applicator head to reduce the energy required to reciprocate the applicator head as described below.

In the illustrated embodiment, percussive massage applicator 100 is assembled by positioning and securing the motor assembly 124 in the upper body portion 112 as described above. A cable (not shown) from the motor 310 in the motor assembly is connected to the five-pin second plug 172.

After installing the motor assembly 300, the reciprocation assembly 126 is installed in the enclosure 110 by first attaching the flexible interconnection linkage 512 to the crank engagement bearing holder 510 by threading the first threaded interconnect rod 580 into the longitudinal central bore 554. The first threaded interconnect rod is secured within the longitudinal central bore by engaging the bearing holder setscrew 566 into the threaded radial bore 564. The annular bearing 536 is installed within the cylindrical cavity 534 of the bearing bracket and is secured therein by positioning the lower end wall 538 over the bearing and securing the lower end wall with the screws 548. It should be understood that the annular bearing can be installed either before or after the bearing bracket is attached to the flexible linkage.

The crank engagement bearing holder 510 and the connected flexible interconnection linkage 512 are installed by positioning the central bore 542 of the annular bearing 536 over the cylindrical crank pivot 370 of the eccentric crank 360 with the flexible interconnection linkage aligned with the longitudinal axis 116. The second threaded interconnect rod 582 is directed toward the bore 424 of the cylinder body 422 within the cylindrical outer sleeve 400 at the distal end of the percussive massage applicator 100.

The applicator head 516 is attached to the piston 514 by threading the engagement portion 656 of the applicator head into the threaded first portion 608 of the piston. The interconnected applicator head and piston are then installed through the bore 424 of the cylinder body 422 to engage the second bore 610 of the piston with the second threaded interconnector rod 582 of the flexible interconnection linkage 512. The interconnected applicator had and the piston are rotated within the bore of the cylinder body to thread the second bore of the piston onto the second threaded interconnect rod. When the second bore and the second threaded interconnector rod are fully engaged as shown in FIG. 7, for example, the piston setscrew 622 is threaded into the third bore 620 of the piston to engage the threads of the second threaded interconnect rod of the flexible linkage to secure the piston to the flexible linkage. In the illustrated embodiment, the interconnected threads of the piston and the second threaded interconnect rod are configured such that the third bore of the piston is directed generally downward as shown in FIG. 7 and is thereby accessible to tighten the piston setscrew within the third bore. After the piston is secured to the flexible linkage, the applicator head may be unthreaded from the piston without unthreading the piston from the flexible linkage to allow the applicator head to be removed and replaced without having to remove the piston.

After installing the reciprocation assembly 126, as described above, the lower body portion 114 is installed by aligning the lower body portion with the upper body portion 112 and securing the two body portions together using the screws 184 (FIG. 5). The main body endcap 140 is then placed over the proximal ends of the two body portions to engage the protrusions 142 of the endcap with the L-shaped notches 146 of the two body portions. The endcap is then secured to prevent inadvertent removal by inserting the screw 148 through the bore 150 and into the material of the lower body portion.

The battery assembly 132 is installed in the battery assembly receiving enclosure 130 of the lower body portion 114 of the percussive massage applicator 100 and electrically and mechanically engaged as described above. The battery assembly may be charged while installed; or the battery assembly may be charged while removed from the percussive massage applicator.

The operation of the percussive massage applicator 100 is illustrated in FIGS. 16-19, which are views looking up at the motor assembly in the upper body portion 112 with the lower cover 114 and the battery assembly 132 removed. In FIG. 16, the eccentric crank 360 attached to the shaft 312 of the motor 310 is shown at a first reference position, which is designated as the 12 o'clock position. In this first reference position, the cylindrical crank pivot 370 on the outer surface 366 of the eccentric crank is at a most proximal location (nearest the top of the illustration in FIG. 16). The crank pivot is positioned in alignment with the longitudinal axis 116. The crank engagement bearing holder 510, the flexible interconnection linkage 512, the piston 514 and the applicator head 516 are all aligned with the longitudinal axis. In this first position, the distal end of the applicator head extends by a first distance D1 from the distal end of the outer sleeve 400.

In FIG. 17, the shaft 312 of the motor 300 has rotated the eccentric crank 360 clockwise 90 degrees (as viewed in FIGS. 16-19). Accordingly, the cylindrical crank pivot 370 on the eccentric crank is now positioned to the right of the shaft of the motor at a second position designated as the 3 o'clock position. The central bore 542 of the annular bearing 536 within the crank engagement bearing holder 510 must move to the right because of the engagement with the cylindrical crank pivot. The piston 514 is constrained by the bore 424 of the cylinder body 422 (FIGS. 12-13) to remain aligned with the longitudinal axis 116. The second end 572 of the flexible interconnection linkage 512 remains aligned with the piston because of the second threaded interconnect rod 582. The first end 570 of the flexible interconnection linkage remains aligned with the crank engagement bearing holder 510 because of the first threaded interconnect rod 580. The smaller middle portion 574 of the flexible interconnection linkage allows the flexible interconnection to bend to the right to allow the crank engagement bearing holder to tilt to the right as shown. In addition to moving to the right and away from the longitudinal axis, the cylindrical crank pivot has also moved distally away from the proximal end of the percussive massage applicator 100, which causes the crank engagement bearing holder to also move distally. The distal movement of the crank engagement bearing holder is coupled to the piston via the flexible interconnector to push the piston longitudinally within the cylinder. The longitudinal movement of the piston causes the applicator head 516 to extend further outward to a second distance D2 from the distal end of the outer sleeve 400. The second distance D2 is greater than the first distance D1.

In FIG. 18, the shaft 312 of the motor 310 has rotated the eccentric crank 360 clockwise an additional 90 degrees to a position designated as the 6 o'clock position. Accordingly, the cylindrical crank pivot 370 is again aligned with the longitudinal axis 116. The crank engagement bearing holder 510 and the flexible interconnection linkage 512 have returned to the initial straight-line configuration in alignment with the piston 514. The cylindrical crank pivot has moved further from the proximal end of the percussive massage applicator 100. Thus, the crank engagement bearing holder and the flexible interconnection linkage push the piston longitudinally within the bore 424 of the cylinder body 422 to cause the applicator head 516 to extend further outward to a third distance D3 from the distal end of the outer sleeve 400. The third distance D3 is greater than the second distance D2.

In FIG. 19, the shaft 312 of the motor 310 has rotated the eccentric crank 360 clockwise an additional 90 degrees. Accordingly, the cylindrical crank pivot 370 is now positioned to the left of the shaft of the motor at a fourth position designated as the 9 o'clock position. The piston 514 is constrained by the bore 424 of the cylinder body 422 to remain aligned with the longitudinal axis 116. The smaller middle portion 574 of the flexible interconnection linkage 512 allows the flexible interconnection linkage to bend to the left to allow the crank engagement bearing holder 510 to tilt to the left as shown. In addition to moving to the left and away from the longitudinal axis, the cylindrical crank pivot has also moved proximally toward the proximal end of the percussive massage applicator 100. The proximal movement pulls the piston longitudinally within the cylinder to cause the applicator head 516 to retreat proximally to a fourth distance D4 from the distal end of the outer sleeve 400. The fourth distance D4 is less than the third distance D2 and is substantially the same as the second distance D2.

A further rotation of the shaft 312 of the motor 310 by an additional 90 degrees clockwise returns the eccentric crank 360 to the original 12 o'clock position shown in FIG. 16 to return the cylindrical crank pivot 370 to the most proximal location. This further rotation causes the distal end of the applicator head 516 to retreat to the original first distance D1 from the outer sleeve 400. Continued rotation of the shaft of the motor causes the distal end of the applicator head to repeatedly extend and retreat with respect to the outer sleeve. By placing the distal end of the applicator head on a body part to be massaged, the applicator head applies percussive treatment to the selected body part.

In the illustrated embodiment, the axis of the cylindrical crank pivot 370 is located approximately 2.8 millimeters from the axis of the shaft 312 of the motor 310. Accordingly, the cylindrical crank pivot moves a total longitudinal distance of approximately 5.6 millimeters from the 12 o'clock position of FIG. 16 to the 6 o'clock position of FIG. 18. This results in a 5.6-millimeter stroke distance of the distal end of the applicator head 516 from the fully retreated first distance D1 to the fully extended third distance D3.

Conventional linkage systems between a crank and a piston have two sets of bearings. A first bearing (or set of bearings) couples a first end of a drive rod to a rotating crank. A second bearing (or set of bearings) couples a second end of a drive rod to a reciprocating piston. When the piston reaches each of the two extremes of the reciprocating motion, the piston must abruptly change directions. The stresses caused by the abrupt changes in direction are applied against the bearings at each end of the drive rod as well as to the other components in the linkage system. The abrupt changes of direction also tend to generate substantial noise.

The reciprocating linkage system 126 described herein eliminates a second bearing (or set of bearings) at the piston 514. The piston is linked to the other components of the linkage via the flexible interconnection linkage 512, which bends as the cylindrical crank pivot 370 rotates about the centerline of the shaft 312 of the motor 300. The flexible interconnect cushions the abrupt changes in direction at each end of the piston stroke. For example, as the applicator head 516 and the piston reverse direction from distal movement to proximal movement at the 6 o'clock position, the flexible interconnect may stretch by a small amount during the transition. The stretching of the flexible interconnect reduces the coupling of energy through the linkage system to the bearing 536 (FIG. 14) and the cylindrical crank pivot. Similarly, as the applicator head and the piston reverse direction from proximal movement to distal movement at the 12 o'clock position, the flexible interconnect may compress by a small amount during the transition. The compression of the flexible interconnect reduces the coupling of energy though the linkage system to the bearing and the cylindrical crank pivot. Thus, in addition to eliminating the bearing at the piston end of the linkage system, the flexible interconnect also reduces the stress on the bearing at the crank end of the linkage system.

The flexible interconnection linkage 512 in the linkage assembly 126 also reduces the noise of the operating percussive massage applicator 100. The effectively silent stretching and compressing of the flexible interconnect when the reciprocation reverses direction at the 6 o'clock and 12 o'clock positions, respectively, eliminates the conventional metal-to-metal interaction that would occur if the linkage system were coupled to the piston 514 with a conventional bearing.

As discussed above, the bullet-shaped applicator head 516 is removably threaded onto the piston 514. The bullet-shaped applicator head may be unscrewed from the piston and replaced with a spherical-shaped applicator head 700, shown in FIG. 20. A spherical-shaped distal end portion 702 of the applicator head extends from an applicator main body portion 704, which corresponds to the main body portion 654 of the bullet-shaped applicator head. The spherical-shaped applicator head includes an engagement portion (not shown) corresponding to the engagement portion 656 of the bullet-shaped applicator head. The spherical-shaped applicator head may be used to apply percussive massage to larger areas of the body to reduce the force on the treated area and to allow the angle of application to be varied.

The bullet-shaped applicator head 516 may also be unscrewed and replaced with a disk-shaped applicator head 720 shown in FIG. 21. A disk-shaped distal end portion 722 of the applicator head extends from an applicator main body portion 724, which corresponds to the main body portion 654 of the bullet-shaped applicator head. The disk-shaped applicator head includes an engagement portion (not shown) corresponding to the engagement portion 656 of the bullet-shaped applicator head. The disk-shaped applicator head may be used to apply percussive massage to a larger area of the body to reduce the force on the treated area.

The bullet-shaped applicator head 516 may also be unscrewed and replaced with a Y-shaped applicator head 740 shown in FIG. 22. A Y-shaped distal end portion 742 of the applicator head extends from an applicator main body portion 744, which corresponds to the main body portion 654 of the bullet-shaped applicator head. The Y-shaped applicator head includes an engagement portion (not shown) corresponding to the engagement portion 656 of the bullet-shaped applicator head. The Y-shaped applicator head includes an applicator base 750. A first finger 752 and a second finger 752 extend from the applicator base and are spaced apart as shown. The two fingers of the Y-shaped applicator head may be used to apply percussive massage to muscles on both sides of the spine without applying direct pressure to the spine.

Power and Control in Percussive Massage Applicators

The portable electromechanical percussive massage applicator 100 may be provided with power and controlled in a variety of manners. FIG. 23 illustrates an exemplary battery control circuit 800, which comprises in part the circuitry mounted on the battery controller PCB 252. In FIG. 23, previously identified elements are numbered with like numbers as before.

The battery control circuit 800 includes the power adapter input jack 254. In the illustrated embodiment, the input power provided to the jack as a DC input voltage of approximately 30 volts DC. Other voltages may be used in other embodiments. The input voltage is provided with respect to a circuit ground reference 810. The input voltage is applied across a voltage divider circuit comprising a first voltage divider resistor 820 and a second voltage divider resistor 822. The resistances of the two resistors are selected to provide a signal voltage of approximately 5 volts when the DC input voltage is present. The signal voltage is provided through a high resistance voltage divider output resistor 824 as a DCIN signal.

The DC input voltage is provided through a rectifier diode 830 and a series resistor 832 to a DC input bus 834. The rectifier diode prevents damage to the circuitry if the polarity of the DC input voltage is inadvertently reversed. The voltage on the DC input bus is filtered by an electrolytic capacitor 836.

The DC input voltage on the DC input bus 834 is provided through a 10-volt Zener diode 840 and a series resistor 842 to the voltage input of a voltage regulator 844. The input of the voltage regulator is filtered by a filter capacitor 846. In the illustrated embodiment, the voltage regulator is a HT7550-1 voltage regulator, which is commercially available from Holtek Semiconductor, Inc., of Taiwan. The voltage regulator provides an output voltage of approximately 5 volts on a VCC bus 848, which is filtered by a filter capacitor 850.

The voltage on the VCC bus is provided to a battery charger controller 860. The controller receives the DCIN signal from the voltage divider output resistor 824. The battery charger controller is responsive to the active high state of the DCIN signal to operate in the manner described below to control the charging of the battery unit 214. When the DCIN signal is low to indicate that the charging voltage is not present, the controller does not operate.

The battery charger controller 860 provides a pulse width modulation (PWM) output signal to the input of a buffer circuit 870, which comprises a PNP bipolar transistor 872 having a collector connected to the circuit ground reference 810. The PNP transistor has an emitter connected to the emitter of an NPN bipolar transistor 874. The bases of the two transistors are interconnected and form the input to the buffer circuit. The two transistor bases are connected to receive the PWM output signal from the controller. The commonly connected bases are also connected to the commonly connected emitters via a base-emitter resistor 876. The collector of the NPN connected to the VCC bus 848.

The commonly connected emitters of the PNP transistor 872 and the NPN transistor 874 are connected to an anode of a protection diode 878. A cathode of the protection diode is connected to the VCC bus 848. The protection diode prevents the voltage on the commonly connected emitters from exceeding the voltage on the VCC bus by more than one forward diode drop (e.g., approximately 0.7 volt). The commonly connected emitters of the two transistors are also connected through a resistor 880 to a first terminal of a coupling capacitor 882. A second terminal of the coupling capacitor is connected to a gate terminal of a power metal oxide semiconductor transistor (MOSFET) 884. In the illustrated embodiment, the MOSFET comprises an STP9527 P-Channel Enhancement Mode MOSFET, which is commercially available from Stanson Technology in Mountain View, California. The gate terminal of the MOSFET is also connected to an anode of a protection diode 886, which has a cathode connected a source (S) terminal of the MOSFET. The protection diode prevents the voltage on the gate terminal from exceeding the voltage on the source terminal by more than the forward diode voltage of the protection diode (e.g., approximately 0.7 volt). The gate terminal of the MOSFET is also connected to the source terminal of the MOSFET by a pull-up resistor 888. The source of the MOSFET is connected to the DC input bus 834.

A drain (D) of the MOSFET 884 is connected to an input node 892 of a buck converter 890. The buck converter further includes an inductor 894 connected between the input node and an output node 896. The output node (also identified as VBAT) is connected to a positive terminal of the battery unit 214. A negative terminal of the battery unit is connected to the circuit ground 810 via a low-resistance current sensing resistor 900. The input node is further connected to a cathode of a free-wheeling diode 902, which has an anode connected to the circuit ground. A first terminal of a resistor 904 is also connected to the input node. A second terminal of the resistor is connected to a first terminal of a capacitor 906. A second terminal of the capacitor is connected to the circuit ground. Accordingly, a complete circuit path is provided from the circuit ground, through the free-wheeling diode, through the inductor, through the battery unit, and through the current sensing resistor back to the circuit ground.

The battery charger controller 860 controls the operation of the buck converter 890 by applying an active low pulse on the PWM output connected to the buffer circuit 870, which responds by pulling down the voltage on the commonly connected emitters of the two transistors 872, 874 to a voltage near the ground reference potential. The low transition to the ground reference potential is coupled through the resistor 880 and the coupling capacitor 882 to the gate terminal of the MOSFET 884 to turn on the MOSFET and couple the DC voltage on the DC input bus 834 to the input node 892 of the buck converter 890. The DC voltage causes current to flow though the inductor 894 to the battery unit 214 to charge the battery unit. When the PWM signal from the battery charger controller is turned off (returned to an inactive high state), the MOSFET is turned off and no longer provides a DC voltage to the input node of the buck converter; however, the current flowing in the inductor continues to flow through the battery unit and back through the free-wheeling diode as the inductor discharges to continue charging the battery unit until the inductor is discharged. The width and repetition rate of the active low pulses generated by the battery charger controller determine the current applied to charge the battery unit in a known manner. In the illustrated embodiment, the PWM signal has a nominal repetition frequency of approximately 62.5 kHz.

The battery charger controller 860 controls the width and repetition rate of the pulses applied to the MOSFET 894 in response to feedback signals from the battery unit 214. A battery voltage sensing circuit 920 comprises a first voltage feedback resistor 922 and a second voltage feedback resistor 924. The two resistors are connected in series from the output node 896 to the circuit ground 810 and are thus connected across the battery unit. A common voltage sensing node 926 of the two resistors is connected to a voltage sensing (VSENSE) input of the controller. The battery charger controller monitors the voltage sensing input to determine the voltage across the battery unit to determine when the battery unit is at or near a maximum voltage of approximately 25.2 volts such that the charging rate should be reduced. In the illustrated embodiment, a filter capacitor 928 is connected from the voltage sensing node to the circuit ground to reduce noise on the voltage sensing node.

As described above, the negative terminal of the battery unit 214 is connected to the circuit ground 810 via the low-resistance current sensing resistor 900, which may have a resistance of, for example, 0.1 ohm. A voltage develops across the current sensing resistor proportional to the current flowing through the battery unit when charging. The voltage is provided as an input to a current sensing (ISENSE) input of the battery charger controller 860 via a high-resistance (e.g., 20,000-ohm) resistor 930. The current sensing input is filtered by a filter capacitor 932. The battery charger controller monitors the current flowing through the battery unit and thus through the current sensing resistor to determine when the current flow decreases as the charge on the battery unit nears a maximum charge. The battery charger controller may also respond to a large current through the battery unit and reduce the pulse width modulation to avoid exceeding a maximum magnitude for the charging current.

The output node 896 of the buck converter 890 is also the positive voltage node of the battery unit 214. The positive battery voltage node is connected to a first terminal 940 of the on/off switch 256. A second terminal 942 of the on-off switch is connected to a voltage output terminal 944, which is identified as VOUT. The voltage output terminal is connected to the first contact 206A of the battery assembly 132. The first contact of the battery assembly engages the first leaf spring contact 204A when the battery assembly is inserted into the battery receiving tray 200. When the switch is closed, the first terminal and the second terminal of the switch are electrically connected to couple the battery voltage to the voltage output terminal. The voltage output terminal is coupled to an output voltage sensing circuit 950, which comprises a first voltage divider resistor 952 and a second voltage divider resistor 954 connected in series between the voltage output terminal and the circuit ground. A common node 956 between the two resistors is connected to a VOUT sensing input of the battery charger controller 860. The common node is also connected to the circuit ground by a Zener diode 958, which clamps the voltage at the common node to no more than 4.7 volts. The resistances of the two resistors are selected such that when the switch is closed and the output voltage is applied to the output terminal, the voltage on the common node and the VOUT sensing input of the controller is approximately 4.7 volts to indicate that the switch is closed and that the battery voltage is being provided to the selected terminal of the battery assembly.

A second contact 206B of the battery assembly 132 is connected to a battery charge (CHRG) output signal of the battery charger controller 860 via a signal line 960. The battery charge output signal may be an analog signal having a magnitude indicative of the charging state of the battery unit 214. In the illustrated embodiment, the battery charge output signal is a pulsed digital signal operating in accordance with the Inter-Integrated Circuit (I2C) protocol, which encodes the charging state of the battery as a series of digital pulses. The second battery assembly contact engages the second leaf spring contact 204B when the battery assembly is inserted into the battery-receiving tray 200.

A third contact 206C of the battery assembly 132 is connected to the negative terminal of the battery unit 214 via a line 970 and is identified as the battery ground (GND) that is provided to the motor control PCB 160 as described below. Note that the battery ground is coupled to the circuit ground by the 0.1-ohm current sensing resistor 900. The current flowing out of the positive terminal of the battery unit to the motor control PCB and back to the negative terminal of the battery unit does not flow through the current sensing resistor. The third battery assembly contact engages the third leaf spring contact 204C when the battery assembly is inserted into the battery-receiving tray 200.

The battery charger controller 860 drives the dual-color LEDs 260 on the battery controller PCB. The controller includes a first output (LEDR) that drives the red-emitting LEDs in the dual-color LEDs and includes a second output (LEDG) that drives the green-emitting LED in the dual-color LEDs. A first current limiting resistor 980 couples the first output to the anodes of the red-emitting LEDs in a first set of three dual-color LEDs. A second current limiting resistor 982 couples the second output to the anodes of the green-emitting LEDs in the first set of three dual-color LEDs. A third current limiting resistor 984 couples the first output to the anodes of the red-emitting LEDs in a second set of three dual-color LEDs. A fourth current limiting resistor 986 couples the second output to the anodes of the green-emitting LEDs in the second set of three dual-color LEDs.

In the illustrated embodiment, the dual-color LEDs 260 are driven with different duty cycles to indicate the present state of charge of the battery unit 214. For example, in a first state, the first output (LEDR) of the controller 860 is driven with a 100 percent duty cycle and the second output (LEDG) of the controller is not driven such that only the red-emitting LEDs are illuminated to indicate that the battery unit needs be charged. In a second state, the first output is driven with a 75 percent duty cycle and the second output is driven with a 25 percent duty cycle such that the resulting perceived color is a mixture of red and green. In a third state, the first output and the second output are both driven with a respective 50 percent duty cycle. In a fourth state, the first output is driven with a 25 percent duty cycle and the second output is driven with a 75 percent duty cycle. In a fifth state, the first output is not driven and the second output is driven with a 100 percent duty cycle such that the color is entirely green to indicate that the battery unit is at or near a fully charged state. The duty cycles at which the two outputs are driven may be interleaved such that the two outputs are not on at the same time. Other than at the first state, the duty cycles are repeated at a rate sufficiently high that the enabled LEDs appear to be on at all times without a perceptible flicker. When the battery controller is in the first state, the battery controller may blink the red-emitting LEDS on and off at a perceptible rate to remind the user that the charge on the battery is low and should be charged before continuing to use the percussive massage applicator 100. In certain embodiments, the first state may be further segmented into two charge ranges. In a first range of charges within the first state, the red LEDs are driven with a constant illumination to indicate that the charge on the charge on the battery unit is low and that the battery unit should be charged soon. In a second range of charges, the red LEDs are blinked to indicate that the charge in the battery unit is very low and that the battery unit should be charged promptly.

FIG. 24 illustrates an exemplary motor controller circuit 1000, which comprises in part the circuitry mounted on the motor controller PCB 160. In FIG. 24, previously identified elements are numbered with like numbers as before. As described above, the battery assembly 132 provides the positive battery output voltage VOUT on the first leaf spring contact 204A of the receiving tray 200 when the battery assembly is inserted into the receiving tray. The positive battery output voltage is identified as VBAT in FIG. 24. The CHRG signal from the battery assembly is provided to the second leaf spring contact 204B when the battery assembly is inserted into the receiving tray. The battery ground (GND) is provided to the third leaf spring contact 204C when the battery assembly is inserted into the receiving tray. The DC voltage, the battery ground and the CHRG signal are coupled via a three-wire cable 1010 to a cable jack 1012. The first plug 170 on the motor controller PCB plugs into the cable jack to receive the DC voltage on a first pin 1020, to receive the CHRG signal on a second pin 1022, and to receive the battery ground (GND) on a third pin 1024. The battery ground (GND) from the third pin of the first plug is electrically connected to a local circuit ground 1026.

The DC voltage (VBAT) on the first pin 1020 of the first plug 170 is filtered by a filter capacitor 1030 connected between the first pin of the first plug and the local circuit ground 1026. The DC voltage is also provided to a first terminal of a current limiting resistor 1032. A second terminal of the current limiting resistor is provided to the voltage input terminal of a voltage regulator 1040. The voltage regulator receives the battery voltage and converts the battery voltage to 5 volts. The 5-volt output of the voltage regulator is provided on a local VCC bus 1042. The local VCC bus is filtered by a filter capacitor 1044, which is connected between the local VCC bus and the local circuit ground. In the illustrated embodiment, the voltage regulator is a 78L05 three-terminal regulator, which is commercially available from a number of manufacturers, such as, for example, National Semiconductor Corporation of Santa Clara, California.

The CHRG signal on the second pin 1022 of the first plug 170 is provided to a charge (CHRG) input of a motor controller 1050 via a series resistor 1052. The charge input to the motor controller is filtered by a filter capacitor 1054. The motor controller receives the 5 volt supply voltage from the VCC bus 1042

The DC voltage from the first pin 1020 of the first plug is also provided directly to a first pin 1060 of the five-pin second plug 172. The second plug 172 is connectable to a second jack 1070 having a corresponding number of contacts. The second jack is connected via a five-wire cable 1072 to the motor 310.

A second pin 1080 of the second plug is a tachometer (TACH) pin, which receives a tachometer signal from the motor 310 indicative of the present angular velocity of the motor. For example, the tachometer signal may comprise one pulse for every revolution of the shaft 312 of the motor or one pulse per partial revolution. The tachometer signal is provided to a first terminal of a first resistor 1084 in a voltage divider circuit 1082. A second terminal of the first resistor is connected to a first terminal of a second resistor 1086 in the voltage divider circuit. A second terminal of the second resistor is connected to the local circuit ground. A common node 1088 between the first and second resistors in the voltage divider circuit is connected to the base of an NPN bipolar transistor 1090. An emitter of the NPN transistor is connected to ground. A collector of the NPN transistor is connected to the VCC bus 1042 via a pull-up resistor 1092. The NPN transistor inverts and buffers the tachometer signal from the motor and provides the buffered signal to a TACH input of the motor controller. The buffered signal varies between +5 volts (VCC) and the local circuit ground potential when the tachometer signal varies between the local circuit ground potential and the DC voltage potential from the battery.

A third pin 1100 of the second plug 172 is a clockwise/counterclockwise (CW/CCW) signal generated by the motor controller 1050 and coupled to the third pin via a current limiting resistor 1102. The state of the CW/CCW signal determines the rotational direction of the motor 310. In the illustrated embodiment, the CW/CCW signal is maintained at a state to cause clockwise rotation; however, the rotation can be changed to the opposite direction in other embodiments.

A fourth pin 1110 of the second plug 172 is connected to the local circuit ground 1026, which corresponds to the battery ground connected to the negative terminal of the battery unit 214 in FIG. 23.

A fifth pin 1120 of the second plug 172 receives a pulse width modulation (PWM) signal generated by the motor controller 1050. The PWM signal is coupled to the fifth pin via a current limiting resistor 1122. The motor 310 is responsive to the duty cycle and the frequency of the PWM signal to rotate at a selected angular velocity. As described below, the motor controller controls the PWM signal to maintain the angular velocity at one of three selected rotational speeds.

The motor controller 1050 has a switch-in (SWIN) input that receives an input signal from the pushbutton switch 162. The pushbutton switch has a first contact connect to the local circuit ground 1026 and has a second contact connected to the VCC bus 1042 via a pull-up resistor 1130. The second contact is also connected to the local circuit ground via a filter capacitor 1132. The second is also connected to the SWIN input of the motor controller. The input signal is held high by the pull-up resistor until the switch contacts are closed by actuating the pushbutton switch. When the switch is actuated to close the contacts, the input signal is pulled to 0 volts (e.g., the potential on the local circuit ground). The filter capacitor reduces the switch contact bounce noise. The motor controller may include internal debounce circuitry to eliminate the effects of the switch contact bounce. The motor controller is initialized in an off-state wherein no PWM signal is provided to the motor 310, and the motor does not rotate. The motor controller is responsive to a first activation of the switch to advance from the off-state to a first on-state wherein the PWM signal provided to the motor is selected to cause the motor to rotate at a first (low) speed. A subsequent activation of the switch advances the motor controller to a second on-state wherein the PWM signal provided to the motor is selected to cause the motor to rotate at a second (medium) speed. A subsequent activation of the switch advances the motor controller to a third on-state wherein the PWM signal provided to the motor is selected to cause the motor to rotate at a third (high) speed. A subsequent activation of the switch returns the motor controller to the initial off-state wherein no PWM signal is provided to the motor and the motor does not rotate. In the illustrated embodiment, the three rotational speeds of the motor are 1,800 rpm (low), 2,500 rpm (medium) and 3,200 rpm (high).

The motor controller 1050 generates a nominal PWM signal associated with the currently selected on-state (e.g., low, medium or high speed). Each on-state corresponds to a selected rotational speed as described above. The motor controller monitors the tachometer signal (TACH) received from the pin 1080 of the five-pin plug 172 via the voltage divider 1082 and the NPN transistor 1090. If the received tachometer signal indicates that the motor speed is below the selected speed, the motor controller adjusts the PWM signal (e.g. increases the pulse width or increases the repetition rate or both) to increase the motor speed. If the received tachometer signal indicates that the motor speed is above the selected speed, the motor controller adjusts the PWM signal (e.g. decreases the pulse width or decreases the repetition rate or both) to decrease the motor speed.

The motor controller 1050 generates a first set of three LED control signals (LEDS1, LEDS2, LEDS3). The first signal (LEDS1) in the first set is coupled via a current limiting resistor 1150 to the anode of the first speed indication LED 166A. The first signal in the first set is activated to illuminate the first speed indication LED when the motor controller is in the first on-state to drive the motor at the first (low) speed. The second signal (LEDS2) in the first set is coupled via a current limiting resistor 1152 to the anode of the second speed indication LED 166B. The second signal in the first set is activated to illuminate the second speed indication LED when the motor controller is in the second on-state to drive the motor at the second (medium) speed. The third signal (LEDS3) in the first set is coupled via a current limiting resistor 1154 to the anode of the third speed indication LED 166C. The third signal in the first set is activated to illuminate the third speed indication LED when the motor controller is in the third on-state to drive the motor at the third (high) speed. In the embodiment of FIG. 24, the cathodes of the speed-indicator LEDs are grounded, and the three LED control signals are applied to the anodes of the respective LEDs such that each LED is illuminated when the respective control signal is active high. In other embodiments described below, the anodes of the indicator LEDs are connected to the VCC bus 1042, and the three LED control signals are applied to the cathodes of the respective LEDs through the respective current limiting resistors such that each LED is illuminated when the respective control signal is active low.

The motor controller 1050 is further responsive to the CHRG signal from the input plug 170. As discussed above, the CHRG signal is generated by the battery charger controller 860 to indicate the state of charge of the battery unit 214. The motor controller determines the present state of charge of the battery unit from the CHRG input signal and displays the state of charge on the five battery charge state LEDs 168A, 168B, 168C, 168D, 168E which are visible through the main body endcap 140. As illustrated the cathode of each battery charge state LED is grounded. The motor controller generates a second set of five LED control signals (LEDC1, LEDC2, LEDC3, LEDC4, LEDC5). The first signal (LEDC1) in the second set is coupled via a current limiting resistor 1170 to the anode of the first charge LED 168A. The first signal in the second set is activated to illuminate the first charge indication LED when the battery unit has a lowest range of charge. The motor controller may blink the first charge indication LED at a perceptible rate to indicate the lowest range of charge. The color (e.g., red) of the light emitted by the first charge LED may differ from the color (e.g., green) of the light emitted by the other LEDS to further indicate the lowest range of charge (e.g., no more than 20 percent of charge remaining). The second signal (LEDC2) in the second set is coupled via a current limiting resistor 1172 to the anode of the second charge indication LED 168B. The second signal in the second set is activated to illuminate the second charge indication LED when the battery unit has a second range of charge (e.g., 21-40 percent of charge remaining). The third signal (LEDC3) in the second set is coupled via a current limiting resistor 1174 to the anode of the third charge indication LED 168C. The third signal in the second set is activated to illuminate the third charge indication LED when the battery unit has a third range of charge (e.g., 41-60 percent of charge remaining). The fourth signal (LEDC4) in the second set is coupled via a current limiting resistor 1176 to the anode of the fourth charge indication LED 168D. The fourth signal in the second set is activated to illuminate the fourth charge indication LED when the battery unit has a fourth range of charge (e.g., 61-80 percent of charge remaining). The fifth signal (LEDC5) in the second set is coupled via a current limiting resistor 1178 to the anode of the fifth charge indication LED 168B. The fifth signal in the second set is activated to illuminate the fifth charge indication LED when the battery unit has a fifth range of charge (e.g., 81-100 percent of charge remaining). It should be understood that the ranges of charge are only approximations and are provided as examples. In the embodiment of FIG. 24, the cathodes of the charge indication LEDs are grounded, and the five LED control signals are applied to the anodes of the respective LEDs such that each LED is illuminated when the respective control signal is active high. In other embodiments described below, the anodes of the five charge indication LEDs are connected to the VCC bus 1042, and the five LED control signals are applied to the cathodes of the respective LEDs through the respective current limiting resistors such that each LED is illuminated when the respective control signal is active low.

The portable electromechanical percussive massage applicator 100 described herein advantageously allows a massage therapist to effectively apply percussion massage over an extended time duration without excessive tiring and without being tethered to an electrical power cord. The reduced noise level of the portable electromechanical percussive massage applicator described herein allows the device to be used in quiet environment such that the person being treated with the device is able to relax and enjoy any ambient music or other soothing sounds provided in the treatment room.

Other Embodiments of Percussive Massage Applicators

FIGS. 25 and 26 illustrate an alternative embodiment of the mechanical structure of a percussive massage device 1200. FIG. 25 is a lower plan view looking up at the motor assembly 300 in the upper body portion 112 with the lower cover 114 and the battery assembly 132 removed. The upper body portion is shown in phantom to focus the drawing on the motor assembly and the linkage. In FIG. 25, the previously described reciprocation assembly 126 with the flexible interconnection linkage 512 between the motor assembly and the piston 514 is replaced with a reciprocation assembly 1210 having a solid linkage 1212 between the motor assembly and a piston 1214. The solid linkage is shown in more detail in an exploded view in FIG. 26. An annular bearing 1220 within a bearing holder 1222 at the proximal end of the solid linkage engages the cylindrical crank pivot 370 of the cylindrical crank 360 as described above. The distal end of the solid linkage includes a pivot bore 1230 that is positioned over a cylindrical protrusion 1234 of a proximal extended portion 1232 of the piston. The pivot bore extends into a bearing recess 1240 of the distal end of the solid linkage. The bearing recess receives a bearing 1242. An unthreaded portion of a pivot screw 1244 extends through the center of the bearing and engages a threaded bore 1246 in the proximal extended portion of the piston. The pivot bore of the solid linkage pivots with respect to the pivot screw to allow the movement of the solid linkage to impose reciprocating motion onto the piston. The distal end of the piston receives a selectably removable applicator head 1248 (shown in phantom lines in FIG. 25). The applicator head may be, for example, one of the applicator heads shown in FIGS. 20-22 or an applicator head having a different configuration.

In many applications of the percussive massage applicator 100, the pressure applied to a particular location on a body may vary depending on the nature of the tissue in the location (e.g., types of muscle, thickness of overlying fat, and the like). If the applicator is being used to apply pressure to a location that is very sensitive, the applied pressure should be relatively small. On the other hand, if the applicator is being used to apply pressure to a large muscle, the applied pressure should be relatively large. Feedback from the person to whom the applicator is being applied will determine an acceptable magnitude of the pressure that provides beneficial massaging without causing undue pain; however, the magnitude of the pressure is not readily quantifiable so that the person wielding the applicator can reproduce the acceptable magnitude of pressure at the same location in subsequent massage sessions or even when returning to the same location in the same massage session. Thus, a need exists for a system and method for quantifying the applied pressure so that the applied pressure can be reproduced.

FIG. 27 illustrates a modified motor controller circuit 1500, which is similar to the motor controller circuit 1000 of FIG. 24. In the motor controller circuit of FIG. 27, many of the components are the same as the components in FIG. 24 and operate in the same manner. The same components in FIG. 27 are labeled with the same element numbers as in FIG. 24.

The modified motor controller circuit 1500 of FIG. 27 includes certain modifications from the motor controller circuit 1000 of FIG. 24. For example, the controller 1050 of FIG. 24 is replaced with a controller 1510 in FIG. 27. In one embodiment, the controller in FIG. 27 is a peripheral interface controller (PIC) such as the Microchip PIC16F677 8-Bit CMOS Microcontroller, which is commercially available from Microchip Technology, Inc., of Chandler, Arizona Other similar controllers from other suppliers may also be used. The controller in FIG. 27 may be the same controller as the controller in FIG. 24; however, as described below, additional input/output terminals are used in the embodiment of FIG. 27.

As a further example, the current limiting resistor 1032 in FIG. 24 is replaced in FIG. 27 with a first Zener diode 1520 and a second Zener diode 1522 connected in series between the VBAT input terminal 1020 and the voltage input terminal (Vin) of a voltage regulator 1040. For example, the two Zener diodes may have voltage values of 3 volts to thereby limit the voltage (e.g., 25.2 volts) from the battery unit 214 to less than 20 volts, which is the maximum input voltage to the voltage regulator.

As further shown in FIG. 27, the pulse width modulation signal (now labeled "PWM_C") from the controller 1500 is not connected directly to the PWM input of the motor 310 via the current limiting resistor 1122. Rather, the PWM_C signal passes through the current limiting resistor as before and is connected to the base of an NPN bipolar transistor 1530. The collector of the transistor is connected to the local circuit ground. The base of the transistor is also connected to the local circuit ground via a pulldown resistor 1532. The collector of the transistor is connected to the fifth pin 1120 of the second plug 172 and is thus connected to the motor via the second jack 1070 and the five-wire cable 1072. The collector of the transistor is also connected to the VCC bus 1042 via a pullup resistor 1534. The PWM signal functions as before except that the PWM_C signal from the controller is inverted and buffered by the transistor.

The modified motor controller circuit 1500 of FIG. 27 further includes a load current sensing circuit 1550. The load current sensing circuit comprises a current sensing resistor 1552 having a first terminal connected to the fourth pin 1110 of the second plug 172 and having a second terminal connected the local circuit ground 1026. Thus, rather than the return current from the motor 310 flowing directly to the local circuit ground as in FIG. 24, the return current in FIG. 27 flows through the current sensing resistor before reaching the local circuit ground. Accordingly, a voltage develops across the first terminal of the current sensing resistor with respect to the local circuit ground. In the illustrated embodiment, the current sensing resistor is a precision resistor having a resistance of approximately 50 milliohms and a precision of 1% or better. The voltage on the first terminal of the current sensing resistor is proportional to the current flowing through the current sensing resistor. For example, when the current flowing through the current sensing resistor has a magnitude of 1 ampere, the voltage on the first terminal of the current sensing resistor has a magnitude of 50 millivolts. Thus, the voltage on the first terminal of the current sensing resistor can be monitored to determine the instantaneous current flowing from the ground (current return) of the motor to the local circuit ground.

A first filter capacitor 1560 (e.g., a 100,000-picofarad capacitor) is connected across the current sensing resistor 1552 from the first terminal of the current sensing resistor to the local circuit ground. A first filter resistor 1562 (e.g., a 100,000-ohm resistor) is connected from the first terminal of the current sensing resistor to an analog input pin of the controller 1510. The analog input pin is labeled as "LOAD" in FIG. 27 to indicate that the input signal received on the input pin represents the load current of the motor 310. A second filter capacitor 1564 (e.g., a 100,000 picofarad capacitor) and a third filter capacitor 1566 (e.g., a 100-microfarad electrolytic capacitor) are connected from the analog (LOAD) input pin to the local circuit ground. A second filter resistor 1568 (e.g., a 300,000-ohm resistor) is also connected from the analog input pin to the local circuit ground. Because the motor 310 is driven by pulse width modulation, the current flowing from the motor to the local circuit ground via the current sensing resistor 1552 comprises a sequence of current pulses, which are sensed by the current sensing resistor to generate a corresponding sequence of voltage pulses. The two filter capacitors and the two filter resistors operate as a low-pass filter to convert the sequence of voltage pulses into a DC voltage signal having a magnitude that varies slowly as the average magnitude of the current pulses vary. The voltage developed across the second filter resistor and the second and third filter capacitors is provided to the analog input pin of the controller. Accordingly, a voltage directly proportional to the average motor load current is applied to the LOAD input pin of the controller.

In the embodiment of FIG. 27, the cathodes of the five charge-indicating LEDs 168A-E are connected to the respective control signals LEDC1-5 of the controller 1510 via the respective current-limiting resistors 1170, 1172, 1174, 1176, 1178, respectively. The anode of each charge-indicating LED is connected to the VCC bus 1042. Each charge-indicating LED is illuminated when the respective control signal is active low to allow current to flow through the LED.

In the embodiment of FIG. 27, the cathodes of the three speed-indicating LEDs 166A-C are connected to the respective control signals LEDS1-3 of the controller 1510 via the respective current-limiting resistors 1150, 1152, 1154, respectively. The anode of each speed-indicating LED is connected to the VCC bus 1042. Each speed-indicating LED is illuminated when the respective control signal is active low to allow current to flow through the LED.

The controller 1500 in FIG. 27 generates three additional output signals LEDP1, LEDP2 and LEDP3 on respective output pins. The LEDP1 output signal is connected via a current limiting resistor 1570 to the cathode of a first power-indicator LED 1572A, which has an anode connected to the VCC bus 1042. The first power-indicator LED is illuminated when the LEDP1 output signal is active low. The LEDP2 output signal is connected via a current limiting resistor 1574 to the cathode of a second power-indicator LED 1572B, which has an anode connected to the VCC bus. The second power-indicator LED is illuminated when the LEDP2 output signal is active low. The LEDP3 output signal is connected via a current limiting resistor 1576 to the cathode of a third power-indicator LED 1572C, which has an anode connected to the VCC bus. The third power-indicator LED is illuminated when the LEDP3 output signal is active low. As described below, the first, second and third power-indicator LEDs are selectively illuminated in response to the magnitude of the current sensed by the current sensing resistor 1552. In the illustrated embodiment, the cathodes of the respective power-indicator LEDs are driven with respective active low signals. In other embodiments, the cathodes may be connected to the VCC bus and the anodes may be driven with active low output signals from the controller such as described above with respect to LEDs in the embodiment of FIG. 24. The three additional LEDs are shown on a perspective view of the modified percussive massage device 1200 in FIG. 28 and in a perspective view of a modified motor control printed circuit board 1580 in FIG. 29. In FIG. 28, the motor enclosure 120 of the previously describe embodiment is replaced with a modified motor enclosure 1582, which is shorter and which has a larger diameter to accommodate a motor (not shown) having a different configuration. Also, the fingertip opening 234 in the lower body 114 is eliminated.

Operation of the Percussive Massage Applicator

The magnitude of the load current flowing through the sensing resistor 1552 is related to the pressure applied to the massage applicator 100 to force the applicator head 516 of the massage applicator against a location on a body or against another obstacle. For example, when the applicator head is allowed to reciprocate freely, the load current will be a minimal amount of current needed to turn the motor 310 and to reciprocate the applicator head and to turn and reciprocate the components coupling the output shaft of the motor to the applicator head. In contrast, when the applicator head is pressed forcibly against a location on a body or against another obstacle, the motor requires additional current to maintain a selected rotational speed at the increased pressure. Thus, in the illustrated embodiment, the magnitude of the load current through the motor is measured and is compared to ranges of load current corresponding to different magnitudes of applied force to determine the instantaneous load current. The measurement and the comparison features are described below.

The motor control functions and the display of the operating speed are performed within the controller 1510 correspond to the functions described above with respect to the controller 1050 of FIG. 27. FIG. 30 illustrates a flowchart 1600 of the operation of the pressure measurement and display functions of the embodiment of FIG. 27.

The operation of the controller 1510 starts with a power sequence in an activity block 1610 wherein the controller starts operating when power is first applied via the on/off switch 256 on the battery assembly 132. The controller first performs functions defined by internal programmable memory to initialize various internal settings in a system initialization activity block 1612.

After the system initialization, the controller 1510 advances to an input/output (I/O) port initialization activity block 1614 wherein the controller initializes the input/output (I/O) ports. As indicated above, in the illustrated embodiment, the controller comprises a Microchip PIC16F677 8-Bit CMOS Microcontroller. The illustrated controller has 18 I/O pins and each pin is configurable to perform many different functions. In the initialization activity block, the pins are configured in accordance with the intended functionality. For example, the LEDS1, LEDS2, LEDS3, LEDC1, LEDC2, LEDC3, LEDC4, LEDC5, LEDP1, LEDP2 and LEDP3 pins are configured as output pins. The PWM_C pin is configured as a pulse width modulation output pin, which is supported by internal logic within the controller to generate a PWM signal at a selected frequency and a selected duty cycle. The CW/CCW pin is configured as an output pin. The LOAD pin is configured as an analog input pin to receive the voltage having a magnitude corresponding to the sensed value of the motor current. The TACH pin is configured as a digital input pin to receive the tachometer pulses from the motor 310. The CHRG pin is configured as an I2C to receive an input sequence from the battery controller PCB 252 having a digital value representing the charge state of the battery unit 214. The SWIN pin is configured as a digital input to receive the high or low state of the central pushbutton switch 162.

After initializing the I/O pins in the block 1614, the controller 1510 advances to a motor speed state set-to-zero activity block 1616 wherein the controller sets the desired motor speed state to 0 (e.g., off). The controller also applies control signals to the internal PWM logic to cause the PWM logic to discontinue sending PWM signals to the PWM_C output pin. On the initial pass through the activity block after initially powering up, the controller may have already set the motor speed state to zero during the initialization process.

After setting the motor speed state to 0, the controller 1510 advances to a display activity block 1620 wherein the controller selectively activates the signals on the LEDC1-5 output pins to display the battery charge via the battery charge indicator LEDs 168A-E. The controller obtains the battery charge information from the battery controller PCB 252 via the I2C signal on the CHRG input pin.

After activating the battery charge LEDs, the controller 1510 advances to a speed switch reading activity block 1622 wherein the controller reads the digital value on the SWIN input pin to determine the state of the pushbutton switch 162, which functions as a motor speed state selection switch as described above. A digital value of 0 indicates that the switch has been activated by a user. A digital value of 1 indicates that the switch has not been activated. The controller may be programmed with an internal debounce routine to assure that the controller only responds once to each activation of the pushbutton switch.

After reading the value on the SWIN input pin, the controller 1510 advances to a decision block 1624 in which the controller determines whether the pushbutton (speed change) switch 162 is active (e.g., the digital value on the SWIN pin is low). If the switch is inactive, the controller returns to the display activity block 1620 and continues to display the battery charge as described above and continues to read the value on the SWIN input pin in the activity block 1622. The controller will continue to loop to display the battery charge and read the pushbutton switch until the value on the SWIN input pin becomes active low.

If the pushbutton switch 162 is active when the controller 1510 evaluates the state of the switch in the decision block 1624, the controller advances to a speed change activity block 1630 wherein the controller increments the motor speed state from 0 to 1 and sets the internal PWM logic to output pulses on the PWM_C output pin to drive the motor 310 at the slowest motor speed (e.g., 1,800 rpm in the illustrated embodiment). Within the speed change activity block, the controller also activates the LEDS1 signal to cause the first motor speed indicator LED 168A to illuminate.

After setting the motor speed to the lowest level in the block 1630, the controller 1510 advances to a block 1632 wherein the controller performs a calibration procedure in which the controller first determines a no-load current magnitude INO-LOAD when no pressure is applied to the applicator head 516. The steps within the calibration procedure block are described in more detail below with respect to FIG. 31. As described below, the controller returns from the calibration procedure with a calibration flag set if the calibration procedure completes successfully and returns from the calibration procedure with the calibration flag reset (cleared) if the calibration procedure does not complete successfully.

After completing the calibration procedure in the block 1632, the controller 1510 advances to a decision block 1640 wherein the controller tests the status of the calibration flag. If the calibration flag is set, the controller advances to an activity block 1650. Otherwise, the controller skips the activity block 1650 and advances to an activity block 1660.

The activity block 1650 is a current measurement and pressure display activity block wherein the controller inputs the analog voltage value on the LOAD input pin representing the magnitude of the average current through the current sensing resistor 1552, determines a load current magnitude, and selectively activates one of the pressure indicator LEDs 1572A, 1572B, 1572C to indicate a range of pressure being applied to the applicator head 516. The steps within the current measurement and pressure display block are described in more detail below with respect to FIG. 32. The controller than advances to the activity block 1660.

The activity block 1660 is a charge display activity block wherein the controller 1510 inputs the digital value on the CHRG input pin and selectively activates the signals on the LEDC1-5 output pins to display the battery charge via the battery charge indicator LEDs 168A-E.

After displaying the battery charge in the charge display activity block 1660, the controller advances to a speed switch reading activity block 1662 wherein the controller reads the digital value on the SWIN input pin to determine the state of the pushbutton switch 162 as described above for the speed switch reading activity block 1622.

After reading the value on the SWIN input pin, the controller 1510 advances to a decision block 1664 in which the controller determines whether the pushbutton (speed change) switch 162 is active (e.g., the digital value on the SWIN pin is low).

If the switch is inactive when evaluated in the decision block 1664, the controller 1510 returns to the decision block 1640 where the controller again determines whether the calibration flag is set or clear. If the calibration flag is set, the controller then displays the new current magnitude in the pressure display activity block 1650, displays the battery charge in the charge display activity block 1660, reads the pushbutton switch in the speed switch reading activity block 1662, and checks the reading in the decision block 1664 to determine whether the switch is active. Otherwise, the controller skips the block 1650 and performs the steps in the blocks 1660, 1662 and 1664. The controller remains in the five-block loop (calibration flag set) or four-block loop (calibration flag clear) until the pushbutton switch is activated. In the illustrated embodiment, the functions performed in the loop are timed such that the current is measured approximately eight times per second. The timing may be accomplished by software delays, by implementing a countdown timer, or by other known methods for controlling loop timing. Until the pushbutton switch is activated, the controller will remain in the loop as long as power is being provided from the battery assembly 132.

If the pushbutton switch 162 is active when the controller 1510 evaluates the state of the switch in the decision block 1664, the controller advances to a speed change activity block 1670 wherein the controller increments the motor speed state by 1. The controller then advances to a decision block 1672 wherein the controller determines whether the new motor speed state is greater than 3. If the motor speed state is greater than 3, the controller returns to the motor speed state set-to-zero activity block 1616 wherein the controller sets the desired motor speed state to 0 (e.g., off). The controller also applies control signals to the internal PWM logic to cause the PWM logic to discontinue sending PWM signals to the PWM_C output pin. The controller also deactivates the signals on the LEDS1, LEDS2 and LEDS3 output pins such that all of the speed indicator LEDs 168A, 168B and 168C are turned off. The controller then continues in the four-block loop comprising the blocks 1616, 1620, 1622 and 1624 until the pushbutton switch is again activated to restart the motor 310.

If the new motor speed state is no more than 3 when the controller 1510 reaches the decision block 1672, the controller advances to a motor speed setting block 1680 wherein the controller sets the motor speed to a value corresponding to the new motor speed state. If the new motor speed state is 2, the controller applies control signals to the internal PWM logic to cause the PWM logic to send PWM signals to the PWM_C output pin to cause the motor 310 to rotate at the medium speed (e.g., 2,500 rpm in the illustrated embodiment). Within the motor speed setting block, the controller also deactivates the previously active signal on the LEDS1 output pin and activates the signal on the LEDS2 output pin to turn on the second speed indicator LED 168B. If the new motor speed state is 3, the controller applies control signals to the internal PWM logic to cause the PWM logic to send PWM signals to the PWM_C output pin to cause the motor 310 to rotate at the high speed (e.g., 3,200 rpm in the illustrated embodiment). The controller deactivates the previously active signal on the LEDS2 output pin and activates the signal on the LEDS3 output pin to turn on the third speed indicator LED 168C.

After setting the new motor speed in the motor speed setting block 1680, the controller 1510 returns to the decision block 1640 wherein the controller checks the status of the calibration flag and then performs either the five-block loop (calibration flag set) or the four-block loop (calibration flag clear) as described above. The controller remains in the five-block loop or the four-block loop until the switch is activated. The controller repeats the actions in the loop approximately 8 times per second until the pushbutton switch is activated or until power is no longer being provided from the battery assembly 132.

FIG. 31 illustrates steps within the perform calibration procedure block 1632 of FIG. 30. The calibration procedure is performed when the user initially activates the central pushbutton (speed change) switch 162 to cause the controller 1510 to turn on the motor 310 and set the speed at the lowest level (level 1) as described above with respect to FIG. 30. The documentation with the percussive massage device 100 instructs the user that calibration is performed when power is initially applied and further instructs the user to not activate the speed selection switch to increase the speed and to not apply pressure against the applicator head 516.

In a first activity block 1700, the controller 1510 activates the power indication LEDs 1572A, 1572B, 1572C in a flashing pattern to alert the user that the calibration procedure is being performed. The pattern may be a counting pattern with the illuminated LEDs representing a binary count, a shifting pattern wherein one LED is illuminated at a time or another selected pattern that changes to indicate the calibration procedure is active. While continuing to flash the LEDs, the controller advances to an activity block 1702 wherein the controller inputs the analog voltage value on the LOAD input pin representing the magnitude of the average current through the current sensing resistor 1552. The controller saves (records) the initial current magnitude and advances to a decision block 1704 wherein the controller determines whether the speed selection switch 162 has been activated by the user during the calibration procedure. If the speed selection switch has been activated, the controller exits the calibration procedure without completing the calibration process. When exiting the calibration procedure early, the controller resets (clears) the calibration flag in an activity block 1706, turns of the LEDs in an activity block 1708 and then exits the calibration procedure via a block 1710.

If the user does not activate the speed selection switch 162 during the calibration procedure, the controller 1510 advances from the decision block 1704 to a decision block 1720 wherein the controller determines whether 40 current samples have been saved, which represents approximately 5 seconds of sampling at approximately 8 samples per second. If the 40 samples have not been saved, the controller returns to the activity block 1702 wherein the controller inputs the next sample and then checks to determine whether the speed selection switch has been activated. The controller continues in this current sampling loop until 40 current samples are saved or until the user interrupts the calibration procedure by activating the speed selection switch.

When the controller 1510 determines that 40 current samples have been saved (recorded), the controller advances from the decision block 1720 to an activity block 1722 wherein the controller averages the 40 current samples to determine an average current. Then, in a decision block 1722, the controller determines whether the average current exceeds 1,000 milliamperes. If the user has complied with the calibration procedure instructions and has not applied pressure against the applicator head 516 during the calibration procedure, the average current should not exceed 1,000 milliamperes. If the average current exceeds 1,000 milliamperes, the controller advances to the activity block 1706 to reset (clear) the calibration flag, turns off the flashing LEDs in the block 1708 and exits the calibration procedure via the block 1710.

If the average of the current samples is no more than 1,000 milliamperes, the controller 1510 advances from the decision step 1730 to an activity block 1732 wherein the controller saves the average current as the no-load current value INO-LOAD. The no-load current value is used in the pressure measurement steps described below with respect to FIG. 32. The controller sets the calibration flag to indicate that the calibration procedure was successful and that the no-load current value can be used in the current measurement and pressure display procedure 1650 as described below.

After saving the no-load current magnitude and setting the calibration flag in the block 1732, the controller 1510 advances to an activity block 1734 wherein the controller activates the three pressure indicator LEDs 1572A, 1572B, 1572C together for approximately one second to inform the user that the calibration procedure was completed successfully. Alternatively, the controller may indicate successful completion of the calibration procedure by multiple flashes (e.g., two flashes) of the three LEDs together. In a further alternative, the three LEDs may be activated in a selected sequence to indicate the successful completion of the calibration procedure. The controller than advances to the activity block 1708 to turn off the LEDs and then exits the calibration procedure via the block 1710.

The procedure 1650 of inputting voltages, determining current magnitudes and displaying pressure is illustrated in more detail in FIG. 32. In a first activity block 1800, the controller 1510 inputs a current magnitude sample by measuring the voltage across the current sensing resistor 1552 as described above. The controller then advances to an activity block 1802 wherein the controller calculates a rolling average IAVG of the last eight current samples. The first seven times through the overall measurement loop, the controller may average less than eight samples; however, the full averaging will occur after the percussive massage device 100 has been operating for at least one second.

After generating the average current in the block 1802, the controller 1510 advances to an activity block 1804 wherein the controller calculates a current difference ΔI between the average current IAVG (determined in the block 1802) and the no-load current INO-LOAD (determined in the calibration procedure 1616 of FIG. 31). After calculating the current difference ΔI, the controller advances to a branching decision block 1806 wherein the controller branches to one of three pressure display routines based on the selected speed level.

If the selected speed is at level 1 (low speed), the controller 1510 branches from the branching decision block 1806 to a first pressure display routine 1810. The first pressure display routine includes a respective first decision block 1812, a respective second decision block 1814, and a respective third decision block 1816.

If the selected speed is at level 2 (medium speed), the controller 1510 branches from the branching decision block 1806 to a second pressure display routine 1820. The second pressure display routine includes a respective first decision block 1822, a respective second decision block 1824, and a respective third decision block 1826.

If the selected speed is at level 3 (high speed), the controller 1510 branches from the branching decision block 1806 to a third pressure display routine 1830. The third pressure display routine includes a respective first decision block 1832, a respective second decision block 1834, and a respective third decision block 1836.

Within the first pressure display routine 1810, the controller 1510 first determines in the respective first decision block 1812 whether the difference ΔI between the average current IAVG and the no-load current INO-LOAD is less than 300 milliamperes. If the difference is less than 300 milliamperes, the controller advances to an activity block 1840 wherein the controller turns off all of the pressure indicator LEDs 1572A, 1572B, 1572C to indicate that no pressure or only a small amount of pressure is being applied to the application head 516. For example, in one embodiment, an applied pressure of less than 0.1 kilogram will not increase the average current over the no-load current by 300 milliamperes at the first (low) speed level.

If the controller 1510 determines in the respective first decision block 1812 that the difference ΔI between the average current and the no-load current is at least 300 milliamperes, the controller advances to the respective second decision block 1814 wherein the controller determines whether the difference ΔI between the average current and the no-load current is less than 600 milliamperes. If the difference is less than 600 milliamperes, the controller advances to an activity block 1842 wherein the controller turns on the first pressure indicator LED 1572A to indicate that the pressure is in a first pressure range. For example, in one embodiment, an applied pressure in a first pressure range of approximately 0.1 kilogram to 0.5 kilogram will cause an average load current in a range of approximately 300 milliamperes to approximately 599 milliamperes greater than the no-load current at the first (low) speed level.

If the controller 1510 determines in the respective second decision block 1814 that the difference ΔI between the average current and the no-load current is at least 600 milliamperes, the controller advances to the respective third decision block 1816 wherein the controller determines whether the difference ΔI between the average current and the no-load current is less than 900 milliamperes. If the difference is less than 900 milliamperes, the controller advances to an activity block 1844 wherein the controller turns on the second pressure indicator LED 1572B to indicate that the pressure is in a second pressure range. For example, in one embodiment, an applied pressure in a second pressure range of approximately 0.5 kilogram to approximately 1.5 kilograms will cause an average load current in a range of approximately 600 milliamperes to approximately 899 milliamperes greater than the no-load current at the first (low) speed level. In another example, the applied pressure in the second pressure range is from approximately 0.5 kilogram to approximately 2.5 kilograms.

If the controller 1510 determines in the respective third decision block 1816 that the difference ΔI between the average current and the no-load current is at least 900 milliamperes, the controller advances to an activity block 1846 wherein the controller turns on the third pressure indicator LED 1572C to indicate that the pressure is in a third pressure range. For example, the applied pressure in the third pressure range is greater than 1.5 kilograms. In another example, in one embodiment, an applied pressure in a third pressure range greater than approximately 2.5 kilograms will cause an average load current at least 900 milliamperes greater than the no-load current at the first (low) speed level.

Within the second pressure display routine 1820, the controller 1510 first determines in the respective first decision block 1822 whether a difference ΔI between the average current and the no-load current is less than 600 milliamperes. If the difference is less than 600 milliamperes, the controller advances to the activity block 1840 wherein the controller turns off all of the pressure indicator LEDs 1572A, 1572B, 1572C to indicate that no pressure or only a small amount of pressure is being applied to the application head 516. For example, in one embodiment, an applied pressure of less than 0.1 kilogram will not increase the average current over the no-load current by 600 milliamperes at the second (medium) speed level.

If the controller 1510 determines in the respective first decision block 1822 that the difference ΔI between the average current and the no-load current is at least 600 milliamperes, the controller advances to the respective second decision block 1824 wherein the controller determines whether the difference ΔI between the average current and the no-load current is less than 900 milliamperes. If the difference is less than 900 milliamperes, the controller advances to the activity block 1842 wherein the controller turns on the first pressure indicator LED 1572A to indicate that the pressure is in a first pressure range. For example, in one embodiment, an applied pressure in the first pressure range of approximately 0.1 kilogram to 0.5 kilogram will cause an average load current in a range of approximately 600 milliamperes to approximately 899 milliamperes greater than the no-load current at the second (medium) speed level.

If the controller 1510 determines in the respective second decision block 1824 that the difference ΔI between the average current and the no-load current is at least 900 milliamperes, the controller advances to the respective third decision block 1826 wherein the controller determines whether the difference ΔI between the average current and the no-load current is less than 1,200 milliamperes. If the difference is less than 1,200 milliamperes, the controller advances to the activity block 1844 wherein the controller turns on the second pressure indicator LED 1572B to indicate that the pressure is in a second pressure range. For example, in one embodiment, an applied pressure in the second pressure range of approximately 0.5 kilogram to approximately 1.5 kilograms will cause an average load current in a range of approximately 900 milliamperes to approximately 1,199 milliamperes greater than the no-load current at the first (medium) speed level. In another example, the applied pressure in the second pressure range is from approximately 0.5 kilogram to approximately 2.5 kilograms.

If the controller 1510 determines in the respective third decision block 1826 that the difference ΔI between the average current and the no-load current is at least 1,200 milliamperes, the controller advances to the activity block 1846 wherein the controller turns on the third pressure indicator LED 1572C to indicate that the pressure is in a third pressure range. For example, in one embodiment, the applied pressure in the third pressure range is greater than 1.5 kilograms. In another example, an applied pressure in the third pressure range greater than approximately 2.5 kilograms will cause an average load current at least 1,200 milliamperes greater than the no-load current at the second (medium) speed level.

Within the third pressure display routine 1830, the controller 1510 first determines in the respective first decision block 1832 whether a difference ΔI between the average current and the no-load current is less than 900 milliamperes. If the difference is less than 900 milliamperes, the controller advances to the activity block 1840 wherein the controller turns off all of the pressure indicator LEDs 1572A, 1572B, 1572C to indicate that no pressure or only a small amount of pressure is being applied to the application head 516. For example, in one embodiment, an applied pressure of less than 0.1 kilogram will not increase the average current over the no-load current by 900 milliamperes at the third (high) speed level.

If the controller 1510 determines in the respective first decision block 1832 that the difference ΔI between the average current and the no-load current is at least 900 milliamperes, the controller advances to the respective second decision block 1834 wherein the controller determines whether the difference ΔI between the average current and the no-load current is less than 1,200 milliamperes. If the difference is less than 1,200 milliamperes, the controller advances to the activity block 1842 wherein the controller turns on the first pressure indicator LED 1572A to indicate that the pressure is in a first pressure range. For example, in one embodiment, an applied pressure in the first pressure range of approximately 0.1 kilogram to 0.5 kilogram will cause an average load current in a range of approximately 900 milliamperes to approximately 1,199 milliamperes greater than the no-load current at the third (high) speed level.

If the controller 1510 determines in the respective second decision block 1834 that the difference ΔI between the average current and the no-load current is at least 1,200 milliamperes, the controller advances to the respective third decision block 1836 wherein the controller determines whether the difference ΔI between the average current and the no-load current is less than 1,500 milliamperes. If the difference is less than 1,500 milliamperes, the controller advances to the activity block 1844 wherein the controller turns on the second pressure indicator LED 1572B to indicate that the pressure is in a second pressure range. For example, in one embodiment, an applied pressure in the second pressure range of approximately 0.5 kilogram to approximately 1.5 kilograms will cause an average load current in a range of approximately 1,200 milliamperes to approximately 1,499 milliamperes greater than the no-load current at the first (medium) speed level. In another example, the applied pressure in the second pressure range is from approximately 0.5 kilogram to approximately 2.5 kilograms.

If the controller 1510 determines in the respective third decision block 1836 that the difference ΔI between the average current and the no-load current is at least 1,500 milliamperes, the controller advances to the activity block 1846 wherein the controller turns on the third pressure indicator LED 1572C to indicate that the pressure is in a third pressure range. For example, in one embodiment, the applied pressure in the third pressure range is greater than 1.5 kilograms. In another example, an applied pressure in the third pressure range greater than approximately 2.5 kilograms will cause an average load current at least 1,500 milliamperes greater than the no-load current at the third (high) speed level.

By first establishing a no-load current magnitude and then determining the applied pressure based on the difference between the measured current and the no-load current, the pressure indications produced by individual units will be similar. The no-load currents may vary from unit to unit because of differences in friction levels within the reciprocating mechanism for example; however, the differences in current caused by applied pressure will be similar. Thus, the pressure indications provided by different units will be similar.

In the embodiment illustrated in FIG. 32, each of the pressure indicator LEDs 1572A, 1572B, 1572C is illuminated only for the specific range of current differences for the selected motor speed. Accordingly, as the applied pressure increases, the three pressure indicator LEDs illuminate such that only one LED is illuminated at any time (other than during the calibration procedure 1616 described above).

In an alternative embodiment illustrated by a flowchart 1850 in FIG. 33, the first pressure indicator LED 1572A is illuminated for the first active range of applied pressures and remains illuminated for the second and third ranges of applied pressures. Similarly, the second pressure indicator LED 1572B is illuminated for the second range of applied pressures and remains illuminated for the third range of applied pressures. The third pressure indicator LED 1572C is illuminated only for the third range of applied pressures. Thus, when the applied pressure increases to the higher ranges in the alternative embodiment, the pressure indicator LEDs provide a cumulative lighting effect rather than a discrete effect as in the illustrated embodiment. In FIG. 33, the modified sequencing of the pressure indicator LEDs is implemented by having the controller 1510 exit the block 1846 and advance to the block 1844 and by having the controller exit the block 1844 and advance to the block 1842. The controller exits the procedure from the block 1842 as previously described. Thus, when the controller activates the third pressure indicator to indicate the highest applied pressure range, the controller also activates the second pressure indicator LED and the first pressure indicator LED before exiting the modified procedure. When the controller activates the second pressure indicator to indicate the middle applied pressure range, the controller also activates the first pressure indicator LED before exiting the modified procedure. When the controller activates the first pressure indicator LED to indicate the lowest applied pressure range, the controller only activates the first pressure indicator LED before exiting the modified procedure.

The flowcharts in FIGS. 32 and 33 represent an implementation of the decision process for determining which, if any, of pressure indicator LEDs 1572A, 1572B, 1572C to activate. The decision process may also be implemented in other manners, such as, for example, lookup tables or the like.

In the illustrated embodiment, the differences between the average current and the no-load current are characterized in four ranges for each motor speed, which results in the illumination of no pressure indicator LEDs at the lowest range of current differences caused by little or no applied pressure; the illumination of the first pressure indicator LED 1572A at a second range of current differences caused by applied pressure in a first range; the illumination of the second pressure indicator LED 1572B at a third range of current differences caused by applied pressure in a second range; and the illumination of the third pressure indicator LED 1572C at a fourth range of current differences caused by applied pressure in a third range. In other embodiments, the current differences may be divided into more than four ranges (e.g., eleven current ranges) and more pressure indicators (e.g., ten pressure indicator LEDs) may be used to indicate the additional ranges of pressure applied against the applicator head.

In further alternative embodiments, the signals representing the pressure ranges may be encoded (e.g., binary encoded) such that three LEDs may be indicate up to seven active pressure ranges. In such an embodiment, a condition of no LEDs being illuminated represents zero or near zero pressure applied to the applicator head; and each of the seven possible combinations of one or more illuminated LEDs represents a respective one of seven pressure ranges. The encoded signals may also be used to control a numeric display (e.g., an LCD) of pressure ranges.

The above-described relationships between particular current magnitudes and particular pressure ranges are examples of ranges. The specific relationship between the ranges of measured current and the ranges of applied pressure may vary from unit to unit.

In the illustrated embodiment, the calibration procedure to establish the no-load current INO-LOAD is performed at the lowest speed (level 1). The same no-load current is used to determine the pressure at all three operational speeds as described above. In alternative embodiments, a separate no-load current may be established for each of the three operational speeds. In the alternative embodiment, the current difference is calculated based on the no-load current for the selected speed.

As illustrated in FIG. 35, in certain embodiments, a modified percussive massage device 1900 may be used with a wireless remote device 1910 (e.g., a smartphone, a smart watch, a laptop, a notebook computer, a tablet, a smart glasses, a headset, etc.), which obtains and stores data representing the use of the percussive massage device. FIG. 34 illustrates a further modified motor controller circuit 1920, which is similar to the motor controller circuit 1500 of FIG. 27 except that the motor controller circuit of FIG. 34 includes a Bluetooth transceiver (BT XCVR) 1930 (referred to herein as a Bluetooth interface), which is coupled to selected LED driver outputs of the controller 1510. The Bluetooth transceiver is an example of a radio frequency wireless communication device that may be used. In particular, the Bluetooth interface includes a plurality of input/output (I/O) ports (e.g., six I/O ports), which are configured as input ports. The six input ports are identified as I0, I1, I2, I3, I4 and I5. The first port (I0) is connected to the LEDS1 output of the controller. The second port (I1) is connected to the LEDS2 output of the controller. The third port (I2) is connected to the LEDS3 output of the controller. The fourth port (I3) is connected to the LEDP1 output of the controller. The fifth port (I4) is connected to the LEDP2 output of the controller. The sixth port (I5) is connected to the LEDP3 output of the controller.

The Bluetooth interface 1930 receives "AT" command signals from the remote control device 1910 by signals sent from the remote control device to the Bluetooth interface. For example, sending an "AT+PIO??" command to the Bluetooth interface causes the Bluetooth interface to respond with three hexadecimal characters in which the status (e.g., a digital "1" or a digital "0") of each of twelve input/output pins is encoded as a bit in one of the hexadecimal characters. The remote control device decodes the bits corresponding to the input pins I1-I5 to determine the speed and the pressure value (e.g., current magnitude range) when the command is sent to the Bluetooth interface.

The remote control device 1920 periodically sends the "AT+PIO??" command to the Bluetooth interface to obtain the speed and pressure readings. The remote control device stores the readings in memory along with the date and time of the readings and along with further information such as the identity of the person receiving the percussive massage. Thus, the remote control device is enabled to maintain a history of the percussive massage provided to a person. The person may retrieve the saved information to obtain the speed, pressure and duration of previous treatments. Based on the qualitative experience from a previous treatment, the person may repeat the previous treatment or modify one or more of the parameters (e.g., speed, pressure, duration) for a current treatment to attempt to obtain an improved experience.

The foregoing is shown in FIG. 36, which illustrates a flowchart 1950 of the operation of the remote control device (e.g., smartphone) 1900 of FIG. 35 and the further modified motor controller circuit 1910 of FIG. 34 within the percussive massage device 100. In a first activity block 1960, the remote control device establishes Bluetooth communication with the modified motor controller circuit such that the remote control device is paired with the percussive massage device. After establishing communication, the remote control device sends a status request command to the modified motor controller circuit in an activity block 1962. The remote control device receives the status information from the modified motor controller circuit in an activity block 1964. In an activity block 1966, the remote control device parses the status information to separate the six bits representing the motor speed and the pressure. In an activity block 1970, the remote control device displays the current motor speed and pressure. The remote control device stores the motor speed and the pressure along with the date and time when the status information is received. The remote control device then returns to the activity block 1962 to send another status request commend to the modified motor controller circuit to obtain updated status information. The process of repeatedly requesting status information may be timed by programmable delays or by internal timers within the remote control device. After a massage session is ended, the saved status information along with the data and time may be reviewed by the user. Depending on the results of a previous massage session, the user may choose to increase or decrease the pressure, increase or decrease the speed, increase or decrease the duration of the application of a particular pressure and speed, or a combination of variations. The user may also determine that the previous massage session was particularly helpful and may choose to reproduce the previous settings for a current setting.

In certain embodiments, the remote device (e.g., smartphone) includes application software (an "app") to enable the user to indicate certain portions of a recipient's body that are receiving percussive massages during segments of an overall massage session. For example, the app may display one or more images of a recipient's body (e.g., generic pictorial images) having target areas may be selected by the user to indicate that a massage segment is beginning on a certain portion of the recipient's body (e.g., the left trapezius muscle). The app records the information, as discussed above, as the massage segment is being performed. At the end of the massage segment, the user again selects the same target area to indicate the end of the massage segment or selects a new target area to start a new massage segment at a different location, which automatically ends the previous segment. The identification of the massage location is saved in the memory of the remote device along with the speed, pressure and duration of the massage segment in association with the name of the recipient. The stored information may also include feedback from the recipient and the user regarding the perceived effectiveness of the massage segment. When the recipient returns for a new massage session, the user may access the stored information from previous massage sessions and use the stored information to repeat the locations, speeds, pressures and durations of the previous segments or to modify one or more parameters of certain segments (e.g., decrease the pressure and increase the duration of the massage segment applied to the trapezius muscle). The stored information for a particular recipient may also be transferred to cloud storage to maintain a long-term percussive massage history.

Pressure Settings for Percussive Massage Applicators

Systems and processes for determining a pressure setting for a percussive massage applicator are disclosed. The percussive massage applicator may be referred herein as a smart exercise recovery device. The level of pressure that can be applied to the muscle tissue may be dependent on one or more factors. For instance, it is beneficial to maintain the pressure at the desired level for achieving desired pain relief and recovery and for providing an accurate therapeutic massage experience. Therefore, it can be helpful for a user of the applicator to accurately know the level of pressure or the relative level of pressure during operation. In some instances, the true level of pressure that is generated by the applicator may vary from the intended or calibrated pressure level of the applicator or may vary between individual applicators (e.g., due to manufacturing processes, the age of the applicator, the extent and/or frequency with which the applicator has been used, the battery age, the motor lifetime, etc.). For example, as the applicator gets older or after heavy use, there may be some load on the motor even when the applicator is not in physical contact with a human or object. This load may affect the pressure level outputted by the applicator. Therefore, it can be important to convey an accurate pressure level to a user of the particular applicator.

As discussed herein, the level of pressure may be expressed in the units of Pascal (Pa), bars, pressure per square inch (psi), etc. In some cases, the level of pressure may be expressed in terms of force applied (e.g., grams or pounds). The relative level of pressure may be based on the difference of one pressure level as compared to another pressure level. For example, the user may need to know that pressure is being increased or decreased by a certain amount with a change in setting. The relative level of pressure may be on a scale of pressure levels separated by predetermined amounts of pressure (e.g., 0.1 psi, 0.3 psi, 0.5 psi, 1 psi, etc.).

As discussed herein, vibration levels and motor speeds may be related to each other. In some instances, vibration levels and motor speeds may be used interchangeably. The following provides examples of vibration levels and motor speeds for an exemplary applicator:

TABLE 1

Example vibration levels and motor speeds for an exemplary applicator.

| Speed Ref. | Vibration Level (Hz) | Motor Speed (RPM) |
|---|---|---|
| 1 | 30 | 1800 |
| 2 | 40 | 2400 |
| 3a | 50 | 3000 |
| 3b | 53 | 3200 |

In some embodiments, a user of the applicator is provided with feedback via illuminated LEDs (e.g., pressure indicator LEDs 1572A, 1572B, 1572C) on the applicator. For example, the feedback can include the pressure level or the relative pressure level provided by the applicator. In a preferred embodiment, bright white LEDs can be used as a highly perceivable color. In other embodiments, differently colored LEDs (e.g., green, yellow, red, etc.) or monochromatically colored LEDs can be used to provide feedback. In some embodiments, at least three LEDs, at least five LEDs, at least ten LEDs, and so on may be used to convey the pressure level or relative pressure level to the end user. In some embodiments, the pressure level of the applicator can be conveyed via an app connected to the applicator. For example, the pressure level may be indicated via audio messages (e.g., more or less pressure) and/or via a visual gauge or a tachometer display on a remote device running the app.

The exemplary system may determine the level of pressure in the applicator using one or more of the following processes (alone or in combination):

Determining motor current consumption. In some embodiments, current consumption by the applicator's motor can be used to determine the pressure level of the applicator. For instance, increasing the pressure may increase the current consumption of the motor if a feedback loop regulates the speed of the motor. When there is no load on the applicator, the current consumption of the motor may not be very stable. The current consumption can depend on (i) the supply voltage, (ii) the age of the motor, (iii) the motor temperature, and/or (iv) permanently changing mechanical conditions (e.g., the motor rotor position when switching on the motor). These variable conditions may result in widely ranging no-load current values. In some cases, widely ranging current values may occur even when switching on the motor several times in a row.

If the exemplary massage applicator is used immediately after switching on the motor without waiting for a no-load condition to settle in (e.g., in a steady-state no-load condition), there may be little or no opportunity for the exemplary applicator to accurately determine the no-load motor current. It can be difficult to identify when the applicator attains a no-load condition or state. This may be true even when operating the applicator for a short time in a no-load condition after switching on the applicator.

Determining motor rotation speed. In some embodiments, the rotation speed of the applicator's motor can be used to determine the pressure level. In some cases, if there is no efficient motor speed regulation (or no regulation at all), increasing the pressure of the applicator can decrease the rotation speed of the motor. Therefore, the no-load rotation speed can be used for pressure level determination. The no-load speed can have the same or similar dependencies (e.g., (i) the supply voltage, (ii) the age of the motor, (iii) the motor temperature, and/or (iv) permanently changing mechanical conditions) as described above for determining the no-load current. Accordingly, determining the no-load speed based on the motor rotation speed may be difficult due to the issues described above for determining the no-load current.

Determining motor rotation pulse timing variations. In some embodiments, the motor pulse timing variations in the applicator's motor can be used to determine the pressure level. To measure the rotation time (and therefore the speed) of the motor, the exemplary systems may include one or more Hall sensors located around the rotor to generate a sensor signal (e.g., pulses). In some embodiments, the rotation speed may be determined by receiving, determining, or measuring the number of pulses per rotation generated by the motor from the sensor(s). By obtaining the number of pulses per rotation, the motor speed can be determined based on the time between these pulses. In some embodiments, variations in pulse timing may be expected. For example, variations may occur when the pressure of the applicator is increased, which in turn may slow down the motor when pressing against muscle tissue.

In some embodiments, as an initial step in pressure level determination, the no-load motor rotation pulse timing variations are determined. No-load motor rotation pulse timing variations are independent of the supply voltage, the age of the motor, and/or the motor temperature. However, they may be dependent on changing mechanical conditions including, e.g., the motor rotor position when switching on the motor. Accordingly, determining the no-load motor rotation pulse timing variations can be challenging for the reasons described above for determining the no-load current.

Determining the duty cycle of the motor speed control signal. In some embodiments, the duty cycle of a control signal of the applicator's motor can be used to determine the pressure level. In particular, the duty cycle of the control signal is configured to maintain the motor at the target speed. This process may be especially effective in determining pressure level for motors having a feedback loop in which the rotation speed is constant at a certain supply voltage and speed controlling duty cycle signal.

In some embodiments, the duty cycle required to get a certain motor speed is dependent on the supply voltage. In some cases, the supply voltage may be readily measured. Therefore, obtaining the supply voltage, the motor rotation speed, and the calibration data enables a highly accurate pressure level calculation. Note that, because a full calibration is attainable during the production (e.g., manufacturing) of the applicator, the need for calibration during normal operation may be eliminated.

Determining Motor Current Consumption

FIG. 37 is a flowchart illustrating an exemplary method 3700 for determining the pressure level of an applicator based, at least in part, on the current consumption of the applicator's motor. In activity block 3702 of exemplary method 3700, after assembly of the massage applicator and/or before regular use of the applicator, an initial measurement of the no-load motor current magnitude (e.g., INO-LOAD) at some, most, or all possible vibration levels can be obtained. For example, a no-load current value can be obtained by averaging multiple samples (e.g., up to 10 samples, up to 20 samples, up to 40 samples, or more) at some, most, or all vibration levels. The measurement values may be stored in non-volatile memory and may be used in determining the pressure level. Measurement values may be stored before a calibration in normal operation is performed on the applicator.

During normal operation, when the motor of a device is operating (turned on), variations in the motor rotation speed and/or variations in the current consumption of the motor may be monitored. The monitoring can enable the detection of a no-load condition and/or state in the applicator, e.g., during operation. For example, a no-load condition may occur during operation when the applicator is removed from application on a body and therefore transitions from a loaded state (on the body) to a no-load state (away from the body). Monitoring these signals can be effective because, when the motor current is close to a no-load condition and/or state, rotation speed variations can occur under a small load. By contrast, when the applicator is operating without a load, these variations tend to be close to zero or at zero. Therefore, whenever there is zero or nearly zero variations at a current level close to the expected no-load current, a no-load condition can be determined. Subsequently, a calibration of the no-load current can be performed. In particular, the initial no-load current magnitude (e.g., INO-LOAD) measured before use of the applicator can be set to the no-load current magnitude (e.g., a new INO-LOAD) determined during operation after the applicator is removed away from the body. This background calibration can significantly improve the accuracy of the pressure level determination. Additionally, this calibration can be used to adjust the motor speed as the user changes from one pressure setting to another pressure setting during a therapy session (refer to FIGS. 30-31 and related description).

In activity block 3704 of method 3700, the operational motor current magnitude during normal operation is obtained (e.g., received or determined). As described above, operational motor current magnitude may be determined when the applicator is in use, being applied to a person or object, etc. such that a load is present.

In activity block 3706, the no-load current (as determined above) is subtracted from the measured motor current during normal operation (e.g., with a load). In activity block 3708, the resulting "difference" value of the motor current can be compared to one or more predetermined levels (e.g., one or more ranges of values) corresponding to the pressure levels of the applicator. The below table provides exemplary predetermined ranges of values (e.g., three ranges of values) that correspond to pressure levels (e.g., Levels 1-3). In activity block 3710, the predetermined range of values that includes the difference value can be selected as the determined pressure level.

TABLE 1

Example ranges of values for motor current corresponding to pressure levels in an applicator.

| Predetermined range of values | Pressure levels | Pressure (psi) |
|---|---|---|
| 0 mA to 500 mA | Level 1 (low) | 0.0 to 1.6 |
| 500 mA to 550 mA | Level 2 (medium) | 1.7 to 3.3 |
| 550 mA to 600 mA | Level 3 (high) | 3.4 to 5.0 |

In some embodiments, these predetermined levels may be communicated to a user of the applicator via one or more LEDs. For instance, when one or more predetermined levels is exceeded, a corresponding number of LEDs is switched on. Similarly, when the subtracted value is less than one or more predetermined levels, the corresponding number of LEDs may be switched off. In some embodiments, for a decreasing motor current, the predetermined levels are slightly decreased before switching off the corresponding LED. For example, if the predetermined levels corresponded to pressure level 1 and pressure level 2, then the slightly decreased levels would be at 0.9 and 1.9, respectively. This hysteresis prevents a flashing LED (which may be confusing or aesthetically displeasing to a user) when the motor current is close to one of the levels (e.g., close to a lower bound of a range of values for the level).

In some embodiments, the last measured no-load current(s) are stored in non-volatile memory overwriting any previously stored values. The stored no-load current values can be used as default values the next time the massage device is powered on, e.g., before performing a new calibration. This may improve the accuracy of the pressure level determination in some applicators, e.g., in older and/or heavily used devices that typically exhibit a higher no-load current.

Determining Motor Rotation Speed

FIG. 38 is a flowchart illustrating an exemplary method 3800 for determining the pressure level of an applicator based, at least in part, on the motor rotation speed of the applicator. In activity block 3802 of exemplary method 3800, after assembly of the massage applicator and/or before regular use of the applicator, a first measurement of the no-load rotation speed at some, most, or all possible vibration levels can be obtained. For example, a no-load rotation speed can be obtained by averaging multiple samples (e.g., up to 10 samples, up to 20 samples, up to 40 samples, or more) at some, most, or all vibration levels. The measurement values may be stored in non-volatile memory and may be used in determining the pressure level before a calibration on the applicator in normal operation is performed.

In normal operation, when the motor is operating (switched on), variations in the motor rotation speed and/or the rotation speed itself may be monitored to detect a no-load condition and/or state. In some instances, when the applicator is operating with a motor rotation speed close to no-load conditions, rotation speed variations can be observed with a small load. Without a load, these variations tend to be close to zero. Therefore, when there are almost no variations at a rotation speed close to the expected no-load speed, a true no-load condition can be assumed and a calibration of the no-load rotation speed can be performed, as discussed above. This background calibration can significantly improve the accuracy of the pressure level determination. Additionally, this calibration can be used to adjust the motor speed as the user changes from one pressure setting to another pressure setting during a therapy session (refer to FIGS. 30-31 and related description).

In activity block 3804 of method 3800, the operational motor rotation speed during normal operation is obtained (e.g., received or determined). Operational motor rotation speed may be determined when the applicator is in use, being applied to a person or object, etc. such that a load is present.

In activity block 3806, the absolute value of difference between the measured motor rotation speed (e.g., with a load) and the no-load motor rotation speed can be determined. For example, the measured motor rotation speed can be subtracted from the no-load motor rotation speed. In activity block 3808, the resulting "difference" value of the motor rotation speed can be compared to predetermined levels (e.g., one or more ranges of values) corresponding to the pressure levels of the applicator. The below table provides exemplary predetermined ranges of values (e.g., three ranges of values) that correspond to pressure levels (Levels 1-3). In activity block 3810, the predetermined range of values that includes the difference value can be selected as the determined pressure level.

TABLE 2

Example ranges of values corresponding to pressure levels in an applicator.

| Predetermined range of values | Pressure levels | Pressure (psi) |
|---|---|---|
| 1750 RPM to 1850 RPM | Level 1 (low) | 0.0 to 1.6 |
| 2250 RPM to 2350 RPM | Level 2 (medium) | 1.7 to 3.3 |
| 2750 RPM to 2850 RPM | Level 3 (high) | 3.4 to 5.0 |

In some embodiments, these predetermined levels may be communicated to a user of the applicator via one or more LEDs. For instance, when one or more predetermined levels is exceeded, a corresponding number of LEDs is switched on. Similarly, when the subtracted value is less than one or more predetermined levels, the corresponding number of LEDs may be switched off In some embodiments, for an decreasing motor speed, these levels will be slightly decreased before switching off the corresponding LED. For example, if the predetermined levels corresponded to pressure level 1 and pressure level 2, then the slightly decreased levels would be at 0.9 and 1.9, respectively. This hysteresis can prevent a flashing LED (which may be confusing or aesthetically displeasing to a user) when the motor speed is close to one of the levels (e.g., close to a lower bound of a range of values for the level).

In some embodiments, the more recent measured no-load rotation speed value(s) are stored in non-volatile memory overwriting any previously stored values. The stored rotation speed value(s) can be used as default values when performing a new calibration after turning on (e.g., switching on) the applicator. This may improve the accuracy of the pressure level determination in some applicators, e.g., in older and/or heavily used devices that typically exhibit a lower no-load rotation speed.

Determining Motor Rotation Pulse Timing Variations

FIG. 39 is a flowchart illustrating an exemplary method 3900 for determining the pressure level of an applicator based, at least in part, on rotation pulse timing variations of the applicator's motor. In activity block 3902 of exemplary method 3900, after assembly of the massage applicator and/or before regular use of the applicator, a first measurement of the motor rotation pulse timing variations at some, most, or all possible vibration levels can be obtained. The measurement values may be stored in non-volatile memory and may be used in determining the pressure level. Measurement values may be stored before a calibration on the applicator in normal operation is performed on the applicator.

During normal operation, when the motor of the applicator is operating (switched on), the motor rotation speed and/or the motor current (or variations of the rotation speed or the motor current) may be monitored. The monitoring can enable the detection of a no-load condition and/or state in the applicator, e.g., during operation. In some instances, when the applicator is operating with a motor rotation speed and/or motor current close to no-load conditions, rotation speed variations can be observed when under a small load. By contrast, when the applicator is operating without a load, these variations tend to be close to zero or at zero. Therefore, when there are zero or nearly zero rotation speed variations at a rotation speed close to the expected no-load speed or current, a no-load condition can be detected. Subsequently, a calibration of the no-load rotation pulse timing variations can be performed. This background calibration can significantly improve the accuracy of the pressure level determination. Additionally, this calibration can be used to adjust the motor speed as the user changes from one pressure setting to another pressure setting during a therapy session (refer to FIGS. 30-31 and related description).

In activity block 3904 of method 3900, the operational pulse timing variation during normal operation is obtained (e.g., received or determined). The operational pulse timing variation may be determined when the applicator is in use, being applied to a person or object, etc. such that a load is present.

In activity block 3906, the pulse timing exhibiting the greatest variation is detected. For example, pulse timing can be monitored over a time period of 5 milliseconds (or in a time period within, e.g., 1 millisecond and 30 milliseconds). and the greatest variation over that time period can be detected. The greatest variation can be selected by plotting the variations over the time period and selecting the highest peak. The variation at a no-load state (as determined above) is subtracted from the measured variation during normal operation (e.g., with a load). In activity block 3908, the resulting "difference" value of the pulse timing variation is compared to one or more predetermined levels (e.g., one or more ranges of values) corresponding to the pressure levels of the applicator. The below table provides exemplary predetermined ranges of values (e.g., three ranges of values) that correspond to pressure levels (e.g., Levels 1-3). In activity block 3910, the predetermined range of values that includes the difference value can be selected as the determined pressure level.

TABLE 3

Example ranges of values for pulse timing variation corresponding to pressure levels in an applicator.

| Predetermined range of values | Pressure levels | Pressure (psi) |
|---|---|---|
| 30 ms to 25 ms | Level 1 (low) | 0.0 to 1.6 |
| 25 ms to 20 ms | Level 2 (medium) | 1.7 to 3.3 |
| 20 ms to 0 ms | Level 3 (high) | 3.4 to 5.0 |

In some embodiments, these predetermined levels may be communicated to a user of the applicator via one or more LEDs. For instance, when one or more predetermined levels is exceeded, the corresponding number of LEDs is switched on. Similarly, when the subtracted value is less than one or more predetermined levels, the corresponding number of LEDs may be switched off In some embodiments, when the pressure levels decreases, the LED threshold levels are slightly decreased before switching off the corresponding LED. This hysteresis can prevent a flashing LED (which may be confusing or aesthetically displeasing to a user) whenever the variation is close to one of the levels (e.g., close to a lower bound of a range of values for the level).

In some embodiments, the more recent determined no-load variation values are stored in non-volatile memory thereby overwriting any previously stored values. The stored variation value(s) can be used as default values when performing a new calibration after turning on (e.g., switching on) the applicator. This may improve the accuracy of the pressure level determination in some applicators, e.g., in older and/or heavily used devices that typically exhibit slightly higher no-load variations.

Determining the Duty Cycle of the Motor Speed Control Signal

FIG. 40 is a flowchart illustrating an exemplary method 4000 for determining the pressure level of an applicator based, at least in part, on the duty cycle for the applicator's motor. The duty cycle of a control signal configured for a certain motor speed can be dependent on the supply voltage. In activity block 4002 of exemplary method 4000, the duty cycle value(s) used to obtain the one or more vibration levels at a no-load condition can be measured at a known supply voltage after the assembly of the applicator and/or before regular use of the applicator. The duty cycle values can be stored in non-volatile memory with the corresponding supply voltage. In some embodiments, the dependency of the duty cycle on supply voltage is linear. The deviation of its slope of the linear relationship can be low between different motors of individual applicators. However, according to one embodiment, no-load duty cycle values can be measured at the minimum and maximum possible supply voltages to determine the slope and stored for the corresponding specific motor. The calibration values of the no-load duty cycle can be used to adjust the motor speed as the user changes from one pressure setting to another pressure setting during a therapy session (refer to FIGS. 30-31 and related description).

In activity block 4004 of method 4000, the operational duty cycle during normal operation is obtained (e.g., received or determined). Operational duty cycle may be determined when the applicator is in use, being applied to a person or object, etc. such that a load is present.

In activity block 4006 during normal operation, the no-load duty cycle of the selected vibration level can be calculated for the supply voltage and the no-load duty cycle can be subtracted from the duty cycle (e.g., with a load). This calculation may be performed continuously as the supply voltage is dependent on the pressure level. In activity block 4008, the resulting "difference" value of the duty cycle is compared to predetermined levels (e.g., one or more ranges of values) corresponding to the pressure levels of the applicator. The below table provides exemplary predetermined ranges of values (e.g., three ranges of values) that correspond to pressure levels (Levels 1-3). In activity block 4010, the predetermined range of values that includes the difference value can be selected as the determined pressure level.

TABLE 4

Example ranges of values for duty cycle corresponding to pressure levels in an applicator.

| Predetermined range of values | Pressure levels | Pressure (psi) |
| --- | --- | --- |
| 0% to 50% | Level 1 (low) | 0.0 to 1.6 |
| 50% to 70% | Level 2 (medium) | 1.7 to 3.3 |
| 70% to 90% | Level 3 (high) | 3.4 to 5.0 |

In some embodiments, these predetermined levels may be communicated to a user of the applicator via one or more LEDs. For instance, when one or more predetermined levels is exceeded, the corresponding number of LEDs is switched on. Similarly, when the subtracted value is less than one or more predetermined levels, the corresponding number of LEDs may be switched off. In some embodiments, when decreasing the duty cycle and/or pressure, the duty cycle LED threshold levels are slightly decreased before switching off the corresponding LED. This hysteresis can prevent a flashing LED (which may be confusing or aesthetically displeasing to a user) whenever the variation is close to one of the levels (e.g., close to a lower bound of a range of values for the level).

Computer-Based Implementations

The term "system" may encompass all kinds of apparatus, devices, and machines for processing data, including by way of example a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

The phraseology and terminology used herein is for the purpose of description and should not be regarded as limiting.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B,") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

As various changes could be made in the above constructions without departing from the scope of the invention, it is intended that all the matter contained in the above description or shown in the accompanying drawings shall be interpreted as illustrative and not in a limiting sense.

What is claimed is:

1. A method for determining a pressure level of a massage applicator, the method comprising:
   obtaining a first value for a parameter of a motor of the applicator when the applicator has no load;
   obtaining a second value for the parameter of the motor when the applicator has a load;
   determining a difference value between the first value and the second value;
   comparing the difference value to two or more predetermined ranges of values that correspond to a pressure level of the applicator; and
   selecting the predetermined range that comprises the difference value, thereby determining the pressure level of the applicator.

2. The method of claim 1, wherein obtaining the first value of the parameter comprises obtaining the first value of the parameter at each of a plurality of vibration levels, the vibration levels related to a speed of the motor.

3. The method of claim 1, wherein obtaining the first value of the parameter comprises:
   obtaining at least 40 first values of the parameter; and
   averaging the at least 40 first values to determine the average first value of the parameter.

4. The method of claim 1, wherein the parameter is a current magnitude.

5. The method of claim 1, wherein the parameter is a rotation speed.

6. The method of claim 1, wherein the parameter is a reading of variations in a rotation pulse.

7. The method of claim 1, wherein the parameter is a duty cycle of a control signal.

8. The method of claim 1, further comprising:
   providing the determined pressure level of the applicator in a user interface.

9. The method of claim 8, wherein the user interface is at least one of: (i) a plurality of LEDs; (ii) a plurality of auditory signals; or (iii) a plurality of vibratory signal.

10. The method of claim 1, wherein the applicator has a load when applied to a body.

11. The method of claim 1, further comprising:
    storing the obtained first value for the parameter in memory.

12. The method of claim 11, wherein obtaining the first value for the parameter of the motor comprises retrieving the stored first value for the parameter from the memory.

13. The method of claim 1, wherein the first value of the parameter is obtained following assembly of the massage applicator and before regular use.

14. The massage applicator of claim 1, further comprising a user interface coupled to the processor, wherein the processor is further configured to:
    provide the determined pressure level of the applicator in a user interface.

15. A massage applicator comprising:
    a motor; and
    a processor coupled to the motor and configured to:
       obtain a first value for a parameter of the motor when the applicator has no load;
       obtain a second value for the parameter of the motor when the applicator has a load;
       determine a difference value between the first value and the second value;
       compare the difference value to two or more predetermined ranges of values that correspond to a pressure level of the applicator; and
       select the predetermined range that comprises the difference value, thereby determining the pressure level of the applicator.

16. The massage applicator of claim 15, wherein the processor is further configured to obtain the first value of the parameter at each of a plurality of vibration levels, the vibration levels related to a speed of the motor.

17. The massage applicator of claim 15, wherein the parameter is a current magnitude.

18. The massage applicator of claim 15, wherein the parameter is a rotation speed.

19. The massage applicator of claim 15, wherein the parameter is a reading of variations in a rotation pulse.

20. The massage applicator of claim 15, wherein the parameter is a duty cycle of a control signal.

* * * * *